(12) United States Patent
Joo et al.

(10) Patent No.: US 12,005,040 B2
(45) Date of Patent: Jun. 11, 2024

(54) METAL AND CERAMIC NANOFIBERS

(71) Applicant: CORNELL UNIVERSITY, Ithaca, NY (US)

(72) Inventors: Yong Lak Joo, Ithaca, NY (US); Nathaniel S. Hansen, Portland, OR (US); Daehwan Cho, Austin, TX (US)

(73) Assignee: CORNELL UNIVERSITY, Ithaca, NY (US)

( * ) Notice: Subject to any disclaimer, the term of this patent is extended or adjusted under 35 U.S.C. 154(b) by 87 days.

(21) Appl. No.: 17/330,760

(22) Filed: May 26, 2021

(65) Prior Publication Data

US 2021/0283084 A1 Sep. 16, 2021

Related U.S. Application Data

(63) Continuation of application No. 16/239,172, filed on Jan. 3, 2019, now abandoned, which is a continuation of application No. 14/342,012, filed as application No. PCT/US2012/053097 on Aug. 30, 2012, now abandoned.

(60) Provisional application No. 61/636,095, filed on Apr. 20, 2012, provisional application No. 61/528,895, filed on Aug. 30, 2011.

(51) Int. Cl.
| | |
|---|---|
| *H01B 1/20* | (2006.01) |
| *A61K 31/202* | (2006.01) |
| *A61K 31/232* | (2006.01) |
| *B22F 1/054* | (2022.01) |
| *B22F 1/07* | (2022.01) |
| *B22F 9/30* | (2006.01) |
| *B82Y 30/00* | (2011.01) |
| *C04B 35/622* | (2006.01) |
| *D01D 5/00* | (2006.01) |
| *D01F 1/10* | (2006.01) |
| *D01F 9/08* | (2006.01) |
| *D04H 1/4234* | (2012.01) |
| *D04H 1/728* | (2012.01) |
| *H01B 1/02* | (2006.01) |
| *H01B 1/08* | (2006.01) |

(52) U.S. Cl.
CPC .......... *A61K 31/202* (2013.01); *A61K 31/232* (2013.01); *B22F 1/0547* (2022.01); *B22F 1/07* (2022.01); *B22F 9/30* (2013.01); *B82Y 30/00* (2013.01); *C04B 35/62227* (2013.01); *C04B 35/62231* (2013.01); *C04B 35/62236* (2013.01); *C04B 35/6224* (2013.01); *C04B 35/6225* (2013.01); *C04B 35/62254* (2013.01); *C04B 35/62259* (2013.01); *D01D 5/0007* (2013.01); *D01D 5/0015* (2013.01); *D01F 1/10* (2013.01); *D01F 9/08* (2013.01); *D04H 1/4234* (2013.01); *D04H 1/728* (2013.01); *H01B 1/02* (2013.01); *H01B 1/026* (2013.01); *H01B 1/08* (2013.01); *C04B 2235/40* (2013.01); *C04B 2235/441* (2013.01); *C04B 2235/443* (2013.01); *C04B 2235/444* (2013.01); *C04B 2235/449* (2013.01); *C04B 2235/526* (2013.01); *C04B 2235/5264* (2013.01); *C04B 2235/5296* (2013.01)

(58) Field of Classification Search
CPC ...... D01D 5/0007; D01D 5/0015; D01F 1/10; D01F 9/08; H01B 1/02; H01B 1/026; H01B 1/08
See application file for complete search history.

(56) References Cited

U.S. PATENT DOCUMENTS

| | | |
|---|---|---|
| 2,810,426 A | 10/1957 | Till et al. |
| 7,326,043 B2 | 2/2008 | Joo et al. |
| 7,575,707 B2 | 8/2009 | Xia et al. |
| 7,887,311 B2 | 2/2011 | Chu et al. |
| 7,901,610 B2 | 3/2011 | Joo et al. |
| 8,066,932 B2 | 11/2011 | Xu |
| 8,512,741 B2 | 8/2013 | Tan et al. |
| 9,005,510 B2 | 4/2015 | Ishaque et al. |
| 9,102,570 B2 | 8/2015 | Joo et al. |
| 9,267,220 B2 | 2/2016 | Joo et al. |
| 9,457,538 B2 | 10/2016 | Smith et al. |
| 2006/0013869 A1 | 1/2006 | Ignatious et al. |
| 2007/0269655 A1 | 11/2007 | Joo et al. |
| 2008/0233284 A1 | 9/2008 | Kim et al. |

(Continued)

FOREIGN PATENT DOCUMENTS

| | | |
|---|---|---|
| CA | 2779661 A1 | 5/2011 |
| CN | 101126179 | 2/2008 |

(Continued)

OTHER PUBLICATIONS

Intellectual Property of India for Application No. 2372/CHENP/2014, dated Oct. 14, 2021, 7 pages.

*Primary Examiner* — Haidung D Nguyen
(74) *Attorney, Agent, or Firm* — Barnes & Thornburg LLP

(57) ABSTRACT

Provided herein are nanofibers and processes of preparing nanofibers. In some instances, the nanofibers are metal and/or ceramic nanofibers. In some embodiments, the nanofibers are high quality, high performance nanofibers, highly coherent nanofibers, highly continuous nanofibers, or the like. In some embodiments, the nanofibers have increased coherence, increased length, few voids and/or defects, and/or other advantageous characteristics. In some instances, the nanofibers are produced by electrospinning a fluid stock having a high loading of nanofiber precursor in the fluid stock. In some instances, the fluid stock comprises well mixed and/or uniformly distributed precursor in the fluid stock. In some instances, the fluid stock is converted into a nanofiber comprising few voids, few defects, long or tunable length, and the like.

8 Claims, 41 Drawing Sheets

(56) References Cited

U.S. PATENT DOCUMENTS

| | | |
|---|---|---|
| 2010/0009267 A1 | 1/2010 | Chase et al. |
| 2010/0028674 A1 | 2/2010 | Ochanda |
| 2010/0155691 A1 | 6/2010 | Lee et al. |
| 2011/0151255 A1 | 6/2011 | Kim et al. |
| 2012/0217681 A1 | 8/2012 | Zieba et al. |

FOREIGN PATENT DOCUMENTS

| | | |
|---|---|---|
| CN | 101235558 A | 8/2008 |
| CN | 101266225 B | 12/2010 |
| CN | 101905974 B | 11/2011 |
| DK | 1867762 T3 | 12/2008 |
| EP | 1867762 | 12/2007 |
| EP | 2204349 | 7/2010 |
| EP | 2267199 | 12/2010 |
| JP | 2005520068 | 7/2005 |
| JP | 2009235629 | 10/2009 |
| JP | 2009275339 | 11/2009 |
| JP | 2010095826 | 4/2010 |
| JP | 2010145388 | 7/2010 |
| JP | 2011073912 | 4/2011 |
| JP | 2011073912 A | 4/2011 |
| JP | 2011106050 | 6/2011 |
| JP | 5105075 B2 | 12/2012 |
| JP | 5375022 B2 | 12/2013 |
| JP | 5642956 B2 | 12/2014 |
| KR | 100549140 B1 | 2/2006 |
| KR | 100675923 B1 | 1/2007 |
| KR | 100812357 B1 | 3/2008 |
| KR | 1020100038979 A | 4/2010 |
| KR | 100995154 B1 | 11/2010 |
| KR | 101014260 B1 | 2/2011 |
| KR | 101191386 B1 | 10/2012 |
| KR | 101265093 B1 | 5/2013 |
| WO | 2003080905 | 10/2003 |
| WO | 2007073111 | 6/2007 |
| WO | 2008030457 A2 | 3/2008 |
| WO | 2008111960 | 9/2008 |
| WO | 2010122049 | 10/2010 |
| WO | 2011054701 | 5/2011 |
| WO | 2011100743 | 8/2011 |

Ni/ZrO$_2$

Fe/ZrO$_2$

ZnO/ZrO$_2$

Ag/ZrO$_2$

Fe$_3$O$_4$/FeNi$_3$

Sheath: ZrO₂
Core: Ni

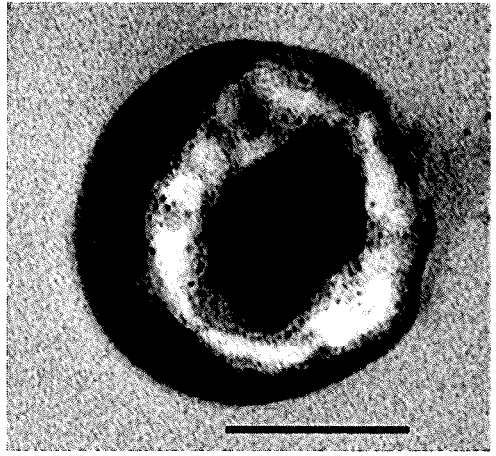
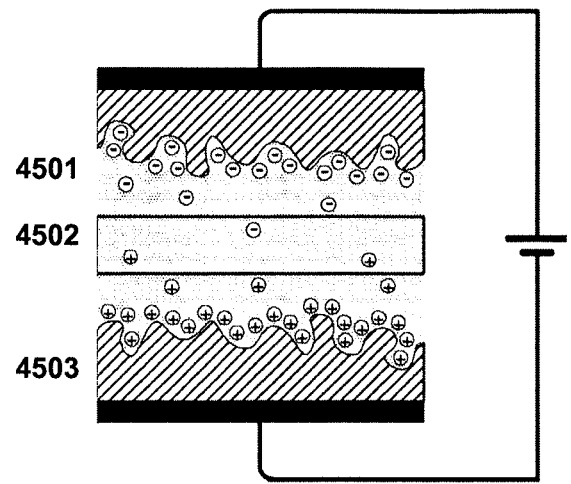
FIG. 44    FIG. 45
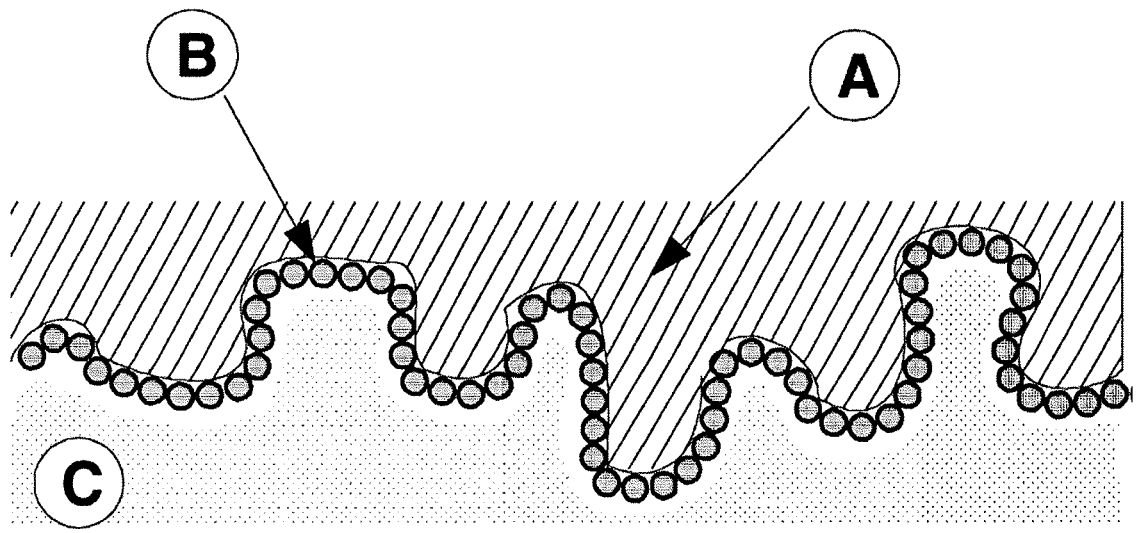
FIG. 46

METAL AND CERAMIC NANOFIBERS

CROSS-REFERENCE

This application is a continuation of U.S. Non-Provisional application Ser. No. 16/239,172, filed on Jan. 3, 2019, which is a continuation of U.S. Non-Provisional application Ser. No. 14/342,012, filed Jun. 9, 2014, which is a National Stage Entry of PCT/US12/53097, filed Aug. 30, 2012, which claims the benefit of U.S. Provisional Application Nos. 61/528,895, filed Aug. 30, 2011, and 61/636,095, filed Apr. 20, 2012, each of which is incorporated herein by reference in their entireties.

BACKGROUND OF THE INVENTION

Ceramic and metallic nanofibers have potential for applications in a wide variety of fields, including high performance filtration, chemical sensing, biomedical engineering and renewable energy. Previous methods for producing ceramic or metallic nanofibers include the electrospinning of sol-gel precursors with or without a polymer binder. However, the nanofibers produced by the sol-gel method have many disadvantages, such as low performance and poor coherence, which makes them unsuitable for many applications.

SUMMARY OF THE INVENTION

Provided herein are nanofibers and processes for producing nanofibers. In some instances, the nanofibers are metal, metal oxide, and/or ceramic nanofibers. In some embodiments, the nanofibers are high quality nanofibers, high performance nanofibers, highly coherent nanofibers, highly continuous nanofibers, or the like. In some embodiments, the nanofibers are coherent, are long, have few voids and/or defects, and/or have other advantageous characteristics such as flexible control of metal and/or ceramic crystal sizes. In some instances, the nanofibers are produced by electrospinning a fluid stock comprising a high concentration of ceramic or metal precursor in the fluid feed stock. In some instances, the fluid stock further comprises well mixed or substantially uniformly distributed precursor in the fluid stock. In some embodiments, the fluid stock is converted to a nanofiber comprising few voids, few defects, long or tunable lengths, and the like.

Provided in certain embodiments herein is a process for producing one or more nanofiber, the process comprising electrospinning a fluid stock, the fluid stock comprising metal precursor(s) and polymer, and
  the weight to weight ratio of the precursor(s) to polymer being at least 1:2;
  the fluid stock being aqueous;
  the precursor(s) being present in the fluid stock in a concentration of at least 200 mM; or
  any combination thereof.

In specific embodiments, the fluid stock is (1) a solution; (2) a substantially uniform dispersion (e.g., of the precursor(s)); or (3) a substantially homogenous dispersion (e.g., homogeneous dispersion of the precursor(s)). In further or alternative embodiments, the weight-to-weight ratio of the precursor(s) to polymer in the fluid stock is at least 1:2 (e.g., over 1:2) and the fluid stock is aqueous. In specific embodiments, the weight-to-weight ratio of the precursor(s) to polymer is at least 1:1. In further or alternative embodiments, the fluid stock is prepared by combining reagent precursor(s), reagent polymer(s) and water to form the fluid stock comprising the precursor(s) and the polymer, and wherein the reagent precursor(s) and reagent polymer(s) are combined in a weight to weight ratio of over 1:2. In specific embodiments, the reagent precursor(s) and reagent polymer(s) are combined the in a weight-to-weight ratio of at least 1:1. In further or alternative embodiments, one or more of the precursor(s) are present in the fluid stock in a polymer-precursor association. In specific embodiments, at least 50% of the polymer is saturated with precursor molecules. In further or alternative embodiments, at least 50% of the precursor molecules are associated with polymer. In further or alternative embodiments, the precursor(s) is present in the fluid stock in a concentration of at least 200 mM (e.g., over 200 mM, at least 250 mM, or the like). In specific embodiments, the precursor(s) concentration in the fluid stock is at least 250 mM. In more specific embodiments, the precursor(s) concentration in the fluid stock is at least 300 mM. In further or alternative embodiments, the metal precursor(s) comprises one or more metal-ligand complex. In specific embodiments, the metal-ligand complex is in association with the polymer. In further or alternative embodiments, the metal precursor comprises metal selected from the group consisting of: Ag, Cu, Ni, Fe, Co, Pb, Au, Sn, Al, Zr, Li, Mn, Cr, Be, Cd, Si, Ti, V, Hf, Sr, Ba, Ge, and combinations thereof. In further or alternative embodiments, the metal precursor comprises a transition metal, or metalloid. In further or alternative embodiments, the metal precursor is a metal-ligand complex comprising one or more ligand selected from the group consisting of: a carboxylate, a nitrate, a halide, a diketone, an alkoxide, and combinations thereof. In further or alternative embodiments, the reagent precursor, the precursor of the fluid stock, or both comprise one or more metal acetate, metal nitrate, metal chloride, metal methoxide, or a combination thereof. In further or alternative embodiments, the polymer is polyvinyl alcohol (PVA), polyvinyl acetate (PVAc), polyethylene oxide (PEO), polyvinyl ether, polyvinyl pyrrolidone, polyglycolic acid, hydroxyethylcellulose (HEC), ethylcellulose, cellulose ethers, polyacrylic acid, polyisocyanate, or a combination thereof. In further or alternative embodiments, the polymer is (i) hydrophilic, and (ii) water soluble or water swellable. In further or alternative embodiments, the polymer is thermally and/or chemically degradable. In further or alternative embodiments, the polymer is a polymer comprising a plurality of nucleophilic moieties and the reagent precursor is electrophilic. In other embodiments, the polymer is a polymer comprising a plurality of electrophilic moieties and the reagent precursor is nucleophilic. In some embodiments, electrospinning the fluid stock results in the formation of electrospun nanofiber material comprising metal precursor and polymer. In further or alternative embodiments, the process further comprises treating (calcining) the electrospun material to prepare a calcinated nanofiber. In specific embodiments, the treatment (calcining) of the electrospun material comprises thermally treating the electrospun material, chemically treating the electrospun material, or both. In further or alternative embodiments, the process further comprises removing (e.g., by calcination) polymer from the electrospun material. In specific embodiments, calcining the electrospun material (e.g., under inert or reducing conditions) converts metal precursor to metal. In further or alternative embodiments, calcining the electrospun material (e.g., under oxidative conditions) converts metal precursor to metal oxide. In further or alternative embodiments, calcining the electrospun material (e.g., under oxidative conditions) converts metal precursor to ceramic. In further or alternative embodiments, calcining the electrospun material (e.g., first under oxidative conditions and subsequently under reducing conditions) converts a first metal precursor to ceramic and a second metal precursor to metal. In further or alternative embodiments, the process comprises calcining the electrospun material under oxidative conditions, thereby converting metal precursor to metal oxide (e.g., ceramic metal oxide). In further or alternative embodiments, the process comprises calcining electrospun material the nanofiber under inert or reducing conditions, thereby converting metal precursor to metal. In further or alternative embodiments, calcining the electrospun material comprises heating the electrospun material to a temperature of at least 400° C. (e.g., at least 500° C. or at least 600° C.). In further or alternative embodiments, the fluid stock is co-axially electrospun with a second fluid. In specific embodiments, the second fluid is a gas (e.g., air). In other specific embodiments, the second fluid is a second fluid stock comprising a second metal precursor and a second polymer, wherein the metal precursor and second metal precursor are the same or different and the polymer and second polymer are the same or different, and wherein the process produces a layered nanofiber (optionally comprising coaxially electrospinning with a third fluid that is a gas, e.g., air). In further or alternative embodiments, the metal precursor and polymer being present (in the fluid stock or precursor nanofiber) in a weight-to-weight ratio of at least 1:2 (e.g., at least 1:1). In further or alternative embodiments, provided herein is a nanofiber prepared according to any process described herein. In some embodiments, provided herein is a nanofiber prepared by or preparable by any process described herein. In specific embodiments, the nanofiber is a precursor or electrospun nanofiber prepared or preparable prior to calcination. In other specific embodiments, the nanofiber is a metal, metal oxide, or ceramic containing nanofiber prepared or preparable following calcination.

In some embodiments, provided herein is a precursor nanofiber comprising polymer (e.g., organic polymer and metal precursor. In some embodiments, the precursor nanofiber has high metal precursor loading (e.g., at least 1:2, metal precursor:polymer; over 1:2; at least 1:1.75; at least 1:1.5; at least 1:1; or the like). In some embodiments, the precursor (i.e., electrospun) nanofiber (e.g., as prepared according to any process described herein), comprises at least 90% by weight of organic polymer and metal precursor. In further or alternative embodiments, the precursor (i.e., electrospun) nanofiber comprises at least 5 elemental wt. % metal (e.g., at least 10 elemental wt. %, or at least 15 elemental wt. % metal).

In certain embodiments, provided herein is a nanofiber or plurality of nanofibers comprising metal, metal oxide, ceramic, or a combination thereof, and:
the nanofibers are at least 50 μm (e.g., at least 100 μm) long (e.g., on average);
the nanofibers have an (e.g., average) aspect ratio of at least about 10 (e.g., at least about 100);
the nanofibers comprise a continuous matrix of a metal, a metal oxide, ceramic, or a combination thereof (e.g., the continuous matrix running along, e.g., on average, at least 80% of the length of the nanofiber; or at least 90% the length of the nanofiber; or at least 95% the length of the nanofiber);
the nanofibers have an average specific surface area between 1 m$^2$/g and about 1000 m$^2$/g; or
a combination thereof.

In specific embodiments, the nanofibers have feature (a). In further or alternative embodiments, the nanofibers have feature (b). In further or alternative embodiments, the nanofibers have feature (c). In further or alternative embodiments, the nanofibers have feature (d). In specific embodiments, the nanofibers have features (a) and (b). In other specific embodiments, the nanofibers have features (b) and (c). In still other embodiments, the nanofibers have features (a), (b) and (c). In some embodiments, the nanofibers comprise at least 33% (w/w) (e.g., on average) of a metal, a metal oxide, a ceramic, or, taken together, a combination thereof. In further or alternative embodiments, the nanofibers are metal nanofibers comprising at least 90 elemental wt. % of metal (e.g., on average). In further or alternative embodiments, the nanofibers are metal oxide nanofibers comprising at least 90% metal oxide (e.g., on average) and at least 30 elemental wt. % of metal (e.g., on average). In further or alternative embodiments, the nanofibers are ceramic nanofibers comprising at least 90% ceramic (e.g., on average) and at least 30 elemental wt. % of metal (e.g., on average). In further or alternative embodiments, the nanofibers are metal alloy nanofibers comprising at least 90% metal alloy (e.g., on average) and at least 30 elemental wt. % of metal (e.g., on average). In further or alternative embodiments, the nanofibers are composite nanofibers comprising a first material and a second material, the first material being a continuous matrix material, and one or both of the first material or second material comprising metal, metal oxide, ceramic, or a combination thereof. In further or alternative embodiments, the second material is a second continuous matrix material (e.g., the first and second continuous matrix materials are coaxial layers). In other embodiments, the second material comprises isolated domains of the nanofibers. In further or alternative embodiments, one or both of the first or second materials comprises metal and the nanofibers comprising an average of at least 5 elemental wt. % of metal (e.g., at least 20 elemental wt. % of metal) (e.g., on average). In further or alternative embodiments, the first material is ceramic and the second material is metal. In alternative embodiments, the first material is metal and the second material is metal. In alternative embodiments, the first material is ceramic and the second material is ceramic. In further or alternative embodiments, the nanofiber comprises at least 30 elemental wt. % of metal (e.g., on average). In specific embodiments, the nanofibers comprises at least 50 elemental wt. % of metal (e.g., on average). In further or alternative embodiments, the metal (of the metal, metal oxide, ceramic, or the like) is selected from the group consisting of Ag, Cu, Ni, Fe, Co, Pb, Au, Sn, Al, and combinations thereof. In specific embodiments, the metal component comprises a ceramic or metal oxide selected from the group consisting of $Al_2O_3$, $ZrO_2$, $Fe_2O_3$, CuO, NiO, ZnO, CdO, C, Ge, Si, $SiO_2$, $TiO_2$, $V_2O_5$, $VO_2$, $Fe_3O_4$, SnO, $SnO_2$, CoO, $CoO_2$, $Co_3O_4$, $HfO_2$, $BaTiO_3$, $SrTiO_3$, and $BaSrTiO_3$. In further or alternative embodiments, the nanofibers comprise a metal-non-metal alloy. In further or alternative embodiments, the nanofibers comprise a conductive material, wherein the nanofibers have a conductivity of at least about 10% (e.g., on average) when compared with the conductivity of the conductive material when formed into a sheet. In further or alternative embodiments, the nanofibers comprise a continuous matrix of amorphous ceramic and comprise an ultimate strength-to-diameter ratio of at least 0.075 MPa/nm (e.g., on average); a Young's modulus-to-diameter ratio of at least 0.15 GPa/nm (e.g., on average); and a fracture toughness of at least 0.6 MPA MPa·m$^{1/2}$ (e.g., on average). In further or alternative embodiments, the nanofibers comprise a continuous matrix of amorphous ceramic and comprise an ultimate strength-to-diameter ratio of at least 0.15 MPa/nm (e.g., on average);

an Young's modulus-to-diameter ratio of at least 0.3 GPa/nm (e.g., on average); and a fracture toughness of at least 0.7 MPa·m$^{1/2}$ (e.g., on average). In some embodiments, the nanofibers comprise a continuous matrix of crystalline ceramic and comprise an ultimate strength-to-diameter ratio of at least 5 MPa/nm (e.g., on average); and a Young's modulus-to-diameter ratio of at least 1.5 GPa/nm (e.g., on average). In some embodiments, the nanofibers comprise a continuous matrix of crystalline ceramic and comprise an ultimate strength-to-diameter ratio of at least 12.5 MPa/nm (e.g., on average) and a Young's modulus-to-diameter ratio of at least 4 GPa/nm (e.g., on average). In further or alternative embodiments, the nanofibers have a fracture toughness of at least 1.8 MPa·m$^{1/2}$ (e.g., on average). In some embodiments, the nanofibers comprise a continuous matrix of metal and have an ultimate strength-to-diameter ratio of at least 0.35 MPa/nm (e.g., on average) and a Young's modulus-to-diameter ratio of at least 1.1 GPa/nm (e.g., on average). In some embodiments, the nanofibers comprise a continuous matrix of metal and have an ultimate strength-to-diameter ratio of at least 0.9 MPa/nm (e.g., on average) and a Young's modulus-to-diameter ratio of at least 2.9 GPa/nm (e.g., on average). In further or alternative embodiments, the nanofibers have an fracture toughness of at least 3.5 MPa·m$^{1/2}$ (e.g., on average). In further or alternative embodiments, the nanofibers have a log(S/m) to log(S/m) ratio with an identical bulk material of at least 0.8 (e.g., at least 0.9) (e.g., on average). In further or alternative embodiments, the nanofibers have a length of at least 50 microns (e.g., on average). In further or alternative embodiments, the nanofibers have a diameter of 500 nm or less (e.g., on average). In further or alternative embodiments, the nanofibers have an aspect ratio of at least 1000 (e.g., on average). In further or alternative embodiments, the nanofibers comprise less than 5% (e.g., less than 3%, or less than 1%) carbon by elemental mass (e.g., on average). In further or alternative embodiments, the nanofibers have (e.g., on average) less than 100 defects (e.g., less than 50, less than 10, or less than 5) per linear mm of nanofiber.

In some embodiments, the nanofibers described herein are used in a sensor, a battery, a fuel cell, a solar cell, ultracapacitor, catalyst, membrane, or electrode.

Described herein are hybrid nanofibers including hollow nanofibers and multi-axial nanofibers comprising more than one material. Provided herein are high quality nanofibers and processes of preparing high quality nanofibers that are suitable for applications such as electrochemical devices (e.g., batteries and solar cells), advanced filtration, catalysis, and the like. In some instances, the nanofibers provided and/or prepared according the processes described herein are prepared at costs low enough to be commercially viable. The present disclosure includes hybrid and hollow nanofibers, use of nanofibers in many types of applications, devices incorporating nanofibers, the use of devices incorporating nanofibers, and the like.

In one aspect, described herein is a process for producing a nanofiber. In some embodiments, the process includes electrospinning a fluid stock. The fluid stock comprises metal and/or ceramic precursor and polymer. In one embodiment, the weight to weight ratio of the precursor to polymer is at least 1:2. In some embodiments, the polymer is water soluble.

In another aspect, described herein is a process for producing nanofibers, the process comprising electrospinning a fluid stock, the fluid stock comprising metal precursor(s) and polymer. In some embodiments, the fluid stock is (1) a solution; (2) a substantially uniform dispersion (e.g., of the precursor(s)); or (3) a substantially homogenous dispersion (e.g., of the precursor(s)).

In one aspect, described herein is a method for producing a nanofiber, the method comprising electrospinning a first fluid with a second fluid, at least one of the first or second fluids being an aqueous fluid. In some embodiments, the first and second fluids are electrospun about the same or similar axis. In some embodiments, the first fluid is an aqueous fluid comprising water, a water soluble polymer, and metal precursor. In some embodiments, the second fluid is a second aqueous fluid, comprising water, a water soluble polymer, and a second metal and/or ceramic precursor, wherein the water soluble polymer of the second fluid is the same or different than the water soluble polymer of the first fluid.

In one aspect, described herein is a method for producing a nanofiber, the method comprising multi-axially electrospinning an aqueous fluid stock and a second fluid. In some embodiments, the aqueous fluid stock comprises water, a water soluble polymer, and metal and/or ceramic precursor. In some embodiments, the second fluid is a second aqueous fluid stock. In some embodiments, the second fluid is a gas. In some embodiments, the second fluid at least partially surrounds the aqueous fluid stock. In some embodiments, the aqueous fluid stock at least partially surrounds the second fluid.

In one aspect, described herein is a process for producing a nanofiber, the process comprising electrospinning a fluid stock comprising metal precursor, ceramic precursor, or combination thereof wherein: (a) the fluid stock is aqueous; (b) the concentration of the precursor in the fluid stock is at least 200 mM; or both (a) and (b).

In some embodiments, the fluid stock further comprises a water-soluble polymer. In some embodiments, the precursor binds to the water-soluble polymer. In some embodiments, the electrospinning step comprises multi-axially electrospinning the fluid stock with a gas or a second fluid stock. In some embodiments, the fluid stock comprises a non-aqueous solvent. In some embodiments, the fluid stock comprises tetrahydrofuran (THF) and polystyrene (PS).

In one aspect, described herein is a process of producing a nanofiber, the process comprising electrospinning a fluid stock into an electrospun material, the fluid stock comprising polymer and precursor, the precursor comprising (i) metal precursor, (ii) ceramic precursor, or (iii) a combination thereof, and: (a) the weight to weight ratio of the precursor to polymer being at least 1:2; (b) the fluid stock is (1) a solution; (2) a substantially uniform dispersion; or (3) a substantially homogenous dispersion; (c) the concentration of the precursor in the fluid stock is at least 200 mM; or (d) a combination thereof.

In some embodiments, the fluid stock is an aqueous fluid stock.

In some embodiments, the process further comprises removing the polymer from the electrospun material.

In some embodiments, the process further comprises calcination of the precursor to metal, metal oxide, metal alloy, ceramic, or a combination thereof.

In some embodiments, calcination of the metal and/or ceramic precursor(s) is performed under inert, oxidative, or reductive conditions.

In some embodiments, the metal is selected from the group consisting of Ag, Cu, Ni, Fe, Co, Pb, Au, Sn, and Al.

In some embodiments, the ceramic or metal oxide is selected from the group consisting of $Al_2O_3$, $ZrO_2$, $Fe_2O_3$, CuO, NiO, ZnO, CdO, C, Ge, Si, $SiO_2$, $TiO_2$, $V_2O_5$, $VO_2$, $Fe_3O_4$, SnO, $SnO_2$, CoO, $CoO_2$, $Co_3O_4$, $HfO_2$, $BaTiO_3$, $SrTiO_3$, and $BaSrTiO_3$.

In some embodiments, the fluid stock comprises the precursor associated with the polymer by covalent or non-covalent interactions.

In some embodiments, the association of the precursor with the polymer provides a fluid stock comprising precursor uniformly dispersed therein.

In some embodiments, the polymer and precursor taken together comprise about 1 weight % to about 20 weight % of the fluid stock.

In some embodiments, the metal precursor comprises a metal-ligand complex.

In some embodiments, the metal-ligand complex is a metal acetate, metal nitrate, metal chloride, or metal alkoxoxide.

In some embodiments, the polymer is a thermally degradable or chemically degradable polymer.

In some embodiments, the polymer is polyvinyl alcohol, polyvinyl acetate, polyvinyl ether, polyvinyl pyrrolidone, polyglycolic acid, polyethylene oxide, hydroxyethylcellulose (HEC), ethylcellulose, cellulose ethers, polyacrylic acid, polyisocyanate, or any combination thereof.

In some embodiments, the process of electrospinning the fluid stock comprises electrospinning the fluid stock with a second fluid stock about the same or similar axis to produce a layered nanofiber.

In one aspect, described herein is a nanofiber comprising a metal, a metal oxide, a metal alloy, a ceramic, a metal precursor, a ceramic precursor or a combination thereof, and: (a) the nanofiber is at least 1 µm (e.g., at least 50 µm) long on average; (b) the nanofiber has an aspect ratio of at least about 5 (e.g., at least 10, at least 100, at least 1000, or the like); (c) the nanofiber comprises a segment comprising a continuous matrix of a metal, a metal oxide, a metal alloy, a ceramic, or a combination thereof; (d) the nanofiber has a specific surface area between 1 $m^2$/g and about 1000 $m^2$/g; or (e) a combination thereof. In some embodiments, the nanofiber comprises at least 33% (w/w) of a metal, a metal oxide, a metal alloy, a ceramic, a metal precursor, a ceramic precursor or a combination thereof.

In some embodiments, the metal is selected from the group consisting of Ag, Cu, Ni, Fe, Co, Pb, Au, Sn, and Al.

In some embodiments, the ceramic or metal oxide is selected from the group consisting of $Al_2O_3$, $ZrO_2$, $Fe_2O_3$, CuO, NiO, ZnO, CdO, C, Ge, Si, $SiO_2$, $TiO_2$, $V_2O_5$, $VO_2$, $Fe_3O_4$, SnO, $SnO_2$, CoO, $CoO_2$, $Co_3O_4$, $HfO_2$, $BaTiO_3$, $SrTiO_3$, and $BaSrTiO_3$.

In some embodiments, the nanofiber comprises a conductive material, wherein the nanofiber has an conductivity of at least about 10% when compared with the conductivity of the conductive material when formed into a sheet.

In one aspect, described herein is a process for producing a nanofiber, the process comprising electrospinning about the same or similar axis a first fluid stock with a second fluid stock, the first fluid stock being aqueous and comprising a first polymer.

In some embodiments, the first polymer is water soluble.

In some embodiments, the second fluid is aqueous.

In some embodiments, the second fluid stock comprises a second polymer, and the first and second polymers are optionally the same.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 44 illustrates a TEM image of tri-axial nanofibers of $SiO_2$ (core)/PI-b-PS with $Fe_3O_4$ (middle)/$SiO_2$ (sheath).

FIG. 45 illustrates a cross-sectional view of an electrolytic double layer ultracapacitor.

FIG. 46 illustrates a cross-sectional view of barium titanate nanofibers laid on the activated carbon of an ultracapacitor.

DETAILED DESCRIPTION OF THE INVENTION

Figure 1:
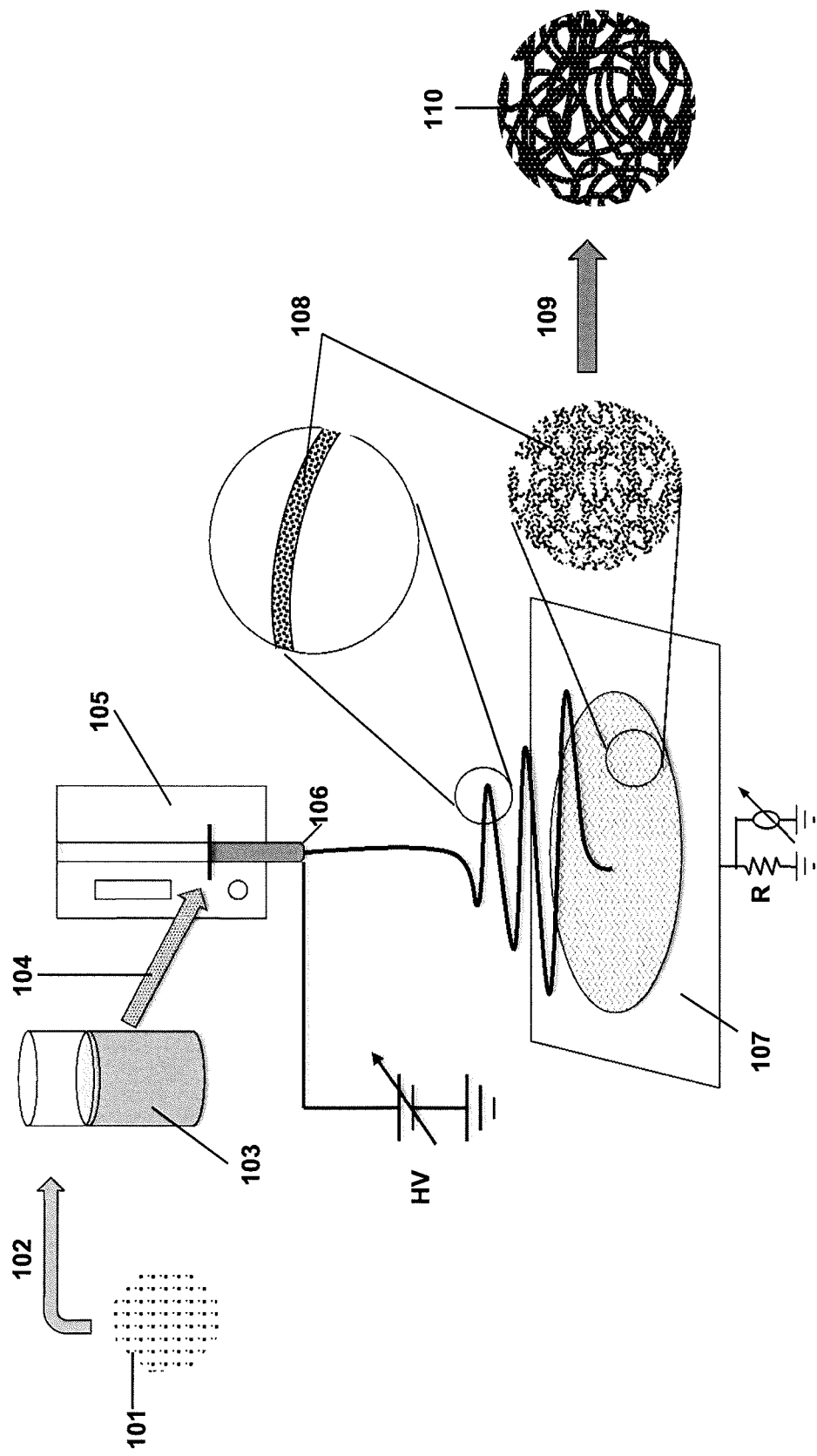
FIG. 1 illustrates a schematic of the process and system of the disclosure.

Nanotechnology is the manipulation of matter at an atomic and molecular scale and is a diverse field involving many different structures, techniques and potential applications. Of them, one structure is a nanofiber, which generally has a diameter of less than 5,000 nm and has various lengths. There is a need for high quality nanofibers, such as metal nanofibers, ceramic nanofibers, hybrid nanofibers, and the like. Such nanofibers and processes for preparing such nanofibers are provided in certain embodiments herein. In some embodiments, provided herein are high quality nanofibers that have good structural integrity, few voids, few structural defects, tunable length, and the like. In some embodiments, the present disclosure includes methods for making long, high quality nanofibers.

In some embodiments, methods provided herein use a fluid stock comprising a precursor and a polymer that interact with each other and/or are compatible with each other such that the polymer facilitates solubilization (e.g., dissolution, dispersion, or the like) of the precursor. In one aspect, provided herein is a nanofiber (e.g., a precursor nanofiber) comprising a polymer and a precursor. In another aspect, provided herein is a nanofiber comprising a metal component (e.g., a metal, such as a single metal or a metal alloy, a metal oxide, such as a metal oxide, a ceramic, or the like). In a specific aspect, provided herein is a continuous matrix metal component nanofiber. In a more specific aspect, provided herein is a nanofiber comprising a segment comprising a continuous matrix of a metal, a metal oxide, a metal alloy, a ceramic, or a combination thereof.

In some embodiments, provided herein is a process for the conversion of electrospun fluid stock (e.g., a precursor nanofiber comprising a polymer and a precursor) to a nanofiber, wherein the polymer is removed. In some instances, this process, leaves defects such as gaps, voids, and the like in the resultant nanofiber. In some embodiments, these defects are reduced by increasing the proportion of a metal or ceramic precursor in the fluid stock relative to the amount of polymer.

In some embodiments, ensuring that the fluid stock is homogenous reduces the voids and/or defects in the nanofiber compared to when the fluid stock is not homogenous. In some instances, when the fluid feed is electrospun and converted to a nanofiber, use of homogenous fluid feed leads to a homogenous nanofiber. In some embodiments, provided herein are methods for creating homogenous fluid stocks. In some embodiments, the precursor is solubilized by associating the precursor with a ligand. In some embodiments, the polymer is water soluble. In some instances, water-based (aqueous) fluid stocks are advantageous over fluid stocks based on other solvents (e.g., where a non-aqueous solvent is toxic). In some embodiments, it is advantageous to perform the process in an aqueous environment.

In some embodiments, associating the precursor with the polymer, such as through a chemical bond between the precursor and polymer results in long, high quality nanofibers with few defects compared to embodiments without an association between the precursor and polymer. In some instances, the precursor is distributed relatively homogenously on the polymer (e.g., such that electrospinning of the fluid stock having such homogenous associations provides nanofibers with few voids and defects). In addition to the association, it is advantageous in some embodiments to first create a homogenous solution of precursor before combining the precursor and polymer.

In some embodiments, the increased proportion of precursor and homogenous distribution of the precursor to create high quality nanofibers results in nanofibers with complex geometries or advanced properties. These geometries include long hollow nanofibers and nanofibers that are hybrids of more than one material. In various embodiments, these materials are without limitation, metals, ceramics, or combinations thereof.

Process

Described herein is a process of producing a nanofiber. In some embodiments, the process includes electrospinning a fluid stock. In specific embodiments, the fluid stock comprises metal precursor (e.g., a precursor comprising a metal-ligand compound that, depending on downstream treatment can be converted into a metal, a metal oxide, a ceramic, or the like) and polymer. In specific embodiments, the metal precursor and polymer are present in a precursor-polymer association. In certain embodiments, the weight to weight ratio of the precursor to polymer is at least 1:2. In specific embodiments, the weight to weight ratio of the precursor to polymer is over 1:2. In more specific embodiments, the wt. precursor to wt. polymer ratio is at least 1:1. In still more specific embodiments, the wt. precursor to wt. polymer ratio is over 1:1. In some embodiments, the polymer is water soluble (e.g., completely dissolvable in water, or at least swellable in water). In specific embodiments, the fluid stock is aqueous (i.e., comprising water). In certain embodiments, the precursor (e.g., as measured by the metal component of the precursor) is at least 200 mM in the fluid stock.

In some embodiments, provided herein is a process of electrospinning a fluid stock, the fluid stock comprises metal precursor and polymer, the weight-to-weight ratio of the precursor to polymer of over 1:2 (e.g., at least 1:1.75). In certain embodiments, the fluid stock is prepared by combining precursor and polymer in a weight-to-weight ratio of over 1:2 (e.g., at least 1:1.75). In specific embodiments, the fluid stock is aqueous. In more specific embodiments, the metal precursor and polymer are present in the fluid stock in a precursor-polymer association.

In some embodiments, a process described herein comprises associating or binding a metal to a solubilizing ligand to produce a first metal precursor, optionally in an aqueous solution. In some embodiments, the precursor solution is mixed to provide a homogenous precursor composition (e.g., solution). In some embodiments, the precursor composition is then combined with a composition of polymer (e.g., water-soluble polymer) to provide a fluid stock.

In some embodiments, the (first) precursor molecules associate with, or bind to (which terms are understood to be used interchangeably herein—reference to association or binding indicates formation of a covalent bond, a metal-ligand complex, an ionic bond, a Lewis base/Lewis acid interaction, or the like), the polymer (e.g., to provide a precursor-polymer association—a polymer+a second metal precursor).

In some embodiments, the fluid stock is mixed to provide a homogeneous fluid stock, where the precursor is optionally associated with the polymer substantially evenly (e.g., as determined by measuring the variation of viscosity in the composition). In some embodiments, the fluid stock is then electrospun into an electrospun fluid stock. In some instances, the electrospun fluid stock is then calcinated, optionally by heating. In some embodiments, heating in a reducing environment results in a pure metal nanofiber and heating in an oxidizing environment leads to a ceramic nanofiber.

In certain embodiments, the polymer is a nucleophilic polymer (e.g., a polymer comprising alcohol groups, such as PVA). In some embodiments, the polymer is a nucleophilic polymer and a first precursor (e.g., reagent precursor) is an electrophilic precursor (e.g., a metal acetate, metal chloride, or the like). In specific embodiments, the precursor-polymer association is a reaction product between a nucleophilic polymer and an electrophilic first precursor (e.g., reagent precursor).

In other embodiments, the polymer is an electrophilic polymer (e.g., a polymer comprising chloride or bromide groups, such as polyvinyl chloride). In some embodiments, the polymer is an electrophilic polymer and a first precursor (e.g., reagent precursor) is a nucleophilic precursor (e.g., metal-ligand complex comprising "ligands" with nucleophilic groups, such as alcohols or amines). In specific embodiments, the precursor-polymer association is a reaction product between an electrophilic polymer and a nucleophilic first precursor.

Figure 2B:
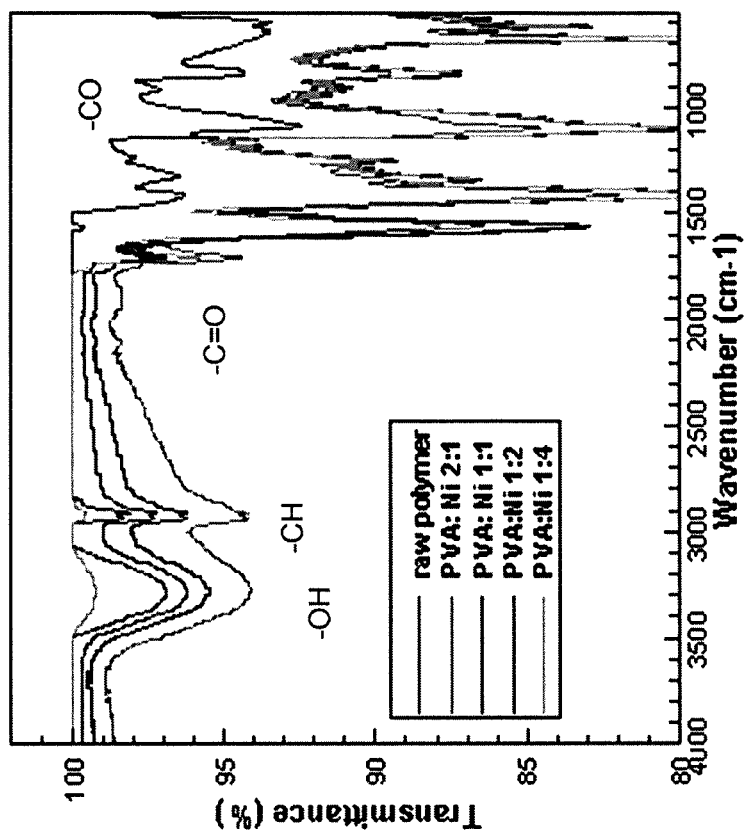
FIG. 2B illustrates an FTIR study of the effect of Ni precursor loading on the saturation of —OH bonds in PVA.

In some embodiments, the fluid stock comprises a high loading of precursor. In specific embodiments, the fluid stock comprises a high loading of the precursor on the polymer and/or associations between the precursor and polymer. In specific embodiments, the polymer has a precursor loading of at least 20% (i.e., at least 20% of the reactive sites of the polymer—nucleophilic or electrophilic sites—are associated with a metal compound; this is also described herein as being at least 20% saturated with precursor). As discussed herein, when taken together, the polymer loaded with metal precursor form (i) a composition comprising a polymer and a metal precursor and (ii) a polymer-precursor association. In more specific embodiments, the polymer has a loading of at least 35%. In still more specific embodiments, the polymer has a loading of at least 50%. In yet more specific embodiments, the polymer has a loading of at least 75%. Loading can be determined by any suitable mechanism, e.g., nuclear magnetic resonance (NMR) spectrometry, infrared (IR) spectrometry, or the like. For example, FIG. 2B illustrates the increased loading of precursor on the polymer (e.g., by the decreasing intensity of the —OH peak).

In some instances, the methods for creating a homogenous fluid stock are used to produce structures with geometries other than nanofibers (e.g., nanoparticles, spheres, meshes, thin films, nano-robotic parts such as a gear). As with nanofibers, it is desirable in some embodiments to make these structures with few defects, so are suitable applications of the present disclosure. In one aspect, the present invention includes pure metal, ceramic, or hybrid nanostructures including spheres, meshes, gears and the like.

In some embodiments, the process comprises electrospinning a fluid stock. Any suitable method for electrospinning is used. In some instances, elevated temperature electrospinning is utilized. Exemplary methods for comprise methods for electrospinning at elevated temperatures as disclosed in U.S. Pat. Nos. 7,326,043 and 7,901,610, which are incorporated herein for such disclosure. In some embodiments, elevated temperature electrospinning improves the homogeneity of the fluid stock throughout the electrospinning process. In some embodiments, gas assisted electrospinning is utilized (e.g., about a common axis with the jet electrospun from a fluid stock described herein). Exemplary methods of gas-assisted electrospinning are described in PCT Patent Application PCT/US2011/024894 ("Electrospinning apparatus and nanofibers produced therefrom"), which is incorporated herein for such disclosure. In gas-assisted embodiments, the gas is optionally air or any other suitable gas (such as an inert gas, oxidizing gas, or reducing gas). In some embodiments, gas assistance increases the throughput of the process and/or reduces the diameter of the nanofibers. In some instances, gas assisted electrospinning accelerates and elongates the jet of fluid stock emanating from the electrospinner. In some embodiments, incorporating a gas stream inside a fluid stock produces hollow nanofibers. In some embodiments, the fluid stock is electrospun using any method known to those skilled in the art.

In some embodiments, nanofibers are produced from an aqueous fluid stock (e.g., comprising water, a water soluble polymer and metal and/or ceramic precursor). In some instances, aqueous fluid stocks are cheaper, more environmentally friendly, avoid the use of organic solvents and/or have other advantages in certain applications. In addition, in certain aspects, the use of aqueous fluid stocks allows for higher loading of both polymers and precursors. In some instances, higher precursor loading provides for metal, metal oxide, and ceramic nanofibers that have good structural integrity, reduced void structures, and/or reduced structural defects.

In specific embodiments, the use of aqueous fluid stocks is combined with coaxial electrospinning (electrospinning two or more fluids about a common axis). As described herein, coaxial electrospinning with a second fluid is used to add coatings, make hollow nanofibers, make nanofibers comprising more than one material, and the like. In various embodiments, the second fluid is either outside (i.e., at least partially surrounding) or inside (e.g., at least partially surrounded by) the aqueous (first) fluid stock. In some embodiments, the second fluid is a gas (gas-assisted electrospinning). As described herein, in some embodiments, gas assistance increases the throughput of the process, reduces the diameter of the nanofibers, and/or is used to produce hollow nanofibers. In some embodiments, the method for producing nanofibers comprises coaxially electrospinning an aqueous fluid stock and a gas. In other embodiments, the second fluid is a second fluid stock having the characteristics as described herein (i.e., comprising a polymer and precursor according to the instant disclosure). In some embodiments where at least two fluid stocks according to the instant disclosure are coaxial electrospun according to a method described herein, a hybrid nanofiber comprising a core and at least one layer thereon is formed.

In one aspect, described herein is a method for producing a nanofiber, the method comprising electrospinning a first fluid with a second fluid, at least one of the first or second fluids being an aqueous fluid. In various embodiments, the first fluid and second fluid are positioned relative to each other in any suitable orientation and/or shape. In some embodiments, the first fluid and second fluids are next two each other as they exit the electrospinner. In some embodiments, one of either the first fluid or second fluid surrounds the other. In some embodiments, the first and second fluids are electrospun about the same or similar axis.

In some embodiments, the first fluid is an aqueous fluid comprising water, a water soluble polymer, and metal and/or ceramic precursor. In some embodiments, the second fluid is a second aqueous fluid, comprising water, a water soluble polymer, and a second metal and/or ceramic precursor, wherein the water soluble polymer of the second fluid is the same or different than the water soluble polymer of the first fluid.

In some embodiments, the method includes "co-axially" electrospinning, producing "co-axial" hybrid nanofibers, and such. As used herein, co-axial refers to concentric cylinders of material that have a common (the same) center axis (e.g., a cylindrical nanofiber with a core material surrounded by one or more coatings or cylindrical layers). Co-axial nanofibers are hollow in some embodiments. There is no limit to the number of layers of material (i.e., co-axial does not imply two layers). The terms "co-axial" and "multi-axial" are used interchangeably. Multi-axial electrospinning refers to electrospinning multiple fluids (e.g., multiple fluid stocks as described herein and/or one or more gas) about a common axis.

In some instances, the use of metal precursors increases the electrical conductivity, which may lead to more vigorous whipping of the electrospinning filament. Increasing the electrical conductivity of the fluid stock through choice of precursor for example, may also increase the productivity of the process in some instances. In some instances, increased productivity is achieved by increasing the conductivity of the fluid stock. In certain instances, increased conductivity causes more repulsion by the jets emanating from adjacent spinnerets. In some instances, the jets are less likely to touch each other prematurely because of this increased repulsion, which allows the practitioner to space the spinnerets more closely together. More closely spaced spinnerets generally results into increased overall productivity (as long as the productivity per spinneret is not substantially reduced).

The electrospinning process described herein comprises dispersing and/or keeping the fluid stock relatively evenly dispersed (e.g., uniformly dispersed or homogenously dispersed). In some embodiments, to achieve or maintain dispersion, the fluid stock is heated, especially if the fluid stock solidifies at ambient temperature. In some embodiments, the fluid stock is agitated, optionally in combination with heating. Agitation includes but is not limited to stirring, mixing, sonicating, vortexing, and the like and creates or maintains a substantially homogenous fluid stock. In some instances, the fluid stock is stirred continuously during the electrospinning process. In one particular embodiment, the fluid stock is stirred for about an hour to get a homogenous dispersion.

In some embodiments, the procedure for forming the nanofiber is not electrospinning. Electrospinning is but one method of producing nanofibers. Other suitable methods include the sol-gel technique or interfacial polymerization or "fast mixing" techniques (Huang, Pure Appl. Chem., Vol. 78, No. 1, pp. 15-27, 2006). The present disclosure further includes methods for making nano-geometries other than fibers such as for making nano-spheres by electrospraying. The composition of the fluid stock and methods for making same are agnostic to the particular geometry (i.e., are applicable to any geometry) and method for producing the geometry.

In some examples, high loading of precursor on the polymer in the fluid stock is beneficial for obtaining pure and/or uniform nanofibers. As described herein, few defects and/or voids are created in the nanofiber when the polymer is removed compared to the number of defects and/or voids created when having lower precursor loading. Loading is represented as the weight ratio of the precursor to polymer in or combined to form the fluid stock. The weight ratio of the precursor to polymer is any value resulting in a nanofiber with suitable properties in a given embodiment. The weight ratio of the precursor to polymer is at least 1:2 in some embodiments. In some embodiments, there is more precursor than polymer by weight. In some embodiments, the weight ratio of the precursor to polymer is at least 1.25:1, at least 1.5:1, at least 1.75:1, at least 2:1, at least 3:1, at least 4:1, at least 5:1, at least 6:1, at least 7:1, at least 8:1, at least 9:1, at least 10:1, at least 15:1, at least 20:1, at least 30:1, at least 40:1, at least 50:1, or at least 100:1. In some embodiments, the weight ratio of the precursor to polymer is about 1.25:1, about 1.5:1, about 1.75:1, about 2:1, about 3:1, about 4:1, about 5:1, about 6:1, about 7:1, about 8:1, about 9:1 about 10:1, about 15:1, about 20:1, about 30:1, about 40:1, about 50:1, or about 100:1. In yet other embodiments, the weight ratio of precursor to polymer is between about 1:2 and 10:1, between 1:1 and 4:1, between about 2:1 and 10:1, or between about 3:1 and 8:1. In specific embodiments, if the polymer and precursor present in the fluid stock are present in the form of a polymer-precursor association, the weight ratio is determined by comparing the unassociated, unreacted theoretical weights of the polymer and the precursor (e.g., a first precursor that is reacted with the polymer, such as a metal acetate). In some embodiments, a process described herein comprises preparing and/or using a fluid stock that is prepared by combining precursor with a polymer and, optionally, a fluid (e.g., water, or water containing fluid—an aqueous fluid) and the precursor/polymer weight-to-weight ratio is determined by the amount of precursor (e.g., a first precursor) combined with a polymer (e.g., a polymer not associated with a precursor). For example, if the fluid stock is prepared with x grams of a precursor (e.g., a first precursor) and y grams of polymer, the precursor/polymer weight-to-weight ratio is x:y (e.g., regardless of whether or not the precursor ultimately associates with the polymer in the stock). In some embodiments, upon combination of a precursor (e.g., a first precursor, such as $ML_b$, wherein M is a metal and L is one or more ligand as described herein, and b is a suitable number, such as 1-10) with a polymer (P), a polymer-precursor association is formed (e.g., $P-ML_{b-1}$, $ML_{b-1}$ being a second precursor in association with the polymer). In some of such instances, all or part of the first precursor is associated with the polymer and the precursor/polymer weight-to-weight ratio is determined by the ratio of the sum of the first and second precursors to the polymer.

Figure 2A:
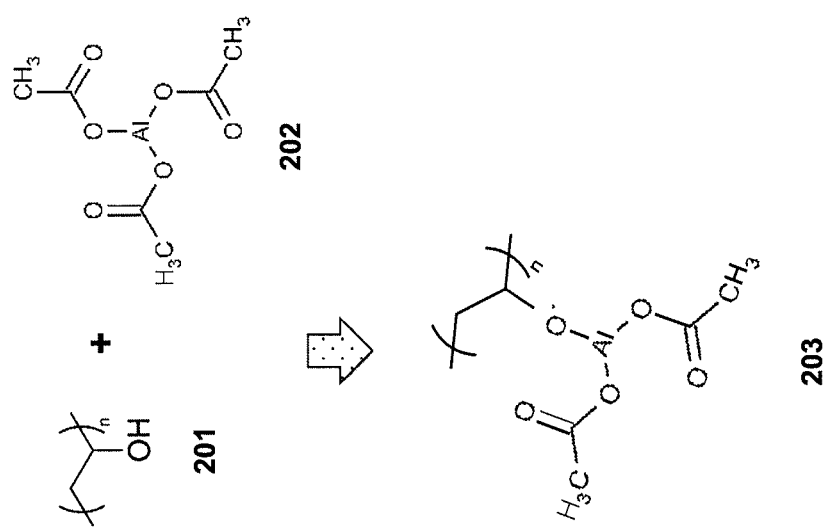
FIG. 2A illustrates an exemplary mechanism of precursor-polymer bonding.

In some embodiments, a process provided herein comprises: (a) preparing a fluid stock by combining a first metal precursor, a polymer, and a fluid (e.g., aqueous fluid), the first fluid precursor being combined with the polymer in a weight-to-weight ratio of at least 1:2; and (b) electrospinning a fluid stock. In other embodiments, a process provided herein comprises electrospinning a fluid stock prepared by combining a first metal precursor, a polymer, and a fluid (e.g., aqueous fluid), the first metal precursor being combined with the polymer in a weight-to-weight ratio of at least 1:2. In specific embodiments, upon combination of the metal precursor and the polymer, at least a portion of the first metal precursor associates with the polymer to form a polymer-precursor association, the polymer-precursor association comprising a polymer and a second metal precursor (i.e., a residual component of the first metal precursor). For example, FIG. 2A illustrates a first precursor of $Al(OCOCH_3)_3$ reacting with a polymer to form a polymer-precursor association comprising a polymer (polyvinyl alcohol) in association with a second precursor of $Al(OCOCH_3)_2$. In specific embodiments, the weight to weight ratio of the first precursor to polymer is over 1:2. In more specific embodiments, the wt. first precursor to wt. polymer ratio is at least 1:1. In still more specific embodiments, the wt. first precursor to wt. polymer ratio is over 1:1.

In some embodiments, the fluid stock includes metal and/or ceramic precursor and polymer. In some embodiments, the nanofiber comprises metal or ceramic precursor and polymer. In some embodiments, the precursor and/or nanofiber is not metal and/or ceramic. The methods described herein are used to make nano-structures that have few voids or defects in some instances (e.g., no matter the material). The methods for making a substantially uniform fluid feed described herein (e.g., by associating precursor substantially uniformly on a polymer) are applicable to materials other than metals and/or ceramics.

FIG. 1 illustrates an exemplary schematic of a process described herein. In some instances, a first composition comprising metal precursor 101 (e.g., an acetate of Ag, Al, Co, Fe, Ni, Zn, Zr, Si, etc.) is combined 102 with a second composition comprising a polymer 103 (e.g., PVA, PVAc, PVEO, etc.) to prepare a fluid stock comprising a fluid stock composition 104. In some instances, a fluid stock provided herein is electrospun using, e.g., a syringe system 105, through a nozzle 106, wherein the nozzle is optionally heated. In certain embodiments, electrospinning of the fluid stock produces a precursor nanofiber 108, comprising metal precursor and polymer (e.g., in a weight ratio of over 1:2 and up to 4:1), the precursor nanofiber being collected on a collector 107. Treatment 109 (e.g., thermal and/or chemical treatment) of the precursor nanofiber 108 may then be performed to produce ceramic, metal, or composite nanofibers (e.g., pure ceramic, metal, or composite nanofibers) 110.

Figure 34:
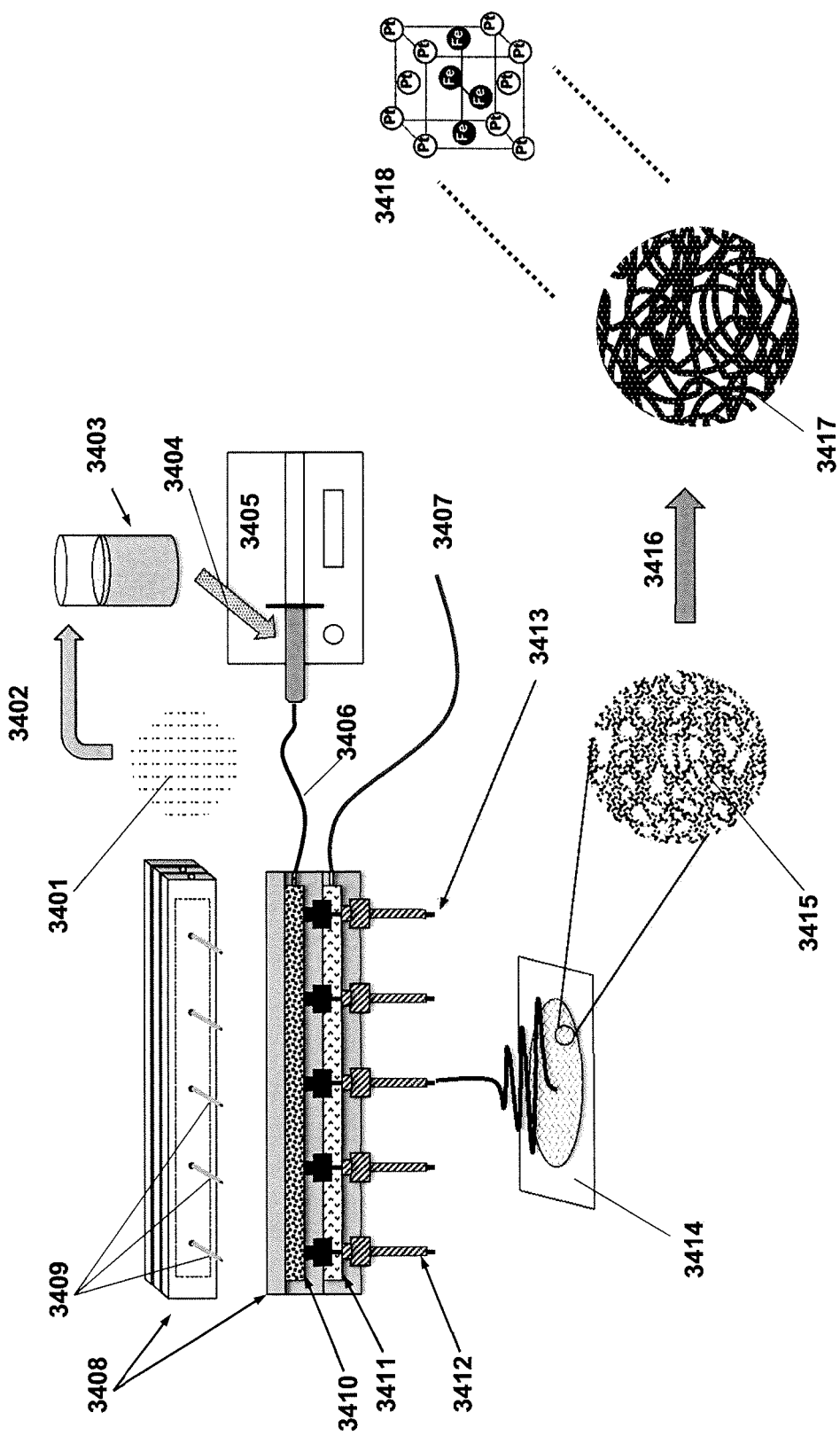
FIG. 34 illustrates a schematic of the process and system for producing Fe/Pt nanofibers suitable for use in fuel cells.

FIG. 34 illustrates another exemplary schematic of a process described herein. In some instances, a first composition comprising metal precursor 3401 (e.g., an acetate of Ag, Al, Co, Fe, Ni, Zn, Zr, Si, etc.) is combined 3402 with a second composition comprising a polymer 3403 (e.g., PVA, PVAc, PEO, etc.) to prepare a fluid stock comprising a fluid stock composition 3404. In some instances, a fluid stock is provided 3406 to an apparatus 3408 comprising a plurality of electrospinning nozzles/needles 3409. In certain embodiments, the fluid stock is electrospun with another fluid 3407 (e.g., via connection to an air pump) that is also provided to the apparatus 3409. In some instances, apparatus 3409 comprises a fluid stock chamber 3410 and a second fluid chamber (e.g., high pressure gas chamber) 3411. Electrospinning of the fluid stock may then be electrospun from a center needle or nozzle (e.g., aligned along a longitudinal axis) 3413 while a second fluid is being coaxially expressed from an outer needle or nozzle (e.g., aligned along the same longitudinal axis) 3412. In specific instances, the fluid stock nozzle (needle) 3413 is optionally heated. In some instances, e.g., where hollow nanofibers are desired, the gas and fluid stock chambers and needles may be switched (see, e.g., FIG. 35). In certain embodiments, electrospinning of the fluid stock produces a precursor nanofiber 3415, comprising metal precursor and polymer (e.g., in a weight ratio of over 1:2 and up to 4:1), the precursor nanofiber being collected on a collector 3414. Treatment 3416 (e.g., thermal and/or chemical treatment) of the precursor nanofiber 3415 may then be performed to produce ceramic, metal, or composite nanofibers (e.g., pure ceramic, metal, or composite nanofibers) 3417. In specific embodiments, the metal nanofiber may be a metal alloy nanofiber, such as a platinum-iron alloy 3418.

Figure 35:
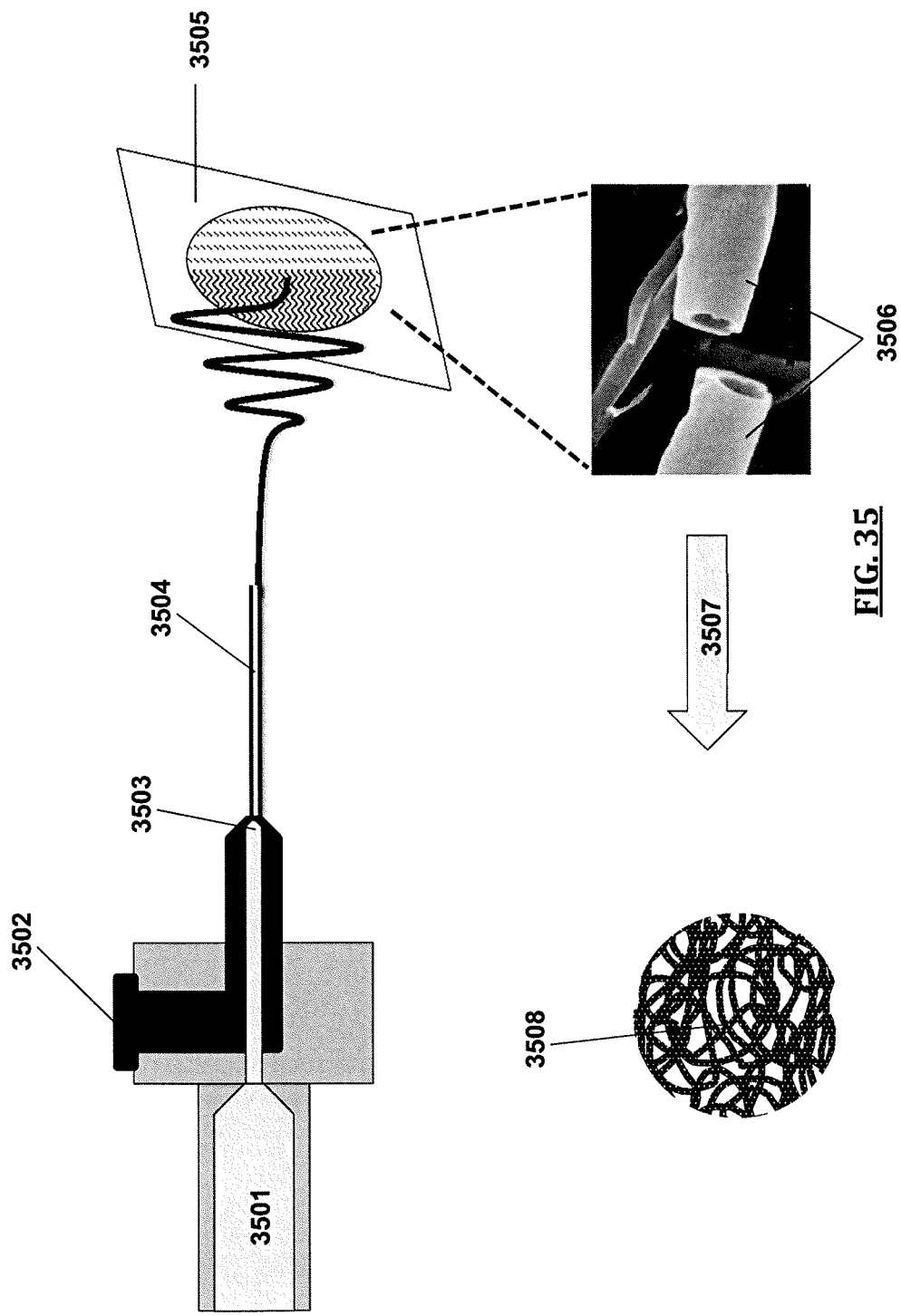
FIG. 35 illustrates a schematic of the process and system for producing hollow Si or Ge nanofibers suitable for use in lithium ion batteries and a micrograph of hollow Si or Ge electrospun fluid stock.

FIG. 35 illustrates an exemplary schematic of a process for preparing hollow (i.e., hollow core) metal, metal oxide, or ceramic nanofibers described herein. In some instances, a fluid stock is provided to a fluid stock chamber 3502 of an apparatus described herein. In some instances, the fluid stock chamber comprises a supply end and a nozzle end, out of which the fluid stock is electrospun with the assistance of gas, which is provided via a gas chamber 3501 comprising a supply end and a nozzle end, the nozzle end being positioned coaxially (i.e., along substantially the same longitudinal axis) with the nozzle end of the fluid stock chamber 3503. In some embodiments, coaxial electrospinning of the fluid stock with the gas in such a manner produces a hollow precursor nanofiber 3506, which may be collected on a collector 3505. The hollow precursor nanofibers comprising metal precursor and polymer is illustrated 3506 in FIG. 35. In some instances, these hollow precursor nanofibers are then treated 3507 (e.g., thermally) to produce hollow metal nanofibers 3508. Exemplary hollow nanofibers include hollow Si or Ge nanofibers.

Figure 36:
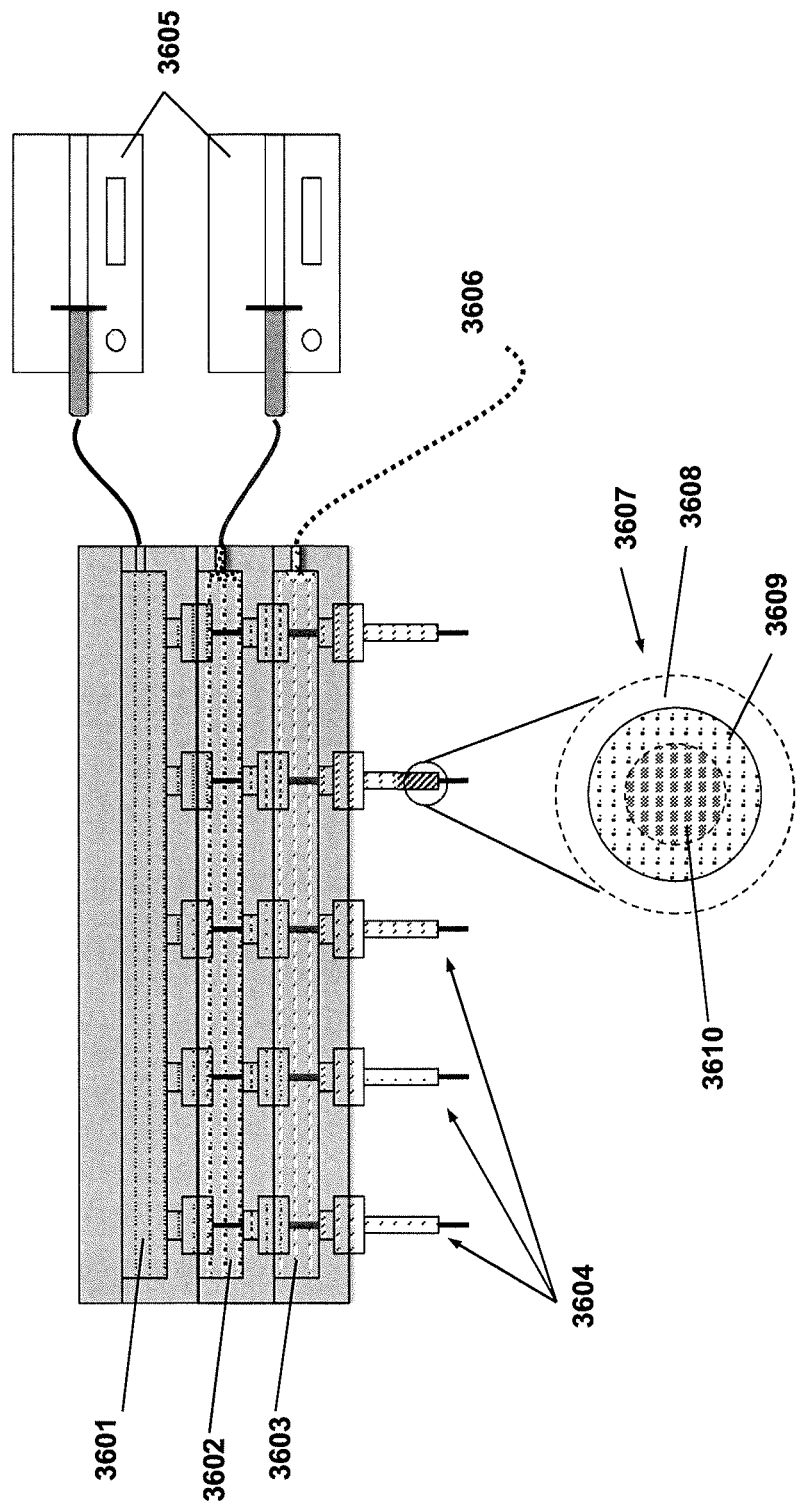
FIG. 36 illustrates a schematic of the process and system for producing $Al_2O_3$/ITO hybrid nanofibers suitable for use in flexible solar cells.

FIG. 36 illustrates yet another exemplary schematic of a process described herein, particularly a layered nanocomposite nanofiber that is prepared by a coaxial gas assisted electrospinning process. In some instances, a first fluid stock 3601 (e.g., comprising a metal precursor and a polymer), is electrospun with a second fluid stock 3602 (e.g., comprising a second metal precursor and a second polymer, the second precursor and polymer independently being either the same or different from the first), and a third fluid (e.g., gas) 3603. The fluid stocks may be provided to the apparatus by any device, e.g., by a syringe 3605. And the gas may be provided from any source 3606 (e.g., air pump). In some embodiments such an apparatus comprises a plurality of co-axial needles 3604. Exemplary needles, as illustrates by the cross section 3707, comprise an outer sheath tube 3608, at least one intermediate tube 3609, and a core tube 3610. In specific instances, each of the tubes are coaxially aligned (i.e., aligned along the substantially same axis). In certain embodiments, such a process may be utilized to prepare a nanofiber comprising a core and a layer, wherein the core comprises a metal, metal oxide, or ceramic, and the layer comprises a metal, metal oxide or ceramic. In some instances, the core and layer comprise the same or different materials. In an exemplary embodiment, the core comprises aluminum (from an aluminum precursor fluid stock), and the layer may comprise ITO (from an ITO precursor fluid stock).

Precursor Nanofiber

Provided in certain embodiments, is a nanofiber or a plurality (used interchangeably herein with "a collection") of nanofibers comprising a polymer and a metal precursor described herein. In some embodiments, the nanofiber is prepared according to a process as described above. In specific embodiments, the polymer and the metal precursor are present in the nanofiber in the form of a polymer-precursor association. In some instances, as these nanofibers are prepared from the fluid stocks described herein, polymer and precursor ratios of the polymer/precursor nanofibers are as described herein, e.g., for the fluid stock.

In some embodiments, the nanofiber(s) comprise polymer and metal precursor. In some embodiments, the polymer and metal precursor comprise an optional first metal-precursor and a polymer-precursor association, the polymer-precursor association comprising a polymer bound to one or more second metal-precursor. In some embodiments, the weight ratio of metal precursor to polymer is at least 1:2 in some embodiments. In other embodiments there is about equal weights of precursor and polymer. In some embodiments, there is more precursor than polymer by weight. In some embodiments, the weight ratio of the precursor to polymer is at least 1.25:1, at least 1.5:1, at least 1.75:1, at least 2:1, at least 3:1, at least 4:1, at least 5:1, at least 6:1, at least 7:1, at least 8:1, at least 9:1, at least 10:1, at least 15:1, at least 20:1, at least 30:1, at least 40:1, at least 50:1, or at least 100:1. In some embodiments, the weight ratio of the precursor to polymer is about 1.25:1, about 1.5:1, about 1.75:1, about 2:1, about 3:1, about 4:1, about 5:1, about 6:1, about 7:1, about 8:1, about 9:1 about 10:1, about 15:1, about 20:1, about 30:1, about 40:1, about 50:1, or about 100:1. In yet other embodiments, the weight ratio of precursor to polymer is between about 1:2 and 10:1, between 1:1 and 4:1, between about 2:1 and 10:1, or between about 3:1 and 8:1.

In some embodiments, a precursor nanofiber provided herein comprises an optional first metal precursor having the formula $ML_b$ (wherein M is a metal and L is one or more ligand as described herein, and b is a suitable number, such as 1-10) and the polymer-precursor association having the formula $P\text{-}(ML_{b-1})_g$ (P being a polymer and g being the precursor saturation or loading number, such a number greater than or equal to 1). In certain embodiments, g is understood to be a number less than or equal to the number of monomeric units or reactive sites (especially if monomeric units having more than one reactive site are uses) present in P. For example, if approximately 0.0113 moles (2 g of nickel acetate) reacts completely with 1 g of 79 kDa of polyvinyl alcohol (approximately 0.0238 moles of vinyl alcohol monomeric residue), then, without any crosslinking, about 47% of the alcohols present in the polyvinyl alcohol will have reacted, and g would be about 884 (0.47 reacted alcohols/polymer*number of alcohol units/polymer, i.e. 79000 polymer molecular weight÷42 alcohol unit molecular weight). In some instances, some cross-linking between polymers (P), e.g., through a metal precursor, will be present (e.g., forming a $P\text{-}ML_{b-2}\text{-}P$; if $ML_b$, $ML_{b-1}$ and $ML_{b-2}$ are all present, the $ML_{b-2}$ residue may be considered a third metal precursor). In specific embodiments, combining a first precursor and a polymer under controlled conditions reduces crosslinking between polymers. In some embodiments, the polymers are less than 20% cross-linked (e.g., less than 20% of the metal precursors are associated with 2 or more polymers and/or less than 20% of the monomeric units of the polymer are connected, e.g., via a metal precursor, to another polymer). In some embodiments, the polymers are less than 10% cross-linked. In specific embodiments, the polymers are less than 5% cross-linked. In more specific embodiments, the polymers are less than 3% cross-linked. In still more specific embodiments, the polymers are less than 2% cross-linked. In yet more specific embodiments, the polymers are less than 1% cross-linked.

In some embodiments, the polymer of the polymer-precursor association is at least 20% saturated with precursor. In specific embodiments, the polymer of the polymer-precursor association is at least 35% saturated with precursor. In more specific embodiments, the polymer of the polymer-precursor association is at least 50% saturated with precursor. In still more specific embodiments, the polymer of the polymer-precursor association is at least 75% saturated with precursor. In various embodiments, the polymer is (e.g., on average) at least 20%, at least at least 30%, at least 40%, at least 50%, at least 60%, at least 70%, at least 75%, at least 80%, at least 85%, at least 85%, at least 90%, at least 95%, at least 96%, at least 97%, at least 98%, or at least 99% saturated. In some instances, the polymer is on average between about 50% and 100%, between about 70% and 100%, between about 90% and 100%, between about 50% and 90%, between about 60% and 80%, or between about 20% and 50% saturated.

In some embodiments, a nanofiber or plurality of nanofibers provided herein comprise a polymer and (e.g., on average) at least 5 elemental wt. % metal. In certain embodiments, a nanofiber or plurality of nanofibers provided herein comprise a polymer and (e.g., on average) at least 10 elemental wt. % metal. In specific embodiments, a nanofiber or plurality of nanofibers provided herein comprise a polymer and (e.g., on average) at least 15 elemental wt. % metal. In more specific embodiments, a nanofiber or plurality of nanofibers provided herein comprise a polymer and (e.g., on average) at least 20 elemental wt. % metal. In specific embodiments, metal constitutes (e.g., on average) at least 25 elemental wt. % of the nanofiber(s). In still more specific embodiments, metal constitutes (e.g., on average) at least 30 elemental wt. % of the nanofiber(s). In yet more specific embodiments, metal constitutes (e.g., on average) at least 35 elemental wt. % of the nanofiber(s). In more specific embodiments, metal constitutes (e.g., on average) at least 40 elemental wt. % of the nanofiber(s). In various embodiments, metal constitutes (e.g., on average) at least 10 elemental wt. %, at least 15 elemental wt. %, at least 45 elemental wt. %, at least 50 elemental wt. % of the nanofiber(s).

In some embodiments, an electrospun precursor nanofiber comprises metal precursor and polymer, wherein the metal precursor and polymer when taken together make up at least 50%, at least 60%, at least 70%, at least 80%, at least 90%, at least 95%, or at least 98% of the total mass of the nanofiber. In specific embodiments, the polymer is an organic polymer.

In some instances, the metal precursor of the precursor may also be optionally solvated (e.g., hydrated if the fluid stock of the fluid medium is water). It is to be understood that disclosures herein are intended to contemplate such solvates.

Nanofiber Processing

In some embodiments, a process provided herein comprises one or more processes for treating (e.g., further treating for those embodiments wherein the treatment is combined with the electrospinning process described above) an electrospun fluid stock (e.g., a precursor nanofiber comprising a polymer and precursor, such as any precursor nanofiber described herein). In specific embodiments, the further treatment comprises converting a precursor nanofiber (the electrospun nanofiber, comprising a polymer and precursor) into a metal, metal oxide (e.g., metal oxide ceramic), or ceramic nanofiber.

One or all of these treatment processes are collectively referred to herein as "calcinations". In some embodiments, to produce a metal, metal oxide, or ceramic nanofiber described herein (e.g., a pure metal and/or ceramic nanofiber for example), a process described herein comprises removing the polymer from the electrospun fluid stock (i.e., precursor nanofiber). In some embodiments, treatment (calcination) of the precursor nanofiber includes removing the polymer (e.g., optionally thermally or chemically removing the polymer). In some embodiments, removing the polymer creates voids and/or defects in the nanofiber. In some instances, it is an object of the disclosure to reduce the amount of polymer in the fluid stock, and/or to employ treatment (calcination) procedures that lead to reduced voids or defects and increased nanofiber length and performance. In some instances, the polymer is removed in a substantially unmodified state. In some instances, the polymer is degraded by any suitable means (e.g., degraded by heat, evaporated, or sublimated). In some instances, the polymer is removed by chemical means (e.g., by solubilizing the polymer or chemically degrading the polymer). In some embodiments, the polymer is chemically degraded in a strong acid or base. In some embodiments, calcination includes removal of the ligand that is optionally a component of the precursor. In various embodiments, the ligand is degraded or removed whole, removed by heat or chemicals, and the like.

In some embodiments, the treatment (calcination) process also comprises converting the precursor(s) to metal (e.g., single metal, or metal alloy), metal oxide (e.g., metal oxide ceramic), and/or ceramic. Such a conversion is also intended to be encompassed herein by the term "calcination". An exemplary calcination is the conversion of a precursor nanofiber comprising a polymer and metal and/or ceramic precursors into a metal and/or ceramic nanofiber. In some embodiments, the conversion of precursors to metal(s), metal oxide(s), and/or ceramic(s) occurs simultaneously with the removal of the polymer. In some embodiments, the conversion of precursors and the removal of the polymer occur at different times. In various embodiments, polymer removal and precursor conversion occur under the same conditions, or under different conditions.

In some embodiments, treatment (calcination) is performed in a gaseous environment. In some embodiments (e.g., if one does not want oxidation reactions to proceed), the gaseous environment is inert (i.e., consisting of non-reactive gases). In some embodiments, treatment (calcination) occurs under an inert atmosphere, such as a noble gas. The noble gases include helium (He), neon (Ne), argon (Ar), krypton (Kr), xenon (Xe), radon (Rn), or mixtures thereof. In specific embodiments, the inert gas is or comprises argon. In other specific embodiments, the inert gas is or comprises nitrogen ($N_2$) gas.

In some embodiments, treatment of the electrospun fluid stock comprises chemical treatment thereof. In specific embodiments, chemical treatment comprises treatment under oxidative conditions. In some embodiments, oxidative treatment comprises treating the electrospun fluid stock with a gas comprising oxygen (e.g., air). In some embodiments, the oxidative treatment also comprises thermal treatment. In certain chemical reactions occur upon calcination, optionally oxidation reactions. In some instances, oxidation converts metal precursors to metal oxide (e.g., a metal oxide ceramic) or ceramic nanofibers. In some embodiments, oxidative reactions are performed in an oxygen-rich environment, such as air. In one particular example (e.g., where the nanofiber is a ceramic nanofiber), calcination is performed in air at about 600° C. for about 2 hours.

In other specific embodiments, chemical treatment comprises treatment under reduction conditions. Reduction is the gain of electrons, which is the opposite reaction from oxidation. In some instances (e.g., such as in the production of pure metal nanofibers), reducing environments are employed. Here for example, the reductive environment prevents or minimizes the conversion of metal precursors to metal oxides (and/or may reduce metal oxides back to metals if oxidation has occurred). In some embodiments, the reducing environment comprises metal such as Mg under vacuum. In some embodiments, the reducing environment comprises hydrogen gas ($H_2$). In specific embodiments, the reductive environment is a mixture of inert gas and hydrogen gas. In some embodiments, the strength of the reductive environment is varied by blending $H_2$ with an inert gas in various proportions. The present disclosure encompasses hydrogen-nitrogen mixtures and the like. In some embodiments, the reductive environment is any environment in which oxidation is prevented or minimized (e.g., an environment substantially devoid of oxygen). In one particular instance, treatment (calcination) is performed under a mixture of argon and hydrogen at about 800° C. for about 2 hours to produce a pure metal nanofiber.

In some embodiments, treatment (calcination) is performed in a liquid environment. In some embodiments, the liquid environment is aqueous. In other embodiments, the liquid environment comprises a different solvent than water, such as an organic solvent. In some embodiments, the liquid environments comprise oxidative, reductive, or inert conditions. An exemplary liquid-based reducing environment is a solution $NaBH_4$. An exemplary oxidizing solution comprises hydrogen peroxide $H_2O_2$. In some embodiments, calcination uses a catalyst (i.e., whether conducted in the gas phase or liquid phase).

Calcination is performed at any suitable temperature for any suitable amount of time. In some instances, higher temperature calcinations produce nanofibers of a smaller diameter. In some instances, low temperature and/or short time may generate small crystal domains in amorphous metal or metal oxides, while high temperature calcination may lead to nanofibers with pure metal or pure metal oxide crystals. In certain instances, crystal size may impact electric conductivity or magnetic properties. In some instances, low temperature calcination of magnetically active metal or metal oxides may generate superparamagnetic nanofibers. In some instances, high temperature calcination may produce metal nanofibers with increased electric conductivity.

In some embodiments, calcination is performed at about 100° C., about 150° C., about 200° C., about 300° C., about 400° C., about 500° C., about 600° C., about 700° C., about 800° C., about 900° C., about 1,000° C., about 1,500° C., about 2,000° C., and the like. In some embodiments, calcination is performed at a temperature of at least 100° C., at least 150° C., at least 200° C., at least 300° C., at least 400° C., at least 500° C., at least 600° C., at least 700° C., at least 800° C., at least 900° C., at least 1,000° C., at least 1,500° C., at least 2,000° C., and the like. In some embodiments, calcination is performed at a temperature of at most 100° C., at most 150° C., at most 200° C., at most 300° C., at most 400° C., at most 500° C., at most 600° C., at most 700° C., at most 800° C., at most 900° C., at most 1,000° C., at most 1,500° C., at most 2,000° C., and the like. In some embodiments, calcination is performed at a temperature of between about 300° C. and 800° C., between about 400° C. and 700° C., between about 500° C. and 900° C., between about 700° C. and 900° C., between about 800° C. and 1,200° C., and the like. In specific embodiments, calcination is performed between 300° C. and 1200° C. In more specific embodiments, calcination is performed between 400° C. and 1000° C. In still more specific embodiments, calcination is performed between 500° C. and 900° C. In some specific embodiments, calcination is performed at 600° C. In other specific embodiments, calcination is performed at 800° C.

In some embodiments, calcination is performed at a constant temperature. In some embodiments, the temperature changes over time. In some embodiments, the temperature increases from a first temperature (e.g., the temperature of the electrospinning process, optionally room temperature) to a second temperature. In some embodiments, calcination then proceeds for a given time at the second temperature. In some embodiments, the temperature continues to vary. The rate of increase in temperature during calcination is varied in certain instances. Any suitable rate of increase is permissible, whereby a nanofiber of the desired properties is obtained. In certain embodiments, the rate of temperature increase is about 0.1° C./min, about 0.3° C./min, about 0.5° C./min, about 0.7° C./min, about 1.0° C./min, about 1.5° C./min, about 2° C./min, about 2.5° C./min, about 3° C./min, about 4° C./min, about 5° C./min, about 10° C./min, about 20° C./min, and the like. In certain embodiments, the rate of temperature increase is at least about 0.1° C./min, at least about 0.3° C./min, at least about 0.5° C./min, at least about 0.7° C./min, at least about 1.0° C./min, at least about 1.5° C./min, at least about 2° C./min, at least about 2.5° C./min, at least about 3° C./min, at least about 4° C./min, at least about 5° C./min, at least about 10° C./min, at least about 20° C./min, and the like. In some embodiments, the rate of temperature increase is at most about 0.1° C./min, at most about 0.3° C./min, at most about 0.5° C./min, at most about 0.7° C./min, at most about 1.0° C./min, at most about 1.5° C./min, at most about 2° C./min, at most about 2.5° C./min, at most about 3° C./min, at most about 4° C./min, at most about 5° C./min, at most about 10° C./min, at most about 20° C./min, and the like. In yet other embodiments, the rate of temperature increase is between about 0.1° C./min and 0.5° C./min, between about 0.5° C./min and 2° C./min, between about 2° C./min and 10° C./min, between about 0.1° C./min and 2° C./min, and the like.

Calcination is performed for any suitable amount of time (e.g., as necessary to arrive at a nanofiber with the desired properties). In some embodiments, the time and temperature of calcination are related to each other. For example, choice of a higher temperature reduces the amount of time needed to produce a nanofiber with a given property. The converse is also true; increasing the time of calcination reduces the necessary temperature, which is advantageous if the nanofiber includes temperature-sensitive materials for example. In some embodiments, calcination is performed for about 5 minutes, about 15 minutes, about 30 minutes, about 1 hour, about 2 hours, about 3 hours, about 4 hours, about 8 hours, about 12 hours, about 1 day, about 2 days, and the like. In some embodiments, calcination is performed for at least 5 minutes, at least 15 minutes, at least 30 minutes, at least 1 hour, at least 2 hours, at least 3 hours, at least 4 hours, at least 8 hours, at least 12 hours, at least 1 day, at least 2 days, and the like. In some embodiments, calcination is performed for at most 5 minutes, at most 15 minutes, at most 30 minutes, at most 1 hour, at most 2 hours, at most 3 hours, at most 4 hours, at most 8 hours, at most 12 hours, at most 1 day, at most 2 days, and the like. In yet other embodiments, calcination is performed for between about 10 minutes and 60 minutes, between about 1 hour and about 5 hours, between about 5 hours and 1 day, and the like.

In some instances, calcination of a precursor nanofiber results in a desired nanofiber (e.g., a pure metal or pure ceramic nanofiber). In some embodiments, the nanofiber consists essentially of pure metal or ceramic (i.e., optionally including small amounts of other materials). In some embodiments, the other materials are residual polymer, residual carbonaceous material (e.g., degraded ligand and/or polymer), minor amounts of oxygen (e.g., in the form of a metal oxide if the nanofiber is "pure metal"), or other components of the fluid stock.

In one aspect, the process has a high yield (e.g., which is desirable for embodiments in which the precursor is expensive). Yield may be quantified by comparing the number of molecules (e.g., in moles) of precursor molecules in the nanofiber to the number of molecules (e.g., in moles) of precursor molecules that get converted into their final form (e.g., metal, metal oxide, or ceramic) and are incorporated in the nanofiber. In other words, the yield may be calculated by solving for the number of precursor molecules (or y*the number of precursor molecules if the precursor molecule has more than one metal atom (i.e., y metal atoms) therein) in the fluid stock divided by the number of metal atoms in the nanofiber(s) (i.e., metal atoms in fluid stock/metal atoms in nanofiber(s)). In some instances, higher loading of precursor on the polymer may result in higher yield. For example, in one trial loading precursor to polymer at a ratio of 4:1 resulted in an 80% yield. In some embodiments, the metal atoms in the nanofiber are about 10%, about 20%, about 30%, about 33%, about 40%, about 50%, about 60%, about 70%, about 80%, about 90%, about 95%, about 98%, or about 100% of the number of (e.g., in moles) precursor molecules in the fluid stock. In some embodiments, the metal atoms in the nanofiber are at least 10%, at least 20%, at least 30%, at least 33%, at least 40%, at least 50%, at least 60%, at least 70%, at least 80%, at least 90%, at least 95%, at least 98%, or at least 99% of the moles of precursor molecules in the fluid stock. In some embodiment, the moles of precursor molecules in the nanofiber are between about 10% and about 40%, between about 20% and about 50%, or between about 50% and about 100% of the moles of precursor molecules in the fluid stock.

Fluid Stock

Described herein are fluid stocks, fluid stocks having certain characteristics, fluid stocks prepared according to the methods herein disclosed, fluid stocks preparable by the methods herein disclosed, fluid stocks incorporating the precursors herein disclosed, fluid stocks incorporating the polymers herein disclosed, and fluid stocks suitable for the methods and systems herein disclosed. The present disclosure also includes methods for using the fluid stocks, and the like.

In some embodiments, a composition (e.g., for use as an electrospinning fluid stock) provided or used in a process herein comprises metal precursor and polymer. In some embodiments, the metal precursor is present in a weight-to-weight ratio of over 1:2 with the polymer. In specific embodiments, the metal precursor is present in a weight-to-weight ratio of over 1:1 with the polymer. In other embodiments, the precursor to polymer weight ratio is as described throughout this disclosure. In certain embodiments, the fluid stock further comprises water (i.e., the fluid stock is aqueous). In some embodiments, the metal precursor is present in a concentration of at least 200 mM. In other embodiments, the precursor is present in any suitable amount described herein. In various embodiments, the fluid stock comprises a substantially uniform and/or homogenous dispersion or solution (e.g., as measured by viscosity deviations, UV absorbance, or the like).

In specific embodiments, the fluid stock comprises at least two different metal precursors. In more specific embodiments, the at least two different metal precursors comprise different metals. In certain embodiments, use of at least two different metal precursors provides an alloy or composite nanofiber following electrospinning and treatment according to the processes described herein.

In specific embodiments, metal precursor of the fluid stock is at least partially in the form of a polymer-precursor association. In more specific embodiments, the metal precursor is partially in the form of a polymer-precursor association (e.g., P-$(ML_{1-b})_g$ as described herein) and partially in a form that is not associated with a polymer (e.g., $ML_b$ as described herein). In specific embodiments, the precursor present in the fluid stock is at least 80% associated with the polymer. In more specific embodiments, the precursor present in the fluid stock is at least 90% associated with the polymer. In still more specific embodiments, the precursor present in the fluid stock is at least 95% associated with the polymer. In other specific embodiments, the precursor present in the fluid stock is at least 20%, at least 30%, at least 40%, at least 50%, at least 60%, at least 70%, at least 75%, at least 85%, at least 98%, or at least 99% associated with the polymer. In some instances, some cross-linking between polymers (P), e.g., through a metal precursor, will be present (e.g., forming a P-$ML_{b-2}$-P; which is considered to be in "associated" form). In some embodiments, the polymers of a fluid stock described herein are less than 20% cross-linked (e.g., less than 20% of the metal precursors are associated with 2 or more polymers and/or less than 20% of the monomeric units of the polymer are connected, e.g., via a metal precursor, to another polymer). In some embodiments, the polymers are less than 10% cross-linked. In specific embodiments, the polymers are less than 5% cross-linked. In more specific embodiments, the polymers are less than 3% cross-linked. In still more specific embodiments, the polymers are less than 2% cross-linked. In yet more specific embodiments, the polymers are less than 1% cross-linked.

In some instances, increasing the amount of precursor relative to the amount of polymer and/or distributing the precursor relatively uniformly in the fluid stock produces nanofibers with reduced voids and/or fewer defects relative to nanofibers where the amount of precursor is lower or the fluid stock is not uniform.

In some embodiments, the fluid stock is a solution, optionally an aqueous solution. In some embodiments, the polymer is water soluble and the precursor is solubilized by associating with a ligand. In some embodiments, one or more components are not fully dissolved and the fluid stock is a dispersion. In some instances, the fluid stock is uniform or homogenous (e.g., no matter whether the fluid stock is a solution or dispersion). In some embodiments, homogeneity and/or uniformity of the fluid stock is determined by measuring the standard deviation of the viscosity of the fluid stock. In certain embodiments, the viscosity of fractions of the fluid stock deviate from the viscosity of the fluid stock as a whole by less than 5%, less than 10%, less than 20%, or any suitable amount to effectively produce nanofibers described herein.

In some embodiments, the fluid stock is kept uniform or homogenous, e.g., by agitating. In some embodiments, a process described herein further comprises maintaining uniformity of the fluid stock, e.g., by heating and/or agitating the fluid stock. Methods of agitating include, by way of non-limiting example, mixing, stirring, shaking, sonicating, or otherwise inputting energy to prevent or delay the formation of more than one phase in the fluid stock. Any of these methods or equivalents are employed in various embodiments. In some embodiments, the fluid stock is continually agitated. In some embodiments, the fluid stock is agitated to create a uniform dispersion or solution, which is then used in an electrospinning step before the fluid stock (e.g., dispersion or solution) loses uniformity and/or homogeneity (e.g., it before it separates into more than one phase). Exemplary phases are an aqueous phase and an oil phase, or an aqueous phase and a phase that includes polymer or precursor (e.g., a solid/precipitate phase) for example.

In some embodiments, a uniform fluid stock is made by first agitating a solution of precursor or uniform dispersion of precursor. In some embodiments, the fluid stock is made by uniformly distributing precursor in a first dispersion before combining the first dispersion with a second dispersion (e.g., which includes polymer). The precursor solution or uniform dispersion is continually agitated in some embodiments, optionally mixed while being combined with the polymer dispersion to create the fluid stock.

In some embodiments, the fluid stock is an aqueous fluid stock and/or comprises polymer dissolved in water. In some embodiments, the continuous phase of the fluid stock is water (e.g., when the fluid stock is a dispersion). In some embodiments, the solvent is water (e.g., when the fluid stock is a solution). In various embodiments, the solution or dispersion of precursor is aqueous, the solution or dispersion of polymer is aqueous, or both solutions or dispersions are aqueous.

In some embodiments, the fluid stock is heated (e.g., optionally in combination with agitation) to create a substantially uniform or substantially homogenous dispersion or solution. In some embodiments, the fluid stock is made by uniformly distributing precursor in a first dispersion before combining the first dispersion with a second dispersion (e.g., which includes polymer). In some embodiments, the first dispersion is heated, optionally in combination with agitation.

In some embodiments, the polymer concentration in the fluid stock is related to (e.g., proportional to) the average molecular weight of the polymer. For example, in some embodiments when the polymer has a molecular weight of about 1,000,000 atomic mass units, the polymer is present at 1% of the fluid stock by weight. In another example, when the polymer has a molecular weight of about 50,000 atomic mass units, the polymer is present at 20% of the fluid stock by weight. In general, the higher the molecular weight of the polymer, the lower the required concentration of polymer in the fluid stock to achieve high quality metal and/or ceramic nanofibers.

The fluid stock contains any suitable amount of polymer. The weight percent of polymer in the fluid stock is represented as the weight percent of polymer alone, or as the combined weight percent of polymer with associated precursor. In some embodiments, the fluid stock is about 10 weight % polymer or polymer associated with precursor. In other embodiments, the fluid stock comprises about 0.5 weight %, about 1 weight %, about 2 weight %, about 3 weight %, about 4 weight %, about 5 weight %, about 6 weight %, about 7 weight %, about 8 weight %, about 9 weight %, about 10 weight %, about 12 weight %, about 14 weight %, about 16 weight %, about 18 weight %, about 20 weight %, about 30 weight %, or about 40 weight % polymer or polymer associated with precursor. In some embodiments, the fluid stock comprises at least about 0.5 weight %, at least about 1 weight %, at least about 2 weight %, at least about 3 weight %, at least about 4 weight %, at least about 5 weight %, at least about 6 weight %, at least about 7 weight %, at least about 8 weight %, at least about 9 weight %, at least about 10 weight %, at least about 12 weight %, at least about 14 weight %, at least about 16 weight %, at least about 18 weight %, at least about 20 weight %, at least about 30 weight %, or at least about 40 weight % polymer or polymer associated with precursor. In some embodiments, the fluid stock comprises at most about 0.5 weight %, at most about 1 weight %, at most about 2 weight %, at most about 3 weight %, at most about 4 weight %, at most about 5 weight %, at most about 6 weight %, at most about 7 weight %, at most about 8 weight %, at most about 9 weight %, at most about 10 weight %, at most about 12 weight %, at most about 14 weight %, at most about 16 weight %, at most about 18 weight %, at most about 20 weight %, at most about 30 weight %, or at most about 40 weight % polymer or polymer associated with precursor. In some embodiments, the fluid stock comprises from about 1 weight % to about 20 weight % polymer or polymer associated with precursor. In some embodiments, the fluid stock comprises from about 1 weight % to about 10 weight %, from about 1 weight % to about 5 weight %, from about 5 weight % to about 20 weight %, from about 5 weight % to about 10 weight %, from about 10 weight % to about 15 weight %, or from about 15 weight % to about 20 weight % polymer or polymer associated with precursor.

In certain embodiments, polymer concentration in the fluid stock is determined on a monomeric residue concentration. In other words, the concentration of the polymer is determined based on the concentration of polymeric repeat units present in the stock. For example, polymer concentration of polyvinyl alcohol may be measured based on the concentration of (—$CH_2CHOH$—) present in the fluid stock. In some embodiments, the monomeric residue (i.e., repeat unit) concentration of the polymer in the fluid stock is at least 100 mM. In specific embodiments, the monomeric residue (i.e., repeat unit) concentration of the polymer in the fluid stock is at least 200 mM. In more specific embodiments, the monomeric residue (i.e., repeat unit) concentration of the polymer in the fluid stock is at least 400 mM. In still more specific embodiments, the monomeric residue (i.e., repeat unit) concentration of the polymer in the fluid stock is at least 500 mM. In at least 5 mM, at least 100 mM, at least 150 mM, at least 200 mM, at least 250 mM, at least 300 mM, at least 350 mM, at least 400 mM, at least 500 mM, at least 700 mM, at least 900 mM, at least 1.2 M, at least 1.5 M, at least 2 M, at least 5 M, and the like. In some embodiments, the concentration of the precursor in the fluid stock is between 5 mM and 5 M, between 200 mM and 1 M, between 100 mM and 700 mM, and the like. In some embodiments, the concentration of precursor in the fluid stock to monomeric residue in the fluid stock is at least 1:4. In specific embodiments, the concentration of precursor in the fluid stock to monomeric residue in the fluid stock is at least 1:3. In more specific embodiments, the concentration of precursor in the fluid stock to monomeric residue in the fluid stock is at least 1:2. In still more specific embodiments, the concentration of precursor in the fluid stock to monomeric residue in the fluid stock is at least 1:1.2. In yet more specific embodiments, the concentration of precursor in the fluid stock to monomeric residue in the fluid stock is about 1:1 (e.g., within 5%). In other embodiments, the concentration of precursor in the fluid stock to monomeric residue in the fluid stock is at least 1:10, at least 1:8, at least 1:6, at least 1:1.5, at least 1:3.5, at least 1:2.5, or any suitable ratio.

In some embodiments, the fluid stock comprises precursor and polymer, wherein at least 5 elemental wt. % of the total mass of the precursor and polymer is metal. In certain embodiments, at least 10 elemental wt. % of the total mass of the precursor and polymer is metal. In specific embodiments, at least 15 elemental wt. % of the total mass of the precursor and polymer is metal. In more specific embodiments, at least 20 elemental wt. % of the total mass of the precursor and polymer is metal. In specific embodiments, at least 25 elemental wt. % of the total mass of the precursor and polymer is metal. In still more specific embodiments, at least 30 elemental wt. % of the total mass of the precursor and polymer is metal. In yet more specific embodiments, at least 35 elemental wt. % of the total mass of the precursor and polymer is metal. In more specific embodiments, at least 40 elemental wt. % of the total mass of the precursor and polymer is metal. In various embodiments, at least 10 elemental wt. %, at least 15 elemental wt. %, at least 45 elemental wt. %, at least 50 elemental wt. % of the total mass of the precursor and polymer is metal.

In one aspect, the concentration of precursor in the fluid stock is high. The concentration is any suitable concentration. In some embodiments, the concentration of the precursor in the fluid stock is about 5 mM, about 10 mM, about 20 mM, about 40 mM, about 60 mM, about 80 mM, about 100 mM, about 150 mM, about 200 mM, about 250 mM, about 300 mM, about 350 mM, about 400 mM, about 500 mM, about 700 mM, about 900 mM, about 1.2 M, about 1.5 M, about 2 M, about 5 M, and the like. In some embodiments, the concentration of the precursor in the fluid stock is at least 5 mM, at least 10 mM, a at least 20 mM, at least 40 mM, at least 60 mM, at least 80 mM, at least 100 mM, at least 150 mM, at least 200 mM, at least 250 mM, at least 300 mM, at least 350 mM, at least 400 mM, at least 500 mM, at least 700 mM, at least 900 mM, at least 1.2 M, at least 1.5 M, at least 2 M, at least 5 M, and the like. In some embodiments, the concentration of the precursor in the fluid stock is at most 5 mM, at most 10 mM, a at most 20 mM, at most 40 mM, at most 60 mM, at most 80 mM, at most 100 mM, at most 150 mM, at most 200 mM, at most 250 mM, at most 300 mM, at most 350 mM, at most 400 mM, at most 500 mM, at most 700 mM, at most 900 mM, at most 1.2 M, at most 1.5 M, at most 2 M, at most 5 M, and the like. In some embodiments, the concentration of the precursor in the fluid stock is between 5 mM and 5 mM, between 20 mM and 1 M, between 100 mM and 700 mM, between 100 mM and 300 mM, and the like.

In some embodiments, a fluid stock is prepared by (i) dissolving or dispersing a precursor in a first fluid (e.g., water, or another aqueous medium) to form a first composition; (ii) dissolving or dispersing a polymer in a second fluid (e.g., water, or another aqueous medium) to form a second composition; and (iii) combining at least a portion of the first and second compositions to form the fluid stock.

Precursor

In some embodiments, a metal precursor provided herein may be present in a fluid stock described herein, present in a precursor nanofiber described herein, used in an electrospinning process described herein, or the like. In some embodiments, the precursor is any molecule or molecules convertible into a metal, ceramic, or metal oxide (such as a metal oxide ceramic). In many instances, metal precursors are optionally converted, upon treatment of the precursor (e.g., the precursor present in a precursor/polymer nanofiber), into a metal (e.g., a single metal, a metal alloy), a metal oxide (e.g., a metal oxide ceramic) or a ceramic (e.g., metal oxide, or otherwise). In some embodiments, the precursor is a molecule or molecules that associates with polymers, such as those described herein. In some embodiments, the precursor is a molecule or molecules that distributes substantially uniformly along the polymers or within the fluid stock. In some embodiments, an increased weight ratio of precursor in the fluid stock and distribution of the precursor uniformly in the fluid stock results in high quality nanofibers with few voids and/and defects (e.g., compared with a nanofiber where the weight ratio is lower or the fluid stock is not uniform).

Described herein is precursor, precursor having certain characteristics, precursor prepared according to the methods herein disclosed, precursor preparable by the methods herein disclosed, precursor incorporating the ligands herein disclosed, precursor incorporating the metals herein disclosed, and precursor suitable for the methods and systems herein disclosed. Also described herein are methods for using the precursor to produce nanofibers, includes the nanofibers comprising (precursor nanofibers) and/or prepared by the precursors (e.g., metal-, metal oxide-, ceramic-containing nanofibers), and the like.

In some embodiments, the precursor is a metal containing compound that is associated with at least one ligand. In certain embodiments, the metal-ligand association (used interchangeably herein with "metal-ligand complex") is associated via any suitable type of bond or interaction. In specific embodiments, the interaction between the metal and the ligand in the metal-ligand association (metal-ligand complex) is an ionic bond (e.g., cationic metal-anionic ligand salt), a covalent bond, a metal-ligand complex (e.g., coordination complex between ligand and metal), or the like. In some instances a precursor described herein is associated with a polymer instead of, or in addition to, other ligands— such compounds are intended to be considered was metal-ligand associations (whether or not additional ligands are present).

In some embodiments, a precursor provided herein is a metal compound in association with a ligand and free of any association with a polymer (e.g., $ML_b$, wherein M is metal and L is one or more ligand as described herein, and b is a suitable number, such as a number of at least 1, e.g., 1-10); a metal compound is association with a polymer and, optionally, in association with a ligand (e.g., $P-ML_{b-1}$, $ML_{b-1}$ being a second precursor in association with the polymer (P); with a ligand if b is >1); a metal compound in association with more than one polymer and, optionally, in association with a ligand (e.g., $P-ML_{b-2}-P$; with a ligand if b is >2).

In some embodiments, the precursor is a molecule that is substantially identical to the material comprising the nanofiber, optionally a metal. In some embodiments, the precursor is convertible to the material comprising the nanofiber. The precursor is converted by performing the calcination procedures disclosed herein. For example, in some embodiments, metal precursors in complex with a ligand are converted to metal oxide nanofibers by employing oxidizing conditions and heat. In another example, precursors of metal in complex with a ligand are converted to a metal nanofiber by calcinating in reducing conditions and heat. In yet another example, precursors of metal in complex with a ligand are converted to a metal nanofiber by calcinating in inert conditions and heat. In other embodiments, these processes may be performed in the absence of heat.

In some embodiments, pure metal or ceramic nanofibers have attractive properties such as high conductivity for use in devices such as batteries, ultracapacitors, solar cells, and the like. In some embodiments, nanofibers are also useful in the field of catalysis on account of the high surface area to volume ratio. In some embodiments, the precursor comprises a metal. In various instances, the metal is a transition metal, alkali metal, alkaline earth metal, post-transition metal, lanthanide, or actinide. Transition metals include: scandium (Sc), titanium (Ti), vanadium (V), chromium (Cr), manganese (Mn), iron (Fe), cobalt (Co), nickel (Ni), copper (Cu), zinc (Zn), yttrium (Y), zirconium (Zr), niobium (Nb), molybdenum (Mo), technetium (Tc), ruthenium (Ru), rhodium (Rh), palladium (Pd), silver (Ag), cadmium (Cd), hafnium (Hf), tantalum (Ta), tungsten (W), rhenium (Re), osmium (Os), iridium (Ir), platinum (Pt), gold (Au), mercury (Hg), rutherfordium (Rf), dubnium (db), seaborgium (Sg), bohrium (Bh), and hasium (Hs). Alkali metals include: lithium (Li), sodium (Na), potassium (K), rubidium (Rb), cesium (Cs) and francium (Fr). Alkaline earth metals include: beryllium (Be), magnesium (Mg), calcium (Ca), strontium (Sr), barium (Ba), and radium (Ra). Post-transition metals include: aluminum (Al), gallium (Ga), indium (In), tin (Sn), thallium (Tl), lead (Pb), and bismuth (Bi). Lanthanides include the elements with atomic number 57 to 71 on the periodic table. Actinides include the elements with atomic number 89 to 103 on the periodic table. In addition, silicon (Si), germanium (Ge), antimony (Sb) and polonium (Po) are considered metals for the purposes of the present disclosure. In some embodiments, silicon is used in the process described herein to produce silicon nanofibers. In specific embodiments, the metal of the precursor is a transition metal. In some specific embodiments, the metal of the precursor is silicon. In other specific embodiments, the metal of the precursor is not silicon. In further or alternative embodiments, the metal of the precursor is aluminum. In other specific embodiments, the metal of the precursor is not aluminum. In some embodiments, the precursor comprises at least two different metals.

In specific embodiments, the metal is an alkali metal. In other specific embodiments, the metal is an alkaline earth metal. In still other embodiments, the metal is a transition metal. In more specific embodiments, the metal is a period IV transition metal. In other specific embodiments, the metal is a period V transition metal. In some embodiments, the metal is a group XIII metal. In certain embodiments, the metal is a group XIV metal. In certain embodiments, the metal is a metalloid. In specific embodiments, the metal is lithium, beryllium, sodium, magnesium, aluminum, silicon, potassium, calcium, titanium, vanadium, chromium, manganese, iron, cobalt, nickel, copper, zinc, gallium, germanium, zirconium, palladium, silver, cadmium, tin, barium, hafnium, tungsten, lead, or the like.

In specific embodiments, the precursor comprises at least two precursors (i.e., at least a first and second precursor), each precursor comprising a different metal than the other precursor. In specific embodiments, at least one of the metals is silicon. In other specific embodiments, at least one of the metals is aluminum. In still other embodiments, at least one of the metals is zirconium. In some embodiments, the metal of the first precursor is silicon, aluminum, or zirconium, and the metal of the second precursor is not silicon, aluminum, or zirconium.

In specific embodiments, the metal precursor is a metal-ligand association (complex) (e.g., a coordination complex), each metal precursor comprising metal atom(s) associated (complexed) with one or more ligand(s) (e.g., 1-10, 2-9, or any suitable number of ligands). In specific embodiments, the precursor described herein comprises at least two different types of ligand (e.g., at least one acetate and at least one halide). In some embodiments, the precursor is a metal carboxylate (e.g., —OCOCH$_3$ or another —OCOR group, wherein R is an alkyl, substituted alkyl, aryl, substituted aryl, or the like). In specific embodiments, the precursor is lithium acetate, beryllium acetate, sodium acetate, magnesium acetate, aluminum acetate, silicon acetate, potassium acetate, calcium acetate, titanium acetate, vanadium acetate, chromium acetate, manganese acetate, iron acetate, cobalt acetate nickel acetate, copper acetate, zinc acetate, gallium acetate, germanium acetate, zirconium acetate, palladium acetate, silver acetate, cadmium acetate, tin acetate, barium acetate, hafnium acetate, tungsten acetate, lead acetate, or the like. In certain embodiments, the precursor is a metal nitrate. In specific embodiments, the precursor is lithium nitrate, beryllium nitrate, sodium nitrate, magnesium nitrate, aluminum nitrate, silicon nitrate, potassium nitrate, calcium nitrate, titanium nitrate, vanadium nitrate, chromium nitrate, manganese nitrate, iron nitrate, cobalt nitrate nickel nitrate, copper nitrate, zinc nitrate, gallium nitrate, germanium nitrate, zirconium nitrate, palladium nitrate, silver nitrate, cadmium nitrate, tin nitrate, barium nitrate, hafnium nitrate, tungsten nitrate, lead nitrate, or the like. In some embodiments, the precursor is a metal alkoxide (e.g., a methoxide, ethoxide, isopropyl oxide, t-butyl oxide, or the like). In specific embodiments, the precursor is lithium alkoxide, beryllium alkoxide, sodium alkoxide, magnesium alkoxide, aluminum alkoxide, silicon alkoxide, potassium alkoxide, calcium alkoxide, titanium alkoxide, vanadium alkoxide, chromium alkoxide, manganese alkoxide, iron alkoxide, cobalt alkoxide nickel alkoxide, copper alkoxide, zinc alkoxide, gallium alkoxide, germanium alkoxide, zirconium alkoxide, palladium alkoxide, silver alkoxide, cadmium alkoxide, tin alkoxide, barium alkoxide, hafnium alkoxide, tungsten alkoxide, lead alkoxide, or the like. In some embodiments, the precursor is a metal halide (e.g., chloride, bromide, or the like). In specific embodiments, the precursor is lithium halide, beryllium halide, sodium halide, magnesium halide, aluminum halide, silicon halide, potassium halide, calcium halide, titanium halide, vanadium halide, chromium halide, manganese halide, iron halide, cobalt halide nickel halide, copper halide, zinc halide, gallium halide, germanium halide, zirconium halide, palladium halide, silver halide, cadmium halide, tin halide, barium halide, hafnium halide, tungsten halide, or the like. In certain embodiments, the precursor is a diketone (e.g., acetylacetone, hexafluoroacetylacetone, or the like). In specific embodiments, the precursor is lithium diketone, beryllium diketone, sodium diketone, magnesium diketone, aluminum diketone, silicon diketone, potassium diketone, calcium diketone, titanium diketone, vanadium diketone, chromium diketone, manganese diketone, iron diketone, cobalt diketone nickel diketone, copper diketone, zinc diketone, gallium diketone, germanium diketone, zirconium diketone, palladium diketone, silver diketone, cadmium diketone, tin diketone, barium diketone, hafnium diketone, tungsten diketone, lead diketone, or the like.

In some embodiments, the precursor comprises mixtures or combinations of precursors. In some embodiments, mixtures of metal precursors are used to form metal alloy nanofibers. In some embodiments, metal alloy nanofibers are made from precursors that are alloys of metal. Exemplary metal alloys include CdSe, CdTe, PbSe, PbTe, FeNi (perm alloy), Fe—Pt intermetallic compound, Pt—Pb, Pt—Pd, Pt—Bi, Pd—Cu, and Pd—Hf.

Ligands

As discussed herein, metal precursors used herein generally comprise a metal in association with a ligand. Ligands are associated with the metal in any suitable way, such as through ionic, covalent, coordination complexes, conjugation, or any other suitable association.

In some embodiments, precursor molecules do not have a high solubility in the fluid stock (e.g., optionally not a high solubility in an aqueous fluid stock). In some instances, a poor solubility of precursor may make it difficult to achive (a) an increased weight ratio of precursor in the fluid stock and (b) a substantially uniform distribution of precursor in the fluid stock. In some embodiments, the precursor is solubilized. In some embodiments, the precursor molecules comprise a metal atom in association with a solvating molecule (i.e., a ligand that improves the solubility and/or dispersibility of the metal precursor in the fluid medium, e.g., water). In some embodiments, the a first precursor may be added to a fluid (e.g., water), but forms a second precursor in the fluid (e.g., a solvate and/or an association with a polymer of the fluid stock). Optionally, the solvating molecule is substantially similar to the monomers of the polymer (e.g., ligand is acetate and polymer is polyvinyl acetate). In some embodiments (e.g., where the polymer is soluble in the fluid stock), solubility and uniform distribution of the precursor is achieved by associating the solvating molecule to both the precursor and the polymer.

In some embodiments, the solvating molecule is a ligand. The ligand is suitable for solubilizing or improving the dispersibility of a metal, optionally in an aqueous solution, optionally in the fluid stock. The present disclosure includes achieving a more uniform fluid stock by first solubilizing or distributing the precursor in a first solution. In some embodiments, the solvating molecule or ligand also improves the solubility or dispersibility of the precursor in a first fluid (e.g., dispersion or solution) (i.e., that is mixed with at least one second solution to make a fluid stock).

Some embodiments comprise solubilizing the precursor by associating a metal with a ligand, optionally complexing the metal with a ligand. In some embodiments, the precursor comprises a metal-ligand association (e.g., complex), as discussed herein. In some instances, the ligands are referred to herein as "molecules" in association with the metal. The association between the metal and ligand or molecules is optionally being a chemical bond (e.g., covalent bond), ionic bond, conjugation, or coordination complex. In some embodiments, the precursor is a metal-ligand complex.

The association between the solvating molecule or ligand and the precursor is any physical, chemical, or electromagnetic force known in the art of chemistry. An example of an association is a chemical bond. Examples of bonds are covalent bonds, non-covalent bonds, ionic bonds, hydrogen bonds, and the like. Further examples of associations are hydrophilic interactions and hydrophobic interactions. The skilled practitioner will be aware of many other types of interactions or associations that may be employed such as a Lewis acid-Lewis base interaction between the precursor and the solvating molecule or ligand. In this embodiment, the ligand is generally the "Lewis base", meaning that it furnishes an electron pair to share with a Lewis acid.

In some embodiments, the association is a metal-ligand coordination complex. Metal-ligand coordination complexes are also known as "metal complexes" or "chelation complexes". These complexes generally include a central atom or ion (usually metallic), bonded to a surrounding array of molecules or anions, which in turn are known as ligands or complexing agents. In nature, most compounds containing metals consist of coordination complexes. The association between the metal and ligand is strong or weak in various embodiments.

There are any suitable number of ligands per metal atom (e.g., optionally a number suitable to solvate, i.e., increase solubility or dispersibility of, the metal). The number of ligands per metal atom is referred to as the "coordination number". In some embodiments, the coordination numbers is between two and nine (for $ML_b$ compounds, the coordination number is b). Large numbers of ligands are not uncommon for the lanthanides and actinides. In various embodiments, the number of bonds depends on the size, charge, and electron configuration of the metal ion and the ligands. Metal ions may have more than one coordination number (e.g., depending on oxidation state of the metal).

In some examples there are at least 2 ligand molecules for every metal atom. In other examples, there are at least 3 ligands per metal atom. In some embodiments, the precursor is essentially saturated with ligand. One may determine if the precursor is essentially saturated with ligand by titrating successively more ligand into the metal and determining the amount of ligand complexed by any suitable method known to those in the art of analytical chemistry. In some embodiments, one determines if the precursor is essentially saturated with ligand by waiting successively longer times and determining the amount of ligand complexed by any suitable method known to those in the art of analytical chemistry. In some instances, it may be determined that the precursor is substantially saturated when no more ligand complexes with the metal precursor at successively higher amounts of ligand or at successively longer times.

In one example, the ligand is acetate. In some embodiments, the precursor molecules are metal acetates and the polymer is polyvinyl acetate. In another embodiment, the precursor molecules are metal acetates and the polymer is polyvinyl alcohol.

There are many ligands known to those skilled in the art, any of which are utilized. In some embodiments, a precursor described herein comprises one or more ligand selected from the group consisting of ketones, diketones (e.g., a 1,3-diketone, such as ROCCHR'COR group, wherein R is an alkyl, substituted alkyl, aryl, substituted aryl and R' is R or H), carboxylates (e.g., acetate or —OCOR group, wherein each R is independently an alkyl, substituted alkyl, aryl, substituted aryl), halides, nitrates, amines (e.g., $NR'_3$, wherein each R" is independently R or H or two R", taken together form a heterocycle or heteroaryl), and combinations thereof. Further examples include iodide, bromide, sulfide (e.g., —SR), thiocyanate, chloride, nitrate, azide, fluoride, hydroxide, oxalate, water, nitrite (e.g., $RN_3$), isothiocyanate, acetonitrile, pyridine, ammonia, ethylenediamine, 2,2'-bipyridine, 1,10-phenanthroline, nitrite, triphenylphosphate, cyanide, carbon monoxide, or alko-oxide. In some examples, the precursor is a metal complex such as metal acetate, metal halide (e.g., metal chloride), metal nitrate, or metal alko-oxide (e.g., methoxide or ethoxide).

In various embodiments, metal and/or ceramic precursors are metal atoms associated (complexed) with a ligand. Exemplary metal and/or ceramic precursors include nickel acetate, copper acetate, iron acetate, nickel nitrate, copper nitrate, iron alko-oxide, and the like.

The present disclosure also encompasses the use of combinations of ligands. In one example, a first ligand imparts increased solubility to the precursor, while a second ligand preferentially associates with the polymer.

Polymers

In some embodiments, a polymer described herein (e.g., in a process, precursor nanofiber, a fluid stock, or the like) is a polymer (e.g., homopolymer or copolymer) comprising a plurality of reactive sites. In certain embodiments, the reactive sites are nucleophilic (i.e., a nucleophilic polymer) or electrophilic (i.e., an electrophilic polymer). For example, in some embodiments, a nucleophilic polymer described herein comprises a plurality of alcohol groups (such as polyvinyl alcohol—PVA—or a cellulose), ether groups (such as polyethylene oxide—PEO—or polyvinyl ether—PVE), and/or amine groups (such as polyvinyl pyridine, ((di/mono)alkylamino)alkyl alkacrylate, or the like).

In some embodiments, provided herein are fluid stocks comprising and/or methods comprising electrospinning a fluid stock comprising a polymer. The methods described herein optionally utilize an aqueous fluid stock. In some applications, a water-based process is desirable, for instance if one wants to avoid potential health, environmental, or safety problems associated with organic solvents. As described herein, in some embodiments it is advantageous to electrospin a fluid stock that is homogenous. In some embodiments, the fluid stock is homogenous (e.g., which comprises a water-soluble polymer).

In some embodiments, polymers used in the compositions and processes described herein are hydrophilic polymers, including water-soluble and water swellable polymers. In some aspects, the polymer is soluble in water, meaning that it forms a solution in water. In other embodiments, the polymer is swellable in water, meaning that upon addition of water to the polymer the polymer increases its volume up to a limit. Water soluble or swellable polymers are generally at least somewhat hydrophilic. Exemplary polymers suitable for the present methods include but are not limited to polyvinyl alcohol ("PVA"), polyvinyl acetate ("PVAc"), polyethylene oxide ("PEO"), polyvinyl ether, polyvinyl pyrrolidone, polyglycolic acid, hydroxyethylcellulose ("iEC"), ethylcellulose, cellulose ethers, polyacrylic acid, polyisocyanate, and the like. In some embodiments, the polymer is isolated from biological material. In some embodiments, the polymer is starch, chitosan, xanthan, agar, guar gum, and the like.

In some embodiments, the polymer imparts a suitable elongational viscosity to the fluid stock for electrospinning nanofibers. In some embodiments, low shear viscosity leads to beaded nanofibers. In one aspect, uniform distribution of the precursor in the fluid feed helps to maintain a suitably high elongational viscosity.

Viscosity is a measure of the resistance of a fluid which is being deformed by either shear stress or tensile stress. Viscosity is measured in units of poise. In various embodiments, the viscosity of the polymer or fluid stock is measured with or without associated precursor. The polymer or fluid stock has any suitable elongational viscosity. In some embodiments, the polymer or fluid stock has an elongational viscosity of about 10 poise, 50 poise, about 100 poise, about 200 poise, about 300 poise, about 400 poise, about 500 poise, about 600 poise, about 800 poise, about 1000 poise, about 1500 poise, about 2000 poise, about 2500 poise, about 3000 poise, about 5,000 poise, and the like. In some embodiments, the polymer or fluid stock has an elongational viscosity of at least 50 poise, at least 100 poise, at least 200 poise, at least 300 poise, at least 400 poise, at least 500 poise, at least 600 poise, at least 800 poise, at least 1,000 poise, at least 1,500 poise, at least 2,000 poise, at least 2,500 poise, at least 3,000 poise, at least 5,000 poise, and the like. In some embodiments, the polymer or fluid stock has an elongational viscosity of at most 50 poise, at most 100 poise, at most 200 poise, at most 300 poise, at most 400 poise, at most 500 poise, at most 600 poise, at most 800 poise, at most 1,000 poise, at most 1,500 poise, at most 2,000 poise, at most 2,500 poise, at most 3,000 poise, at most 5,000 poise, and the like. In some embodiments, the polymer or fluid stock has an elongational viscosity of between about 100 and 3,000 poise, or between about 1,000 and 5,000 poise, and the like.

Molecular weight is related to the mass of the monomers comprising the polymer and the degree of polymerization. In some embodiments, molecular weight is a factor that affects viscosity. The polymer has any suitable molecular weight. In some embodiments, the polymer has a molecular weight of at least 20,000 atomic mass units ("amu"), at least 50,000 amu, at least 100,000 amu, at least 200,000 amu, at least 300,000 amu, at least 400,000 amu, at least 500,000 amu, at least 700,000 amu, or at least 1,000,000 amu and the like. In some embodiments, the polymer has a molecular weight of at most 20,000 amu, at most 50,000 amu, at most 100,000 amu, at most 200,000 amu, at most 300,000 amu, at most 400,000 amu, at most 500,000 amu, at most 700,000 amu, or at most 1,000,000 amu and the like. In some embodiments, the polymer has a molecular weight of about 20,000 amu, about 50,000 amu, about 100,000 amu, about 200,000 amu, about 300,000 amu, about 400,000 amu, about 500,000 amu, about 700,000 amu, or about 1,000,000 amu and the like. In yet other embodiments, the polymer has a molecular weight of from about 50,000 amu to about 1,00,000 amu, from about 100,000 amu to about 500,000 amu, from about 200,000 amu to about 400,000 amu, or from about 500,000 amu to about 1,00,000 amu and the like.

The polydispersity index ("PDI") is a measure of the distribution of molecular mass in a given polymer sample. The PDI is the weight average molecular weight divided by the number average molecular weight, which is calculated by formula known to those skilled in the art of polymer science. The polymer has any suitable polydispersity index. In some embodiments, the polymer has a polydispersity index of about 1, about 2, about 3, about 4, about 5, about 6, about 7, about 8, about 9, about 10, about 15, about 20, and the like. In some embodiments, the polymer has a polydispersity index of at least 1, at least 2, at least 3, at least 4, at least 5, at least 6, at least 7, at least 8, at least 9, at least 10, at least 15, at least 20, and the like. In some embodiments, the polymer has a polydispersity index of at most 1, at most 2, at most 3, at most 4, at most 5, at most 6, at most 7, at most 8, at most 9, at most 10, at most 15, at most 20, and the like. In some embodiments, the polymer has a polydispersity index of about 1 to about 10, about 2 to about 5, and the like.

The present disclosure includes polymers, includes polymers having the characteristic herein disclosed, includes polymers prepared according to the methods herein disclosed, includes polymers preparable by the methods herein disclosed, includes polymers incorporating the precursor herein disclosed, and includes polymers suitable for the methods and systems herein disclosed. The present disclosure also includes methods for using the polymers, and the like.

In some embodiments, the fluid stock comprises mixtures or combinations of polymers. For example, in some embodiments, a first polymer binds to a first precursor and a second polymer binds to a second precursor (e.g., to form a composite nanofiber following treatment of the precursor nanofiber). In another example, a first polymer associates with a high amount of precursor and a second polymer is chosen to create high quality nanofibers when electrospun (e.g., elongational viscosity). In some embodiments, the fluid stock includes a high-precursor loading polymer and a highly spinnable polymer.

In some embodiments, the fluid stock comprises co-polymers including block co-polymers. In some embodiments, the co-polymer comprises at least one vinylalcohol, vinylpyrrolidone, vinylacetate, ethylene oxide, dimethylacrylamide, and/or polyacrylamide block. In some embodiments, the various blocks of the co-polymer associate with different precursors. In one example, a first polymer block associates with nickel precursor and a second polymer block associates with iron precursor (e.g., to form a composite nanofiber following treatment of a precursor nanofiber that has nano-domains of nickel interspersed with nano-domains of iron corresponding to the distribution of the blocks of their respective polymer associations). In some embodiments, such a nanofiber has different properties than a nickel-iron alloy nanofiber (i.e., where the nickel and iron are substantially uniformly mixed on the molecular level). In some embodiments, provided herein is a nanocomposite nanofiber comprising a first material and a second material. In specific embodiments, the first material is a continuous matrix material. In further or alternative embodiments, the second material makes up discrete, isolated domains of the nanofiber (e.g., on the surface of the nanofiber). In some embodiments, the first material is a ceramic or metal oxide (e.g., forming a continuous matrix). In certain embodiments, the second material is a metal.

In some embodiments, the polymer is removed from the nanofiber following electrospinning (e.g., by the calcination methods herein disclosed). In some embodiments, calcination degrades the polymer. In some embodiments, the fluid stock comprises degradable polymers (e.g., polymers removable by the calcination methods herein disclosed). The polymer is optionally degraded or removed by any suitable means including, but not limited to thermal degradation, chemical degradation, sublimation, evaporation, and the like. In some embodiments, lower molecular weight polymers are easier to remove by evaporation or sublimation.

Polymer—Precursor Associations

In some embodiments, associating the precursor with the polymer achieves at least one of a high proportion of precursor in the fluid stock and a uniform distribution of precursor in the fluid stock. In some instances the association reduces the amount of voids or defects in the nanofiber. In some embodiments, associating the precursor with the polymer increases the solubility of one or more of the precursor and the polymer in the fluid stock. The present disclosure encompasses precursor in association with polymer and encompasses methods for associating precursor with polymer.

In some instances, a moiety (e.g., a hydroxyl, amine, ether, etc.) of the polymer may displace and replace a ligand of the precursor (i.e., converting a first precursor to a second precursor). In other instances, a moiety of the polymer may react directly with the ligand (e.g., a nucleophilic group of a polymer may react with an electrophilic group of the ligand, or vis versa). FIG. 2A illustrates one mechanism by which a polymer may be associated with a precursor.

In some embodiments, the precursor associates with the polymer in the fluid stock. In some embodiments, the process described herein utilizes an association of the precursor with the polymer to provide a fluid stock wherein precursor is uniformly distributed in the fluid stock. In various embodiments, the fluid stock remains a solution or substantially uniform dispersion (e.g., in part because the precursor associates with the polymer in the fluid stock). In various embodiments, the association is a physical, chemical, or electromagnetic force between the precursor and the polymer. Examples of associations are chemical bonds. Examples of bonds are covalent bonds, non-covalent bonds, ionic bonds, hydrogen bonds, and the like. Further examples of associations are hydrophilic interactions and hydrophobic interactions. Other types of suitable interactions or associations are a Lewis acid-Lewis base interaction between the precursor and the polymer. In some embodiments, the association is a metal-ligand complex.

In some embodiments, the monomers along the polymer chain provide sites to which precursor associates. In some embodiments, these sites are chemical groups including but not limited to hydroxyl groups, carbonyl groups, aldehyde groups, esters, amines, coarboxyamide, imines, nitrates and the like. In some embodiments, groups contain hydrocarbons, halogens, oxygen, nitrogen, sulfur, phosphorus and the like. Those skilled in the art will be familiar with chemical groups. Chemical groups are also known as "functional groups". In some embodiments, precursors associate with chemical groups on the polymer through chemical bonds.

In some aspects, the polymer comprises a plurality of moieties. In some embodiments, these moieties are chemical groups, optionally chemical groups of the monomers bound along the polymer chain. In some embodiments, the moieties complex or bind with precursors, including metals. In some embodiments, the moieties displace the ligand of a metal-ligand precursor. In some embodiments, the polymer includes on average at least 100 functional groups, chemical groups, or moieties per polymer molecule that are capable of associating with a precursor (e.g., optionally with a metal precursor).

In one example, the precursors are iron acetates (a metal ligand complex) and the polymer is polyvinyl alcohol. In this example, the moiety or functional group is an alcohol group. The polymer has a plurality of alcohol groups along its backbone suitable for associating with the iron acetate. In this example, the acetate either binds to the alcohol groups while still being complexed with the iron, or the alcohol groups displace the acetate ligand and associate directly with the iron.

In some embodiments, the amount of precursor associated or loaded onto the polymer is high. In some embodiments, higher loading is related to the number of functional groups in the polymer (which depends in part on the molecular weight of the polymer and concentration of the functional groups). In some instances, more functional groups provide more sites for precursor to associate, thereby enabling higher precursor loading.

In some instances, the quantity of precursor associated with the polymer is determined at least in part by the number of ligands per precursor. In some embodiments, more ligands per metal increase the probability of a ligand associating with a functional group on the polymer. In one example, there are three acetate ligands per aluminum in the precursor.

In some embodiments, the polymer is essentially saturated with precursor molecules, meaning that substantially no more precursors will associate with the polymer. In some embodiments, the saturation is determined by adding an excess of precursor to the polymer, separating the polymer from the precursor and determining what quantity of precursor bound to the polymer. The amount of precursor is measured using any suitable technique known in the art of analytical chemistry. In some instances, following separation, the practitioner determines the amount of unassociated precursor, the amount precursor associated with the polymer, or both the amount of unassociated precursor and the amount precursor associated with the polymer. Tests of this nature are conducted with progressively more precursor added to the fluid stock until no more precursor binds to the polymer, indicating that the precursor is present in excess amount and the polymer is saturated. In some instances, measurements are conducted over progressively longer time periods of contact between the precursor and the polymer to verify that no more precursor associates with the polymer at longer times, and the polymer is saturated with precursor. Another suitable method for determining saturation is to calculate the stoichiometry of the association. For example in some instances, one compares the moles of chemical groups on the polymer in the fluid stock and the moles of precursor molecules associated with those functional groups. If one precursor associates with one chemical group, the polymer is saturated when the moles of precursor is substantially equal to the moles of chemical groups.

In some embodiments, the polymer is saturated with precursor up to any suitable level. In some instances, various samples of polymer have a distribution of precursor saturation levels. Individual polymer samples accordingly exceed or fall short of the average precursor saturation. In some embodiments, the polymer is on average less than 100% saturated with precursor. For example, the polymer is on average at least 20%, at least at least 30%, at least 40%, at least 50%, at least 60%, at least 70%, at least 75%, at least 80%, at least 85%, at least 85%, at least 90%, at least 95%, at least 96%, at least 97%, at least 98%, or at least 99% saturated. In some instances, the polymer is on average between about 50% and 100%, between about 70% and 100%, between about 90% and 100%, between about 50% and 90%, between about 60% and 80%, or between about 20% and 50% saturated.

For the purposes of this disclosure, it is to be understood that reference to a polymer type (e.g., PVA) is intended to include such a polymer when not associated with precursor as well as when associated with precursor (in those cases where the polymer is associated with precursor, the polymer refers to the polymer residue that remains following the reaction/association). For example, in instances where PVA is combined with a precursor $ML_b$, reference to PVA includes reference to unassociated polymer of the P—OH type (including partially or completely ionized forms), and the associated P—O-ML$_{b-1}$ type (wherein the reference to "PVA" refers to the P—O portion and the ML$_{b-1}$ refers to a precursor that may be present to the exclusion of ML$_b$ or in addition to ML$_b$, depending on the extent to which the ML$_b$ precursor is loaded upon or associated with the PVA).

Nanofibers

Provided in certain embodiments herein are nanofibers, e.g., nanofibers having any one or more of the characteristics herein disclosed, nanofibers prepared according to the methods described herein, and nanofibers preparable by the methods described herein. Also provided herein are processes for using the nanofibers, devices comprising the nanofibers and the like.

In some embodiments, the nanofibers have few defects and/or voids. In some instances a voids and defects in the nanofiber include breaks in the nanofiber, regions of nanofiber wherein the diameter is so narrow as to be easily broken (e.g., having a diameter of less than 10% or less than 5% of the average nanofiber diameter), regions of the nanofiber wherein the nanofiber material has anomalous morphologies (e.g., crystalline domains in a substantially amorphous nanofiber—such crystalline domains may increase fracturing and brittleness of the nanofiber), and the like. In some embodiments, there are about 1, about 5, about 10, about 50, about 100, and the like defects per linear mm of nanofiber. In some embodiments, there are at most about 1, at most about 5, at most about 10, at most about 50, at most about 100, and the like defects per linear mm of nanofiber. In other embodiments, the nanofibers have fewer defects and/or voids, wherein the number of defects and/or voids in the nanofiber is in comparison to a nanofiber not produced by the methods of the disclosure (for example with a low loading of precursor).

Metal Nanofibers

Provided in various embodiments herein are pure metal nanofibers, nanofibers comprising metal, or nanofibers substantially comprised of metal. Pure metal nanofibers have any suitable percent composition of metal. In some embodiments, a metal nanofiber provided herein comprises about 99.99%, about 99.95%, about 99.9%, about 99%, about 98%, about 97%, about 96%, about 95%, about 90%, about 80%, and the like of metal by mass. In some embodiments, the metal nanofiber comprises at least about 99.99%, at least about 99.95%, at least about 99.9%, at least about 99%, at least about 98%, at least about 97%, at least about 96%, at least about 95%, at least about 90%, at least about 80%, and the like of metal by mass (e.g., elemental mass). In other embodiments, metal nanofibers provided herein comprise at least 50%, at least 60%, at least 70%, or at least 75% metal by mass (e.g., elemental mass). In specific embodiments, metal nanofibers provided herein comprise at least 80% metal by mass. In more specific embodiments, metal nanofibers provided herein comprise at least 90% metal by mass. In still more specific embodiments, metal nanofibers provided herein comprise at least 95% metal by mass.

In certain embodiments, metal nanofibers provided herein comprise a continuous matrix of crystalline metal. In some instances, the continuous matrix of crystalline metal, with few or no defects, provides for improved performance of the metal nanofibers (e.g., improved electrical conductivity).

In some embodiments, the metal nanofibers comprise a single metal. In other embodiments, the metal nanofibers comprise two or more metals. In some embodiments, provided herein are metal nanofibers comprising two or more metals and the metals are in the form of an alloy. In other embodiments, provided herein are metal nanofibers comprising two or more metals and the metals are in the form of a composite (e.g., a layered hybrid nanofiber, a composite with distinct metal segments, a composite with a first metal that forms a continuous matrix and a second metal that is present in isolated domains within the nanofiber, or the like).

In some embodiments, metal nanofibers provided herein comprises less than 10% carbon by mass (e.g., elemental mass). In certain embodiments, metal nanofibers provided herein comprise less than 7% carbon by mass. In specific embodiments, metal nanofibers provided herein comprise less than 5% carbon by mass. In more specific embodiments, metal nanofibers provided herein comprise less than 3% carbon by mass. In still more specific embodiments, metal nanofibers provided herein comprise less than 1% carbon by mass. In some embodiments, metal nanofibers provided herein comprises less than 5% oxygen by mass (e.g., elemental mass). In certain embodiments, metal nanofibers provided herein comprise less than 3% oxygen by mass. In specific embodiments, metal nanofibers provided herein comprise less than 2% oxygen by mass. In more specific embodiments, metal nanofibers provided herein comprise less than 2% oxygen by mass. In still more specific embodiments, metal nanofibers provided herein comprise less than 0.5% oxygen by mass.

Figure 15:
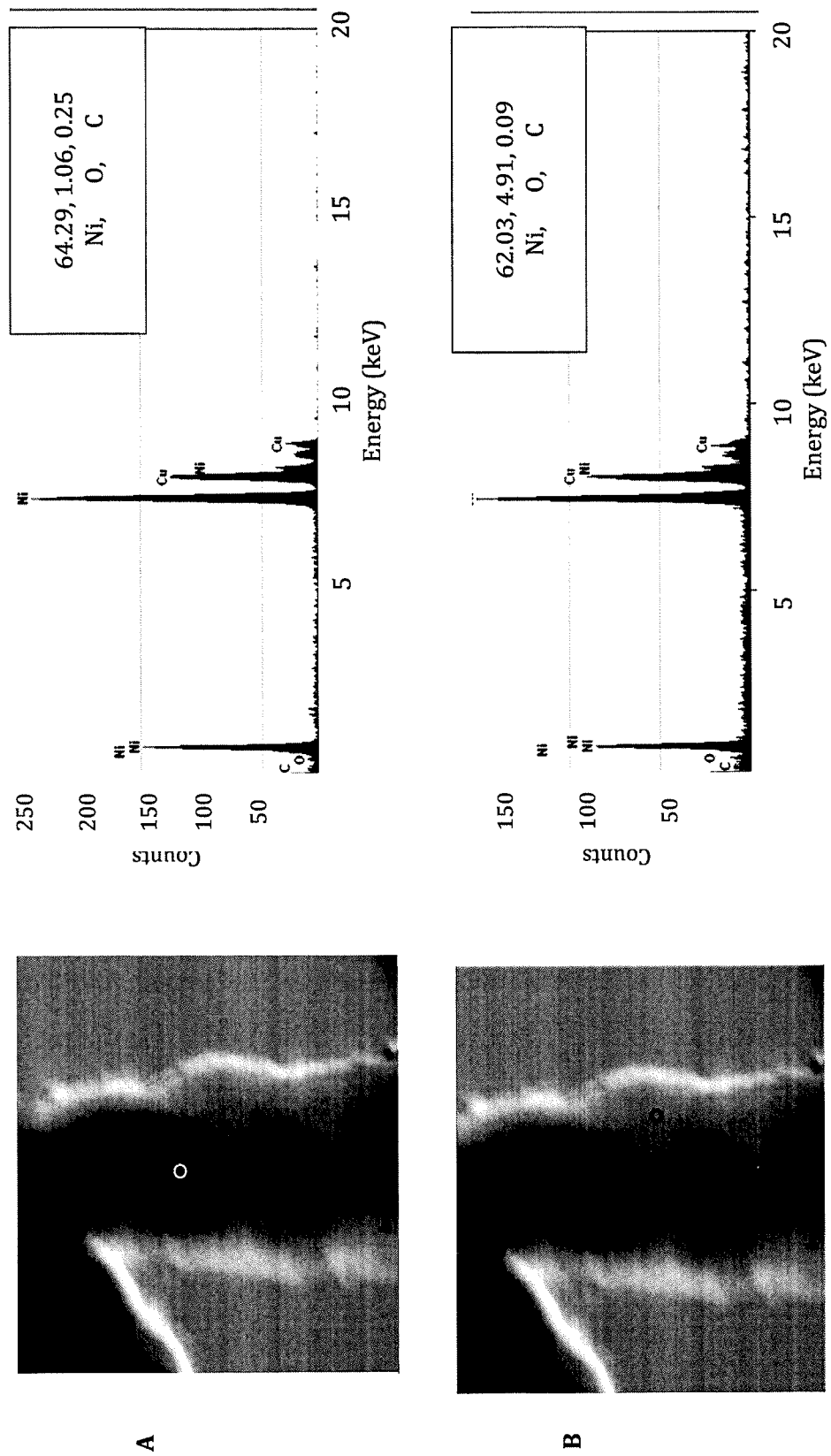
FIG. 15 illustrates elemental analysis of pure Ni nanofibers.

FIG. 15 illustrates the elemental analysis of nickel nanofibers prepared according to a process herein. In both light and dark regions (panels A and B, respectively) of the nanofiber, the nanofiber is observed to have high nickel content. The elemental ratios of nickel to oxygen to carbon were about 64:1:0.25 in the dark region and 62:5:0.1 in the light region.

The metal is any metal, including: transition metal, alkali metal, alkaline earth metal, post-transition metal, lanthanide, or actinide. Suitable transition metals include: scandium (Sc), titanium (Ti), vanadium (V), chromium (Cr), manganese (Mn), iron (Fe), cobalt (Co), nickel (Ni), copper (Cu), zinc (Zn), yttrium (Y), zirconium (Zr), niobium (Nb), molybdenum (Mo), technetium (Tc), ruthenium (Ru), rhodium (Rh), palladium (Pd), silver (Ag), cadmium (Cd), hafnium (Hf), tantalum (Ta), tungsten (W), rhenium (Re), osmium (Os), iridium (Ir), platinum (Pt), gold (Au), mercury (Hg), rutherfordium (Rf), dubnium (db), seaborgium (Sg), bohrium (Bh), and hasium (Hs). Suitable alkali metals include: lithium (Li), sodium (Na), potassium (K), rubidium (Rb), cesium (Cs) and francium (Fr). Suitable alkaline earth metals include: beryllium (Be), magnesium (Mg), calcium (Ca), strontium (Sr), barium (Ba), and radium (Ra). Suitable post-transition metals include: aluminum (Al), gallium (Ga), indium (In), tin (Sn), thallium (Tl), lead (Pb), and bismuth (Bi). Suitable lanthanides include the elements with atomic number 57 to 71 on the periodic table. Suitable actinides include the elements with atomic number 89 to 103 on the periodic table. In some embodiments, the nanofiber is germanium (Ge), antimony (Sb) and polonium (Po), or silicon (Si). By way of non-limiting example, certain methods for producing metal nanofibers are disclosed herein and optionally include calcination under reducing conditions.

In specific embodiments, nanofiber comprises an alkali metal. In further or alternative embodiments, the nanofiber comprises an alkaline earth metal. In certain embodiments, the nanofiber comprises a transition metal. In some embodiments, the nanofiber comprises a period IV transition metal. In certain embodiments, the nanofiber comprises a period V transition metal. In some embodiments, the nanofiber comprises a group XIII metal. In certain embodiments, nanofiber comprises is a group XIV metal. In certain embodiments, the nanofiber comprises a metalloid. In specific embodiments, the nanofiber comprises lithium, beryllium, sodium, magnesium, aluminum, silicon, potassium, calcium, titanium, vanadium, chromium, manganese, iron, cobalt, nickel, copper, zinc, gallium, germanium, zirconium, palladium, silver, cadmium, tin, barium, hafnium, tungsten, lead, combinations thereof, or the like. In specific embodiments, the nanofiber comprises silicon.

Figure 3:
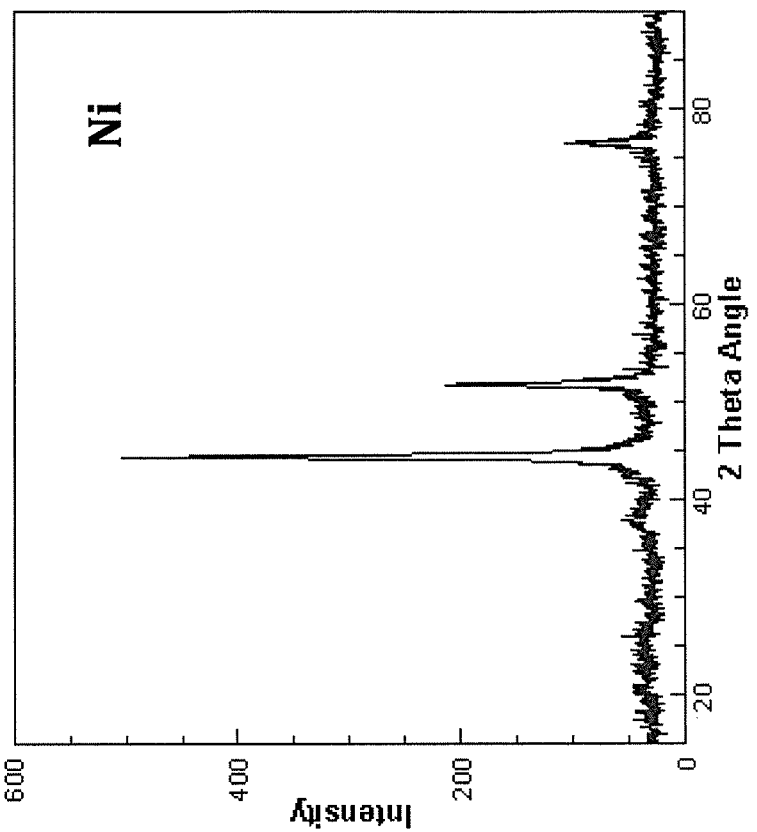
FIG. 3 illustrates micrographs and an x-ray diffraction plot of Ni nanofibers from electrospinning of Ni—Ac/PVA (2:1) feed.
Figure 3:
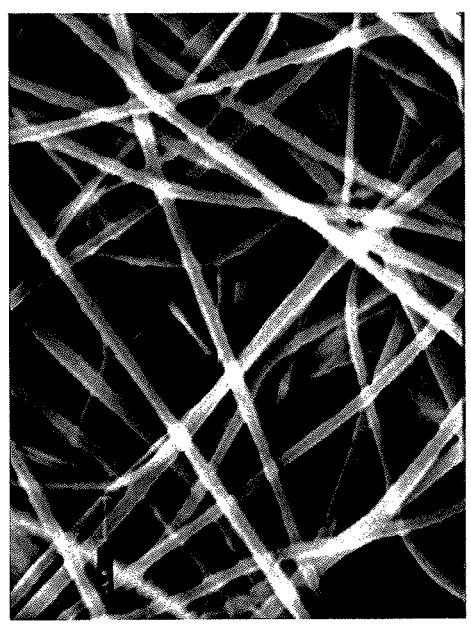
Figure 3:
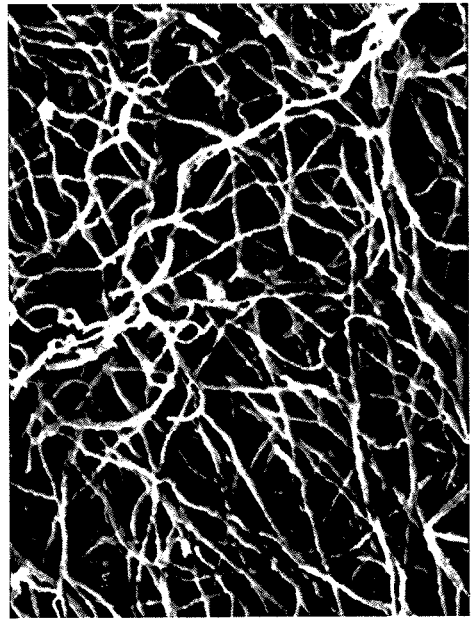
Figure 5:
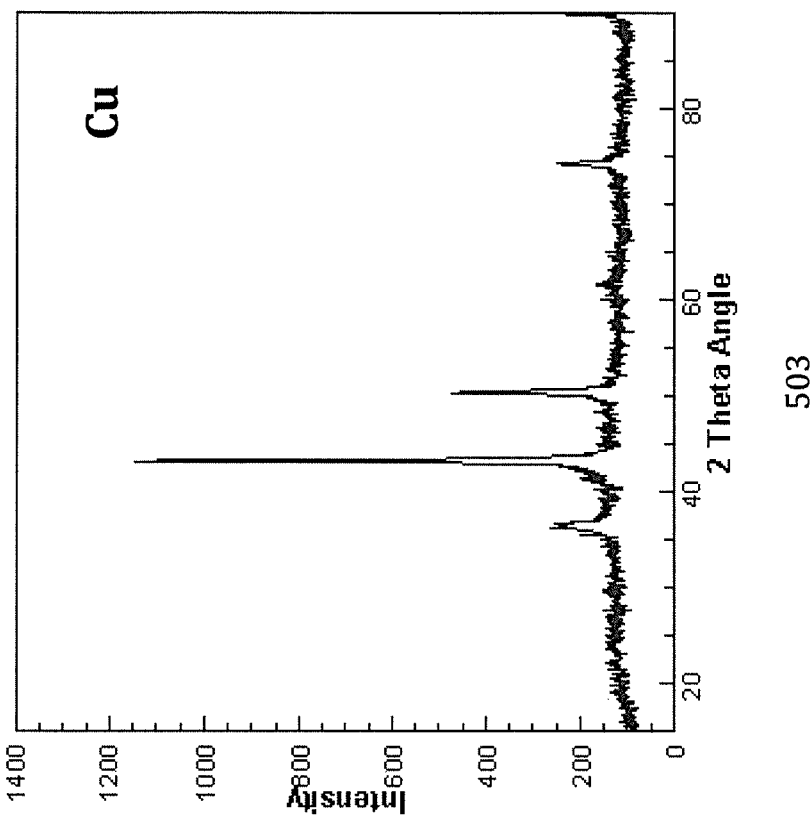
FIG. 5 illustrates micrographs and an x-ray diffraction plot of Cu nanofibers from electrospinning of Cu—Ac/PVA (2:1) solution.
Figure 5:
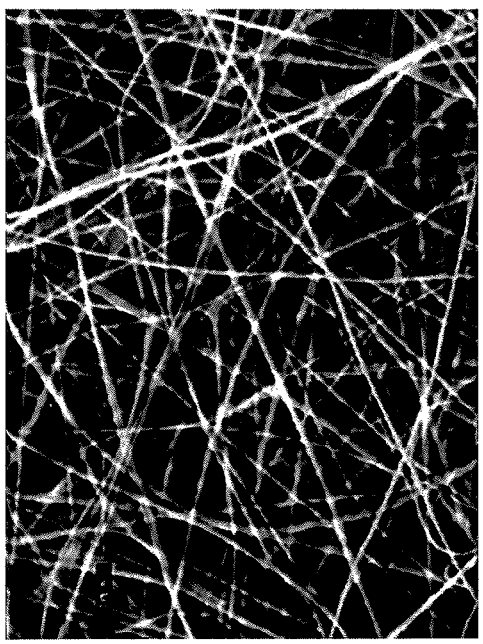
Figure 5:
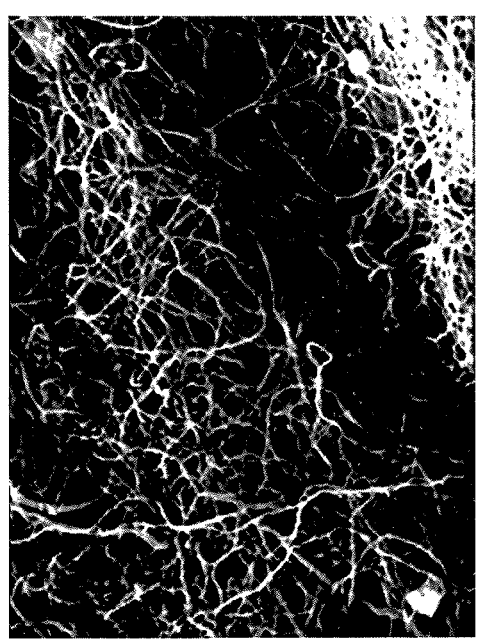
Figure 7:
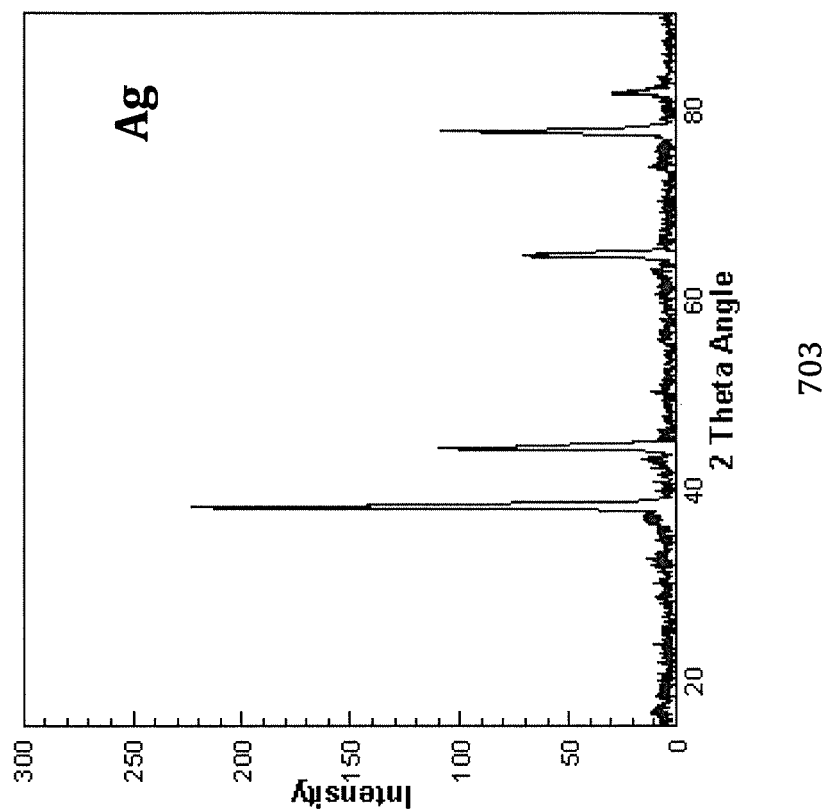
FIG. 7 illustrates micrographs and an x-ray diffraction plot of Ag nanofibers from electrospinning of Ag—Ac/PVA (2:1) solution.
Figure 7:
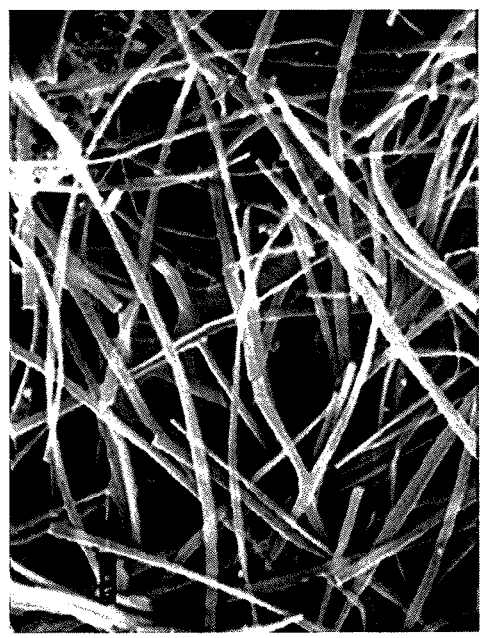
Figure 7:
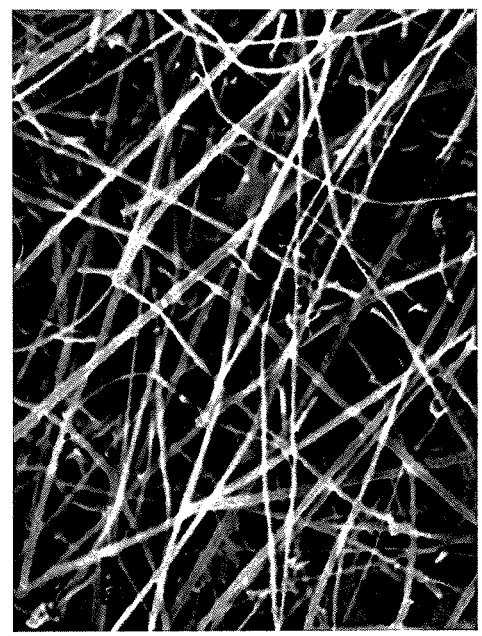
Figure 8:
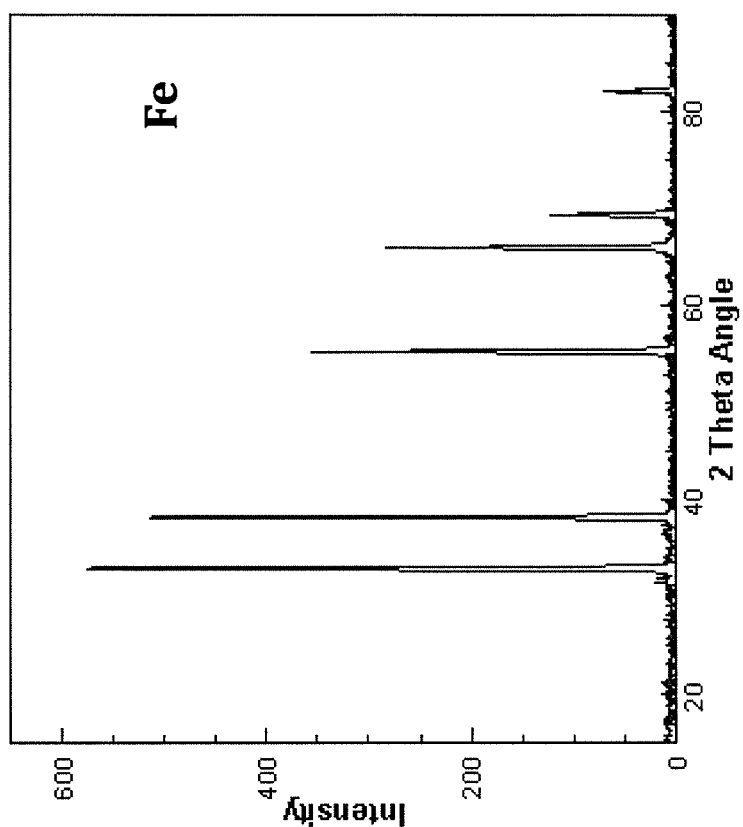
FIG. 8 illustrates micrographs and an x-ray diffraction plot of Fe nanofibers from electrospinning of Fe—Ac/PVA (2:1) solution.
Figure 8:
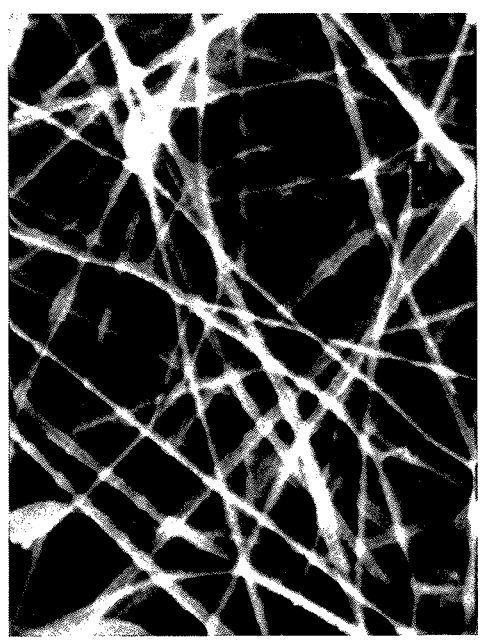
Figure 8:
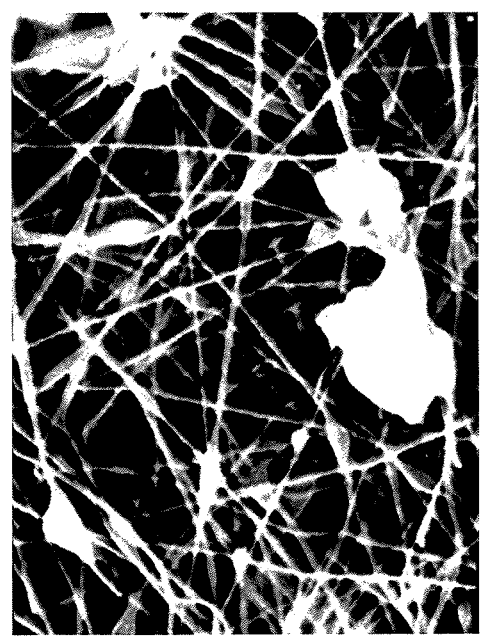
Figure 12:
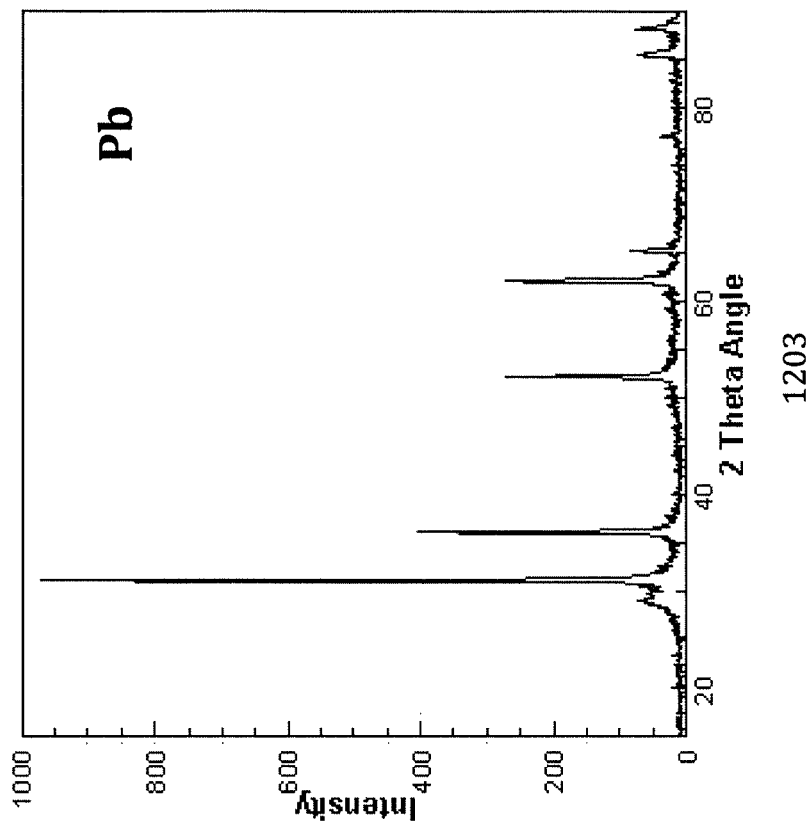
FIG. 12 illustrates micrographs and an x-ray diffraction plot of Pb nanofibers from electrospinning of Pb—Ac/PVA (2:1) solution.
Figure 12:
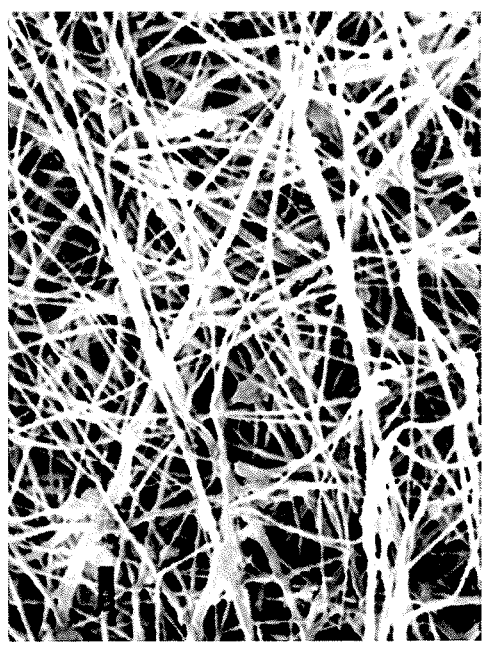
Figure 12:
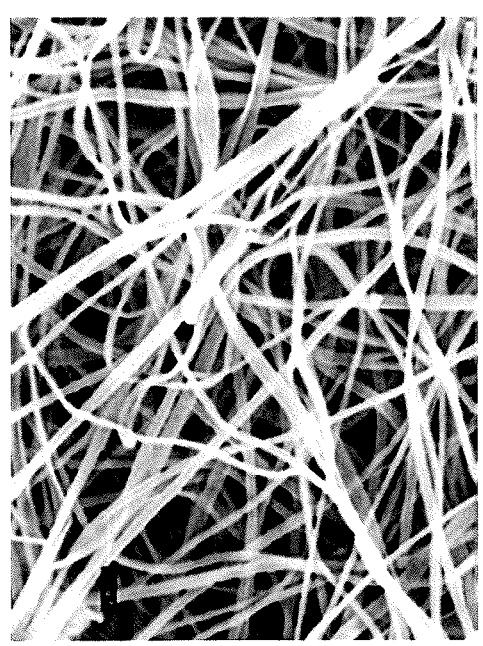
Figure 13:
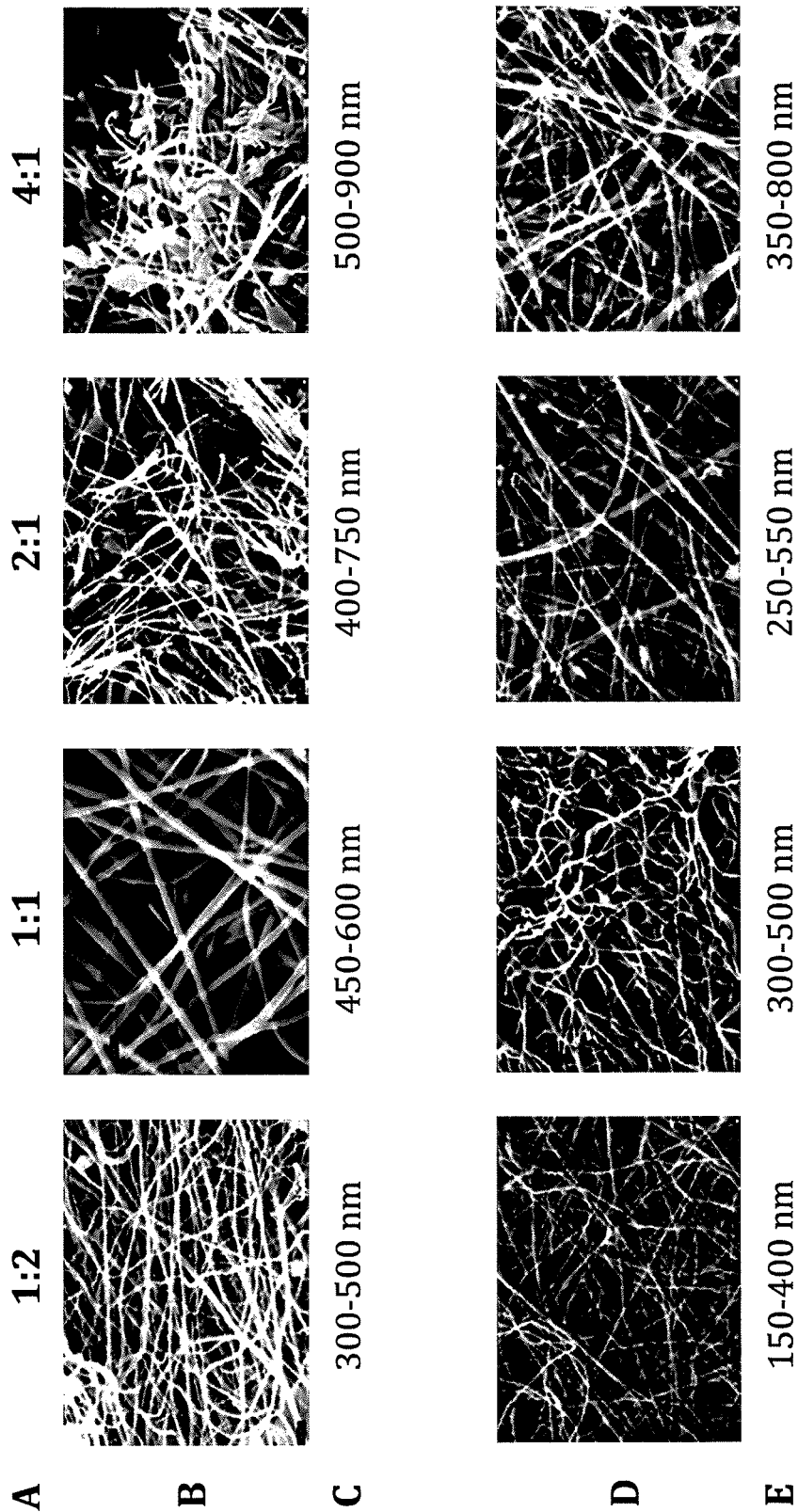
FIG. 13 illustrates micrographs demonstrating the effect of precursor loading on fiber morphology (Ni—Ac/PVA=1:2, 1:1, 2:1 and 4:1).
Figure 14:
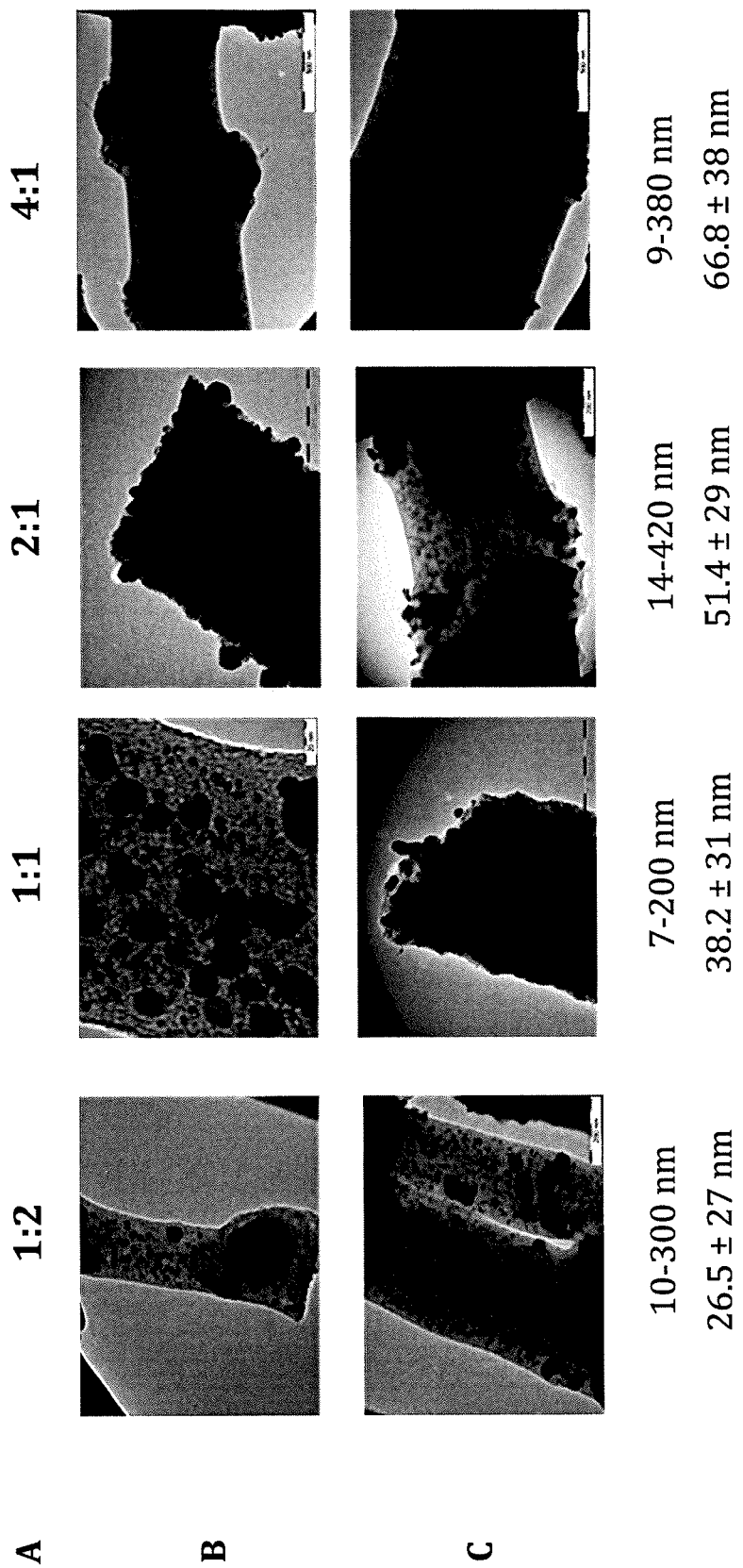
FIG. 14 illustrates TEM micrographs demonstrating the substantial lack of voids in nanofibers (Ni—Ac/PVA=1:2, 1:1, 2:1 and 4:1).
Figure 22:
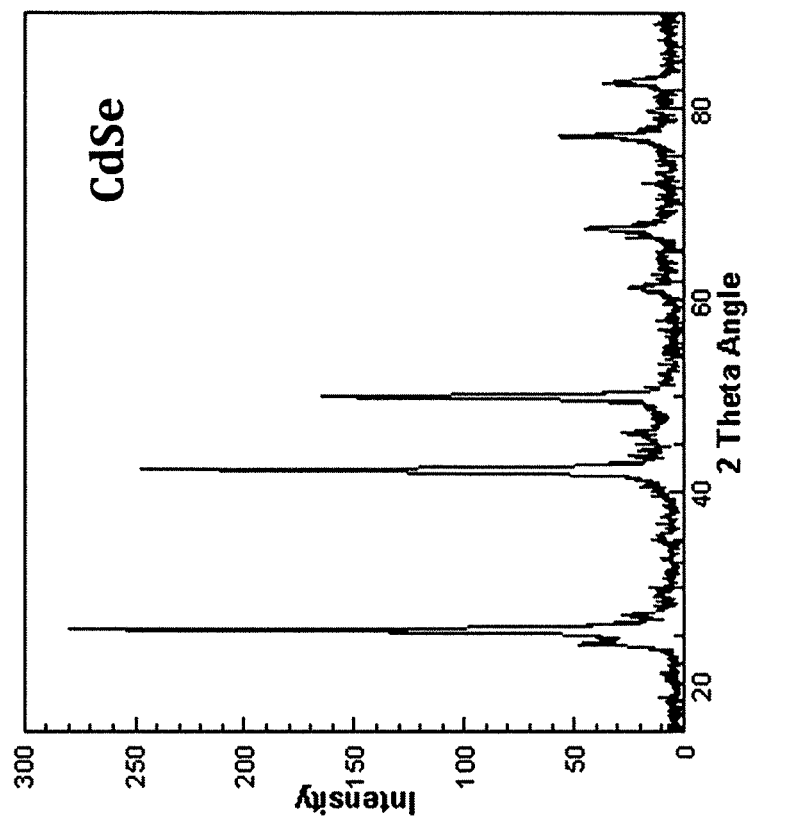
FIG. 22 illustrates micrographs and an x-ray diffraction plot of CdSe alloy nanofibers.
Figure 22:
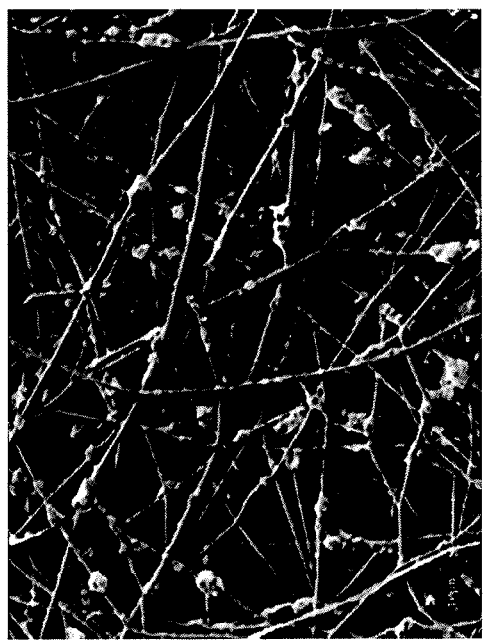
Figure 22:
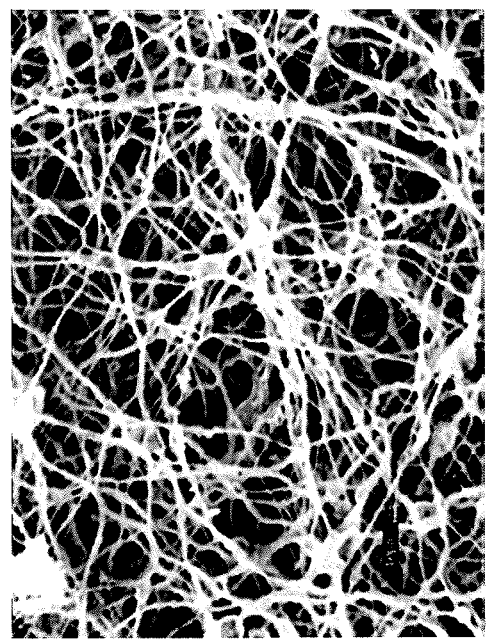
Figure 23:
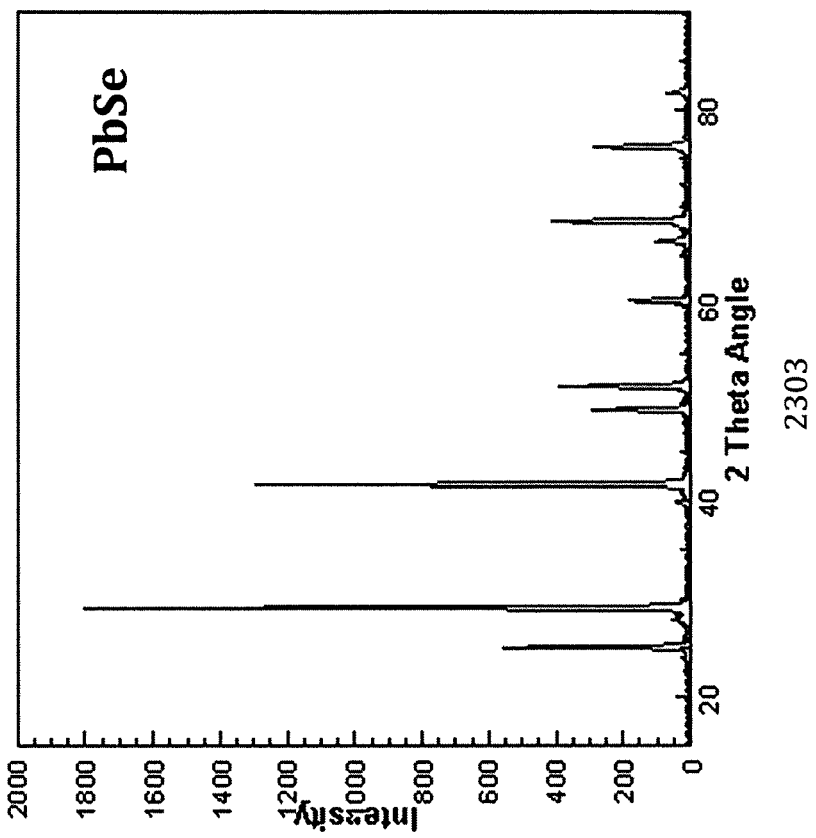
FIG. 23 illustrates micrographs and an x-ray diffraction plot of PbSe alloy nanofibers.
Figure 23:
Figure 23:
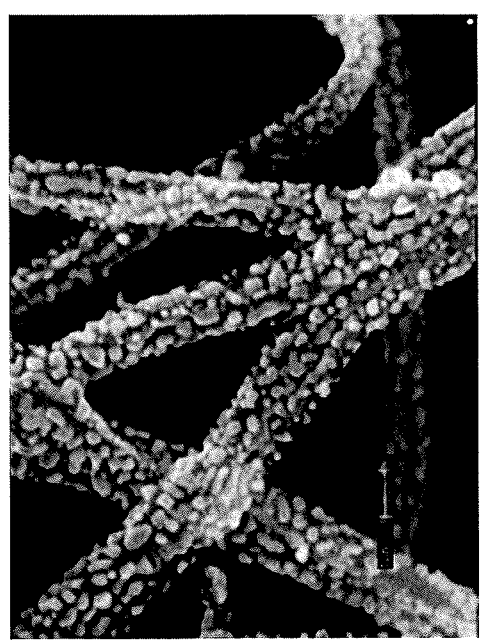
Figure 24:
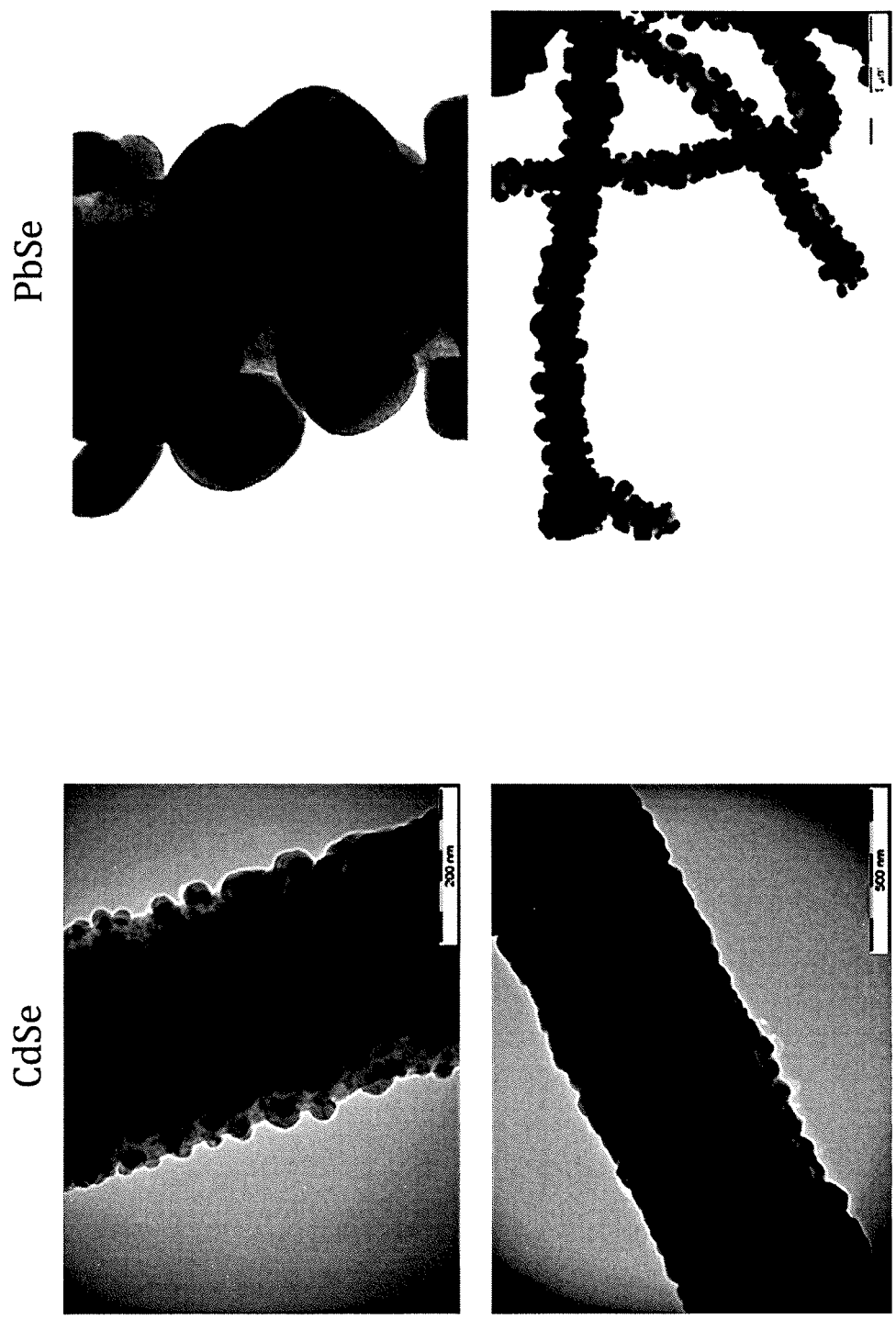
FIG. 24 illustrates TEM micrographs of CdSe and PbSe alloy nanofibers.
Figure 25:
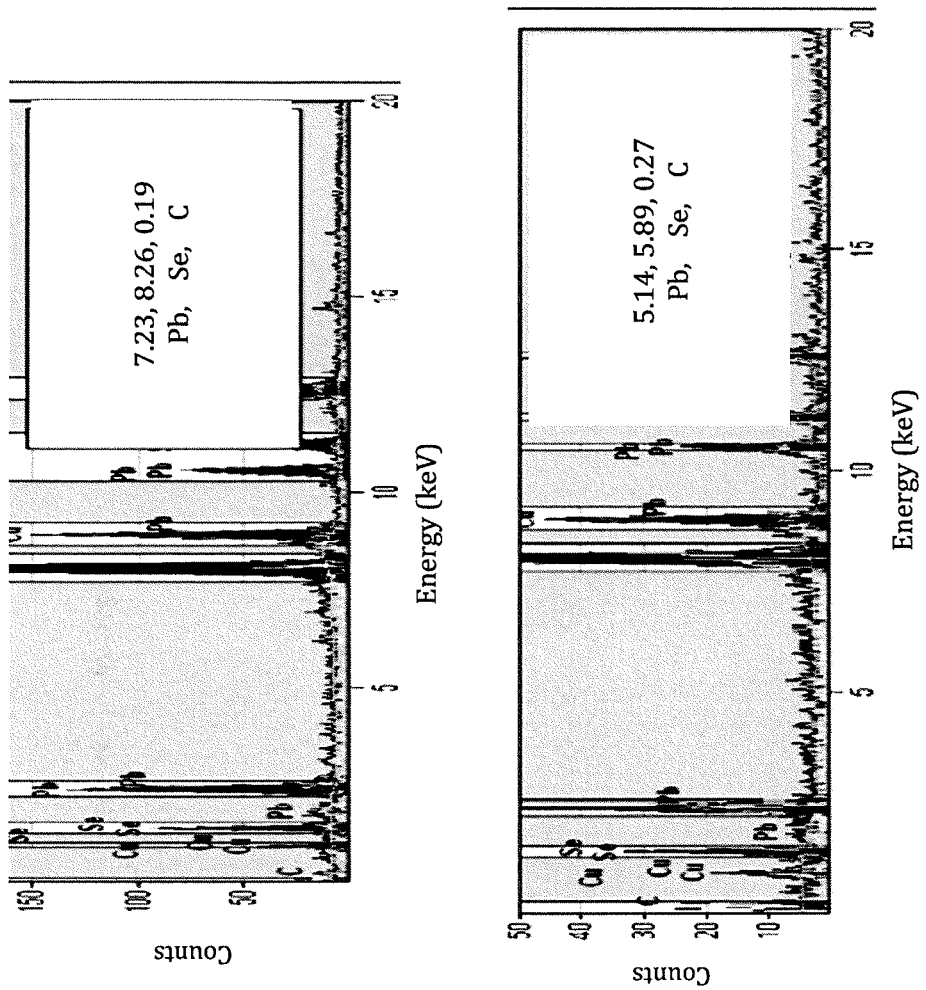
FIG. 25 illustrates elemental analysis of PbSe alloy nanofibers.
Figure 25:
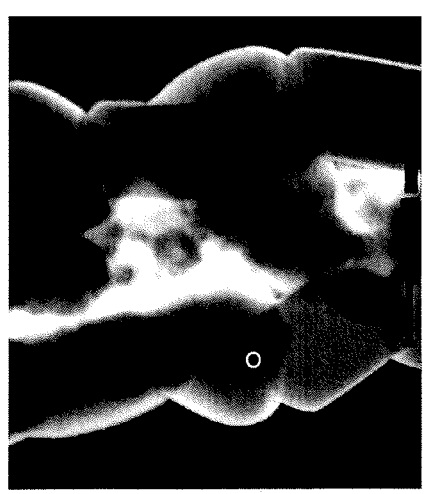
Figure 25:
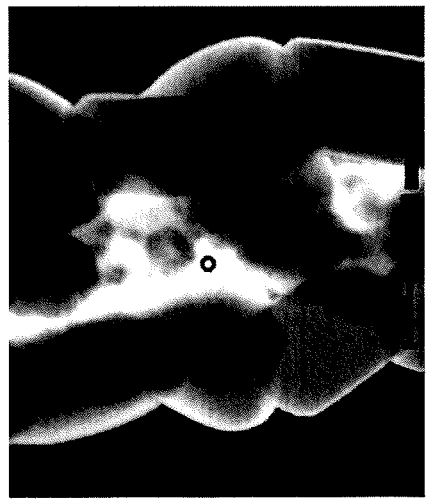
Figure 26:
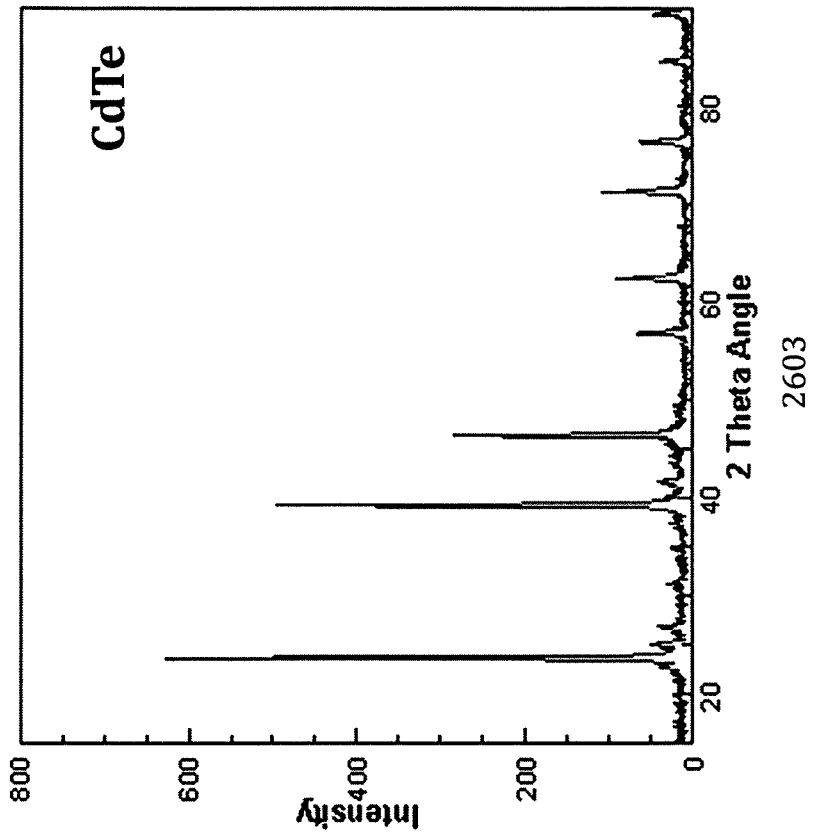
FIG. 26 illustrates micrographs and an x-ray diffraction plot of CdTe alloy nanofibers.
Figure 26:
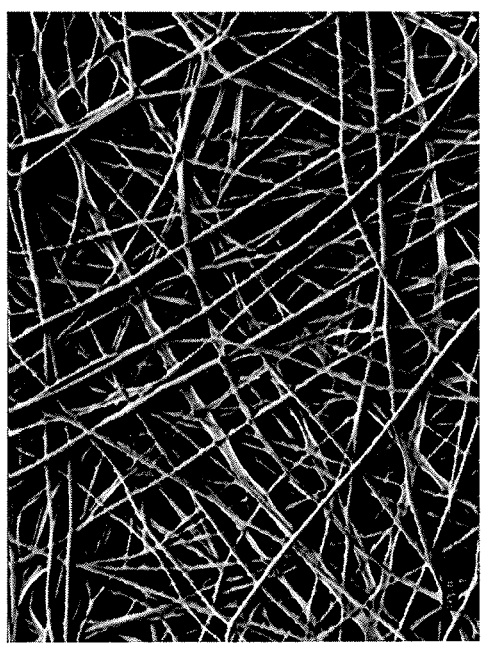
Figure 26:
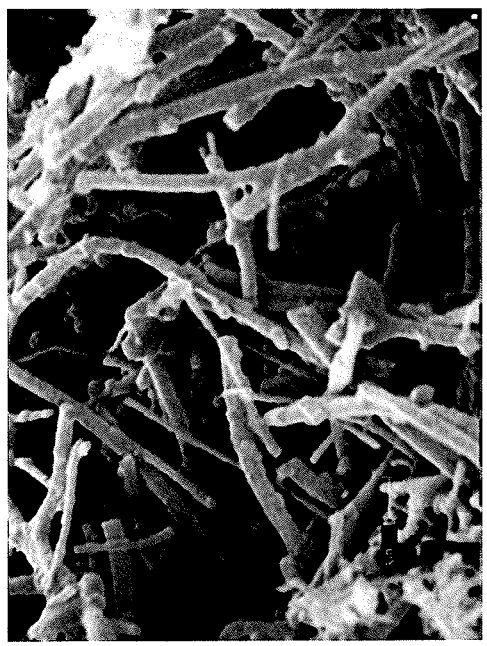
Figure 27:
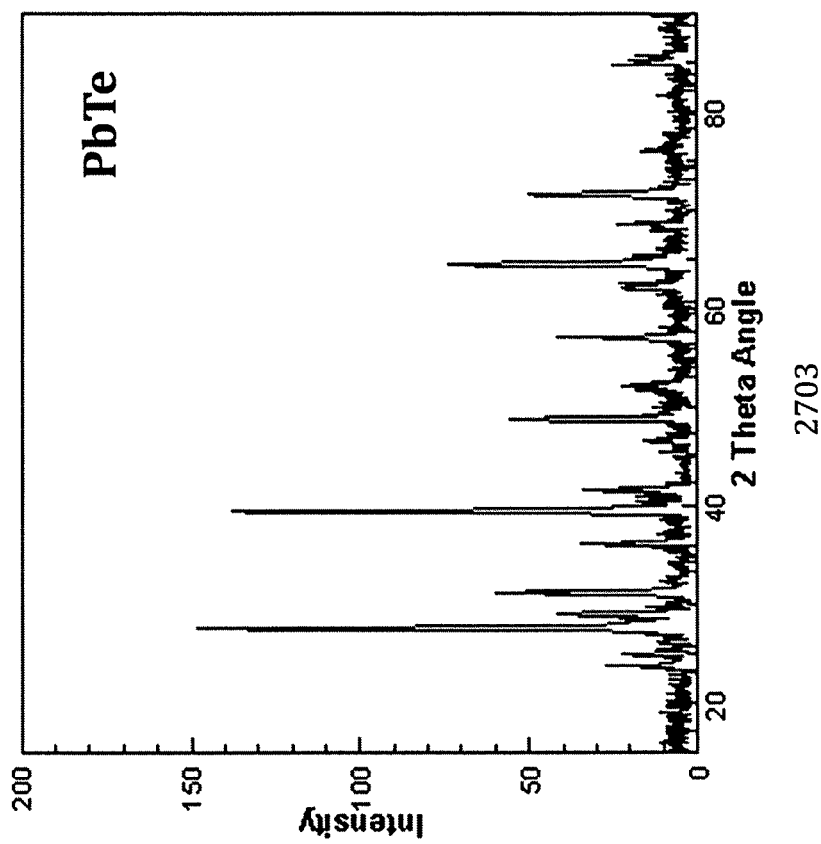
FIG. 27 illustrates micrographs and an x-ray diffraction plot of PbTe alloy nanofibers.
Figure 27:
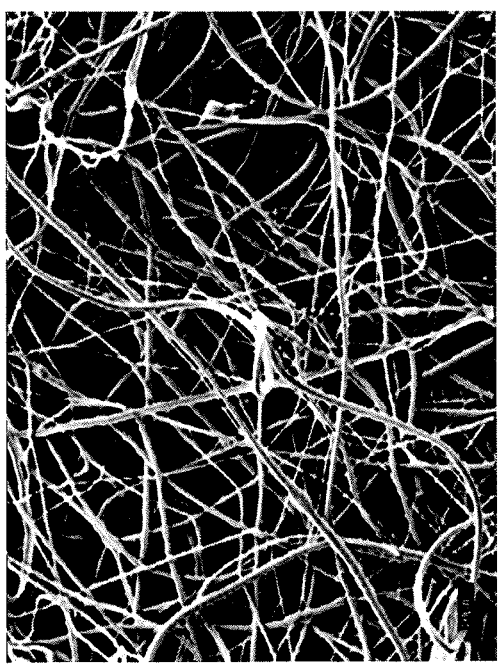
Figure 27:
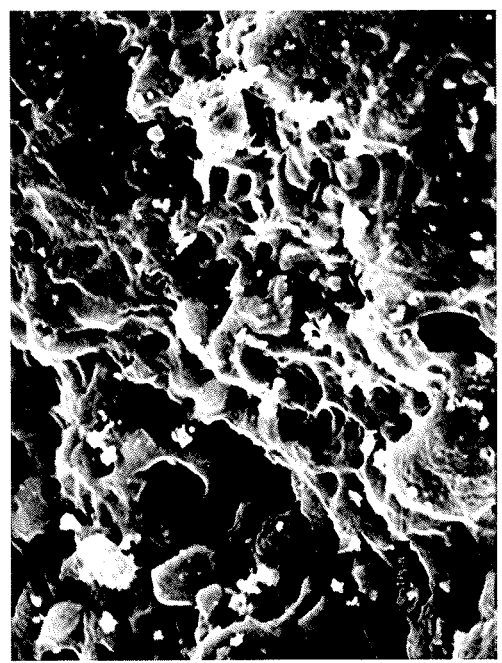
Figure 28:
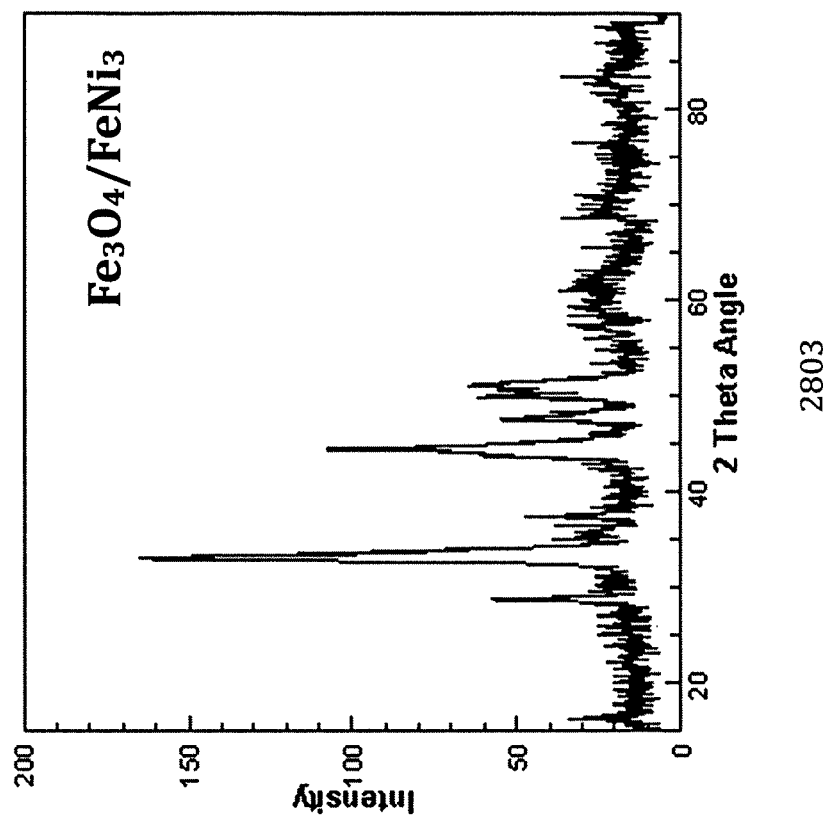
FIG. 28 illustrates micrographs and an x-ray diffraction plot of $Fe_3O_4$/FeNi alloy nanofibers.
Figure 28:
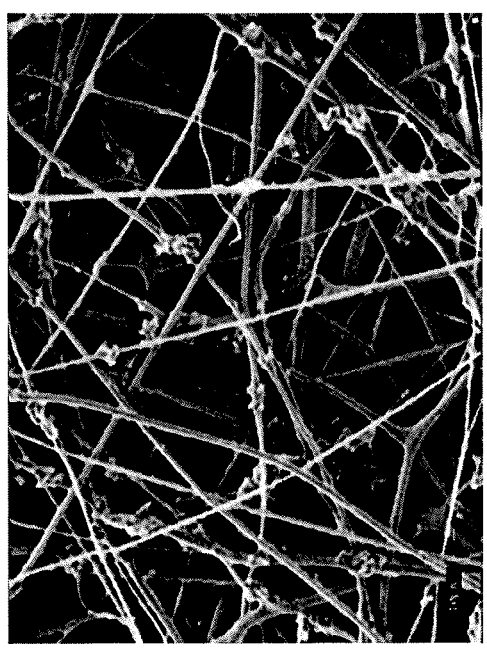
Figure 28:
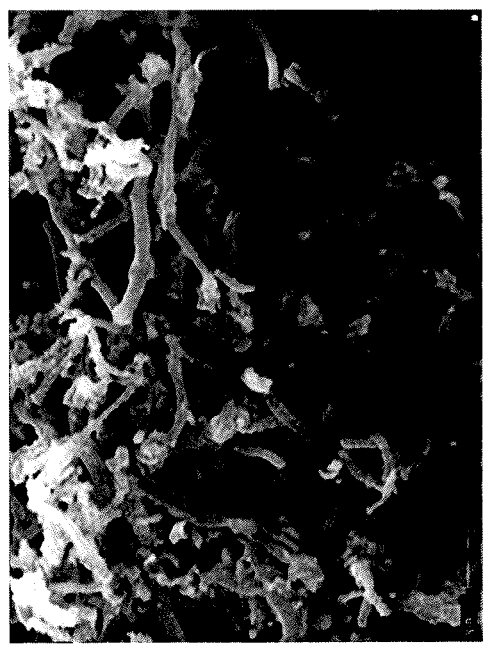
Figure 29:
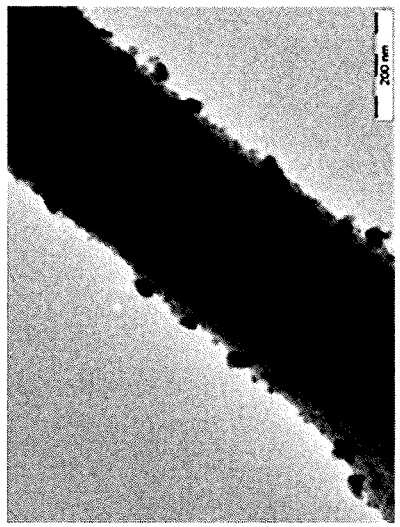
FIG. 29 illustrates TEM micrographs of $Fe_3O_4$/FeNi alloy nanofibers.
Figure 29:
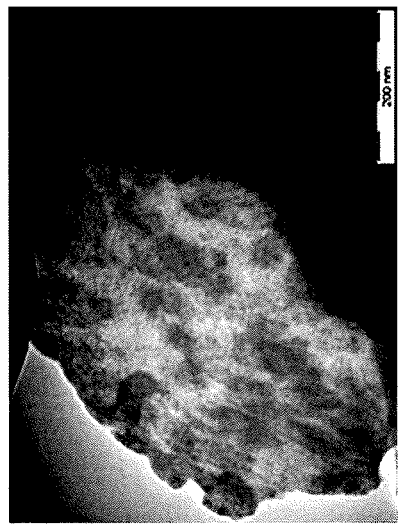
Figure 29:
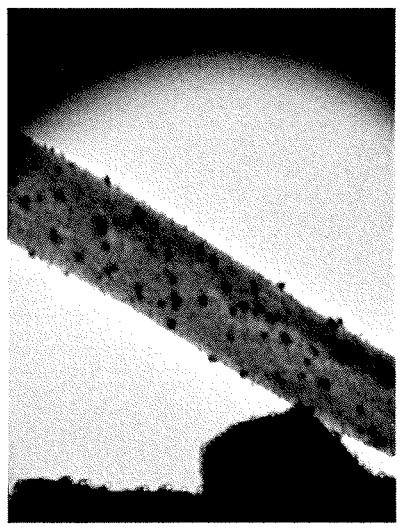
Figure 29:
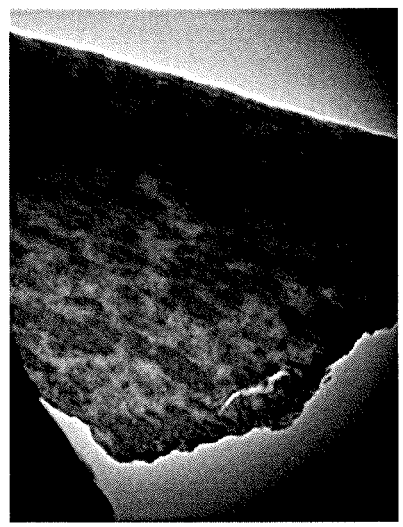

FIGS. 3, 5, 7, 8, 12, 22, 23, 26, 27, and 28 illustrate precursor and metal nanofibers provided herein and/or as prepared according to the processes described herein. FIG. 3 illustrates nickel precursor nanofibers 301 having average diameters of 500-700 nm, and nickel nanofibers 302, having average diameters of 400-500 nm, prepared from the nickel precursor nanofibers 301 after treatment at 600° C. for 2 hours in Argon. FIG. 3 also illustrates the crystal x-ray diffraction pattern 303 of the nickel nanofibers 302. FIG. 5 illustrates copper precursor nanofibers 501 having average diameters of 600-800 nm, and copper nanofibers 502, having average diameters of 300-500 nm, prepared from the copper precursor nanofibers 501 after treatment at 800° C. for 2 hours in a Argon/Hydrogen mixture. FIG. 5 also illustrates the crystal x-ray diffraction pattern 503 of the copper nanofibers 502. FIG. 7 illustrates silver precursor nanofibers 701 having average diameters of 900-1200 nm, and silver nanofibers 702, having average diameters of 600-800 nm, prepared from the silver precursor nanofibers 701 after treatment at 600° C. for 2 hours in air. FIG. 7 also illustrates the crystal x-ray diffraction pattern 703 of the silver nanofibers 702. FIG. 8 illustrates iron precursor nanofibers 801 having average diameters of 300-600 nm, and iron nanofibers 802, having average diameters of 200-500 nm, prepared from the iron precursor nanofibers 801 after treatment at 600° C. for 2 hours in argon. FIG. 8 also illustrates the crystal x-ray diffraction pattern 803 of the iron nanofibers 802. FIG. 12 illustrates lead precursor nanofibers 1201 having average diameters of 500-1100 nm, and lead nanofibers 1202, having average diameters of 250-700 nm, prepared from the lead precursor nanofibers 1201 after treatment at 600° C. for 2 hours in an argon/hydrogen mixture. FIG. 12 also illustrates the crystal x-ray diffraction pattern 1203 of the lead nanofibers 1202. FIG. 13 illustrates nickel precursor nanofibers (Panel B) and nickel nanofibers (Panel D). Depending on the precursor loading (Panel A), based on the weight-to-weight ratio of nickel acetate and PVA combined into a fluid stock, different diameters of precursor nanofibers (Panel C) and metal nanofibers (Panel E) were obtained. FIG. 14 also illustrates nickel nanofibers prepared from fluid stocks prepared from nickel acetate and PVA (Panel A illustrates the loading based on the weight-to-weight ratio of polymer-to-precursor). FIG. 15 illustrates an elemental analysis of metal nanofibers prepared according to the instant disclosure. FIGS. 22 and 23 illustrate metal alloy nanofibers prepared according to the instant disclosure. FIG. 22 illustrates cadmium-selenium precursor nanofibers 2201 having average diameters of 300-1000 nm, and cadmium-selenium alloy nanofibers 2202, having average diameters of 500-700 nm, prepared from the cadmium-selenium precursor nanofibers 2201 after treatment at 600° C. for 2 hours in argon. FIG. 22 also illustrates the crystal x-ray diffraction pattern 2203 of the cadmium-selenium alloy nanofibers 2202. FIG. 23 illustrates lead-selenium precursor nanofibers 2301 having average diameters of 700-1300 nm, and lead-selenium alloy nanofibers 2302, having average diameters of 600-900 nm, prepared from the lead-selenium precursor nanofibers 2301 after treatment at 600° C. for 2 hours in argon. FIG. 23 also illustrates the crystal x-ray diffraction pattern 2303 of the lead-selenium alloy nanofibers 2302. FIG. 24 illustrates a more zoomed view of the cadmium-selenium and lead-selenium alloy nanofibers, and FIG. 25 illustrates an elemental analysis of the lead-selenium alloy nanofibers. FIG. 26 illustrates cadmium-tellurium precursor nanofibers 2601 having average diameters of 500-900 nm, and cadmium-tellurium alloy nanofibers 2602, having average diameters of 300-650 nm, prepared from the cadmium-tellurium precursor nanofibers 2601 after treatment at 600° C. for 2 hours in argon. FIG. 26 also illustrates the crystal x-ray diffraction pattern 2603 of the cadmium-tellurium alloy nanofibers 2602. FIG. 27 illustrates lead-tellurium precursor nanofibers 2701 having average diameters of 400-700 nm, and lead-tellurium alloy nanofibers 2702, having average diameters of 300-550 nm, prepared from the lead-tellurium precursor nanofibers 2701 after treatment at 600° C. for 2 hours in argon. FIG. 27 also illustrates the crystal x-ray diffraction pattern 2703 of the lead-tellurium alloy nanofibers 2702. FIG. 28 illustrates iron-nickel precursor nanofibers 2801 having average diameters of 600-1000 nm, and iron-nickel alloy nanofibers 2802, having average diameters of 200-750 nm, prepared from the iron-nickel precursor nanofibers 2801 after treatment at 600° C. for 2 hours in an argon/hydrogen mixture. FIG. 28 also illustrates the crystal x-ray diffraction pattern 2803 of the iron-nickel alloy nanofibers 2802. FIG. 29 illustrates TEM images for iron oxide/iron-nickel Ceramic and Metal Oxide Nanofibers Provided in various embodiments herein are pure ceramic nanofibers, nanofibers comprising ceramic, or nanofibers substantially comprised of ceramic. In some embodiments, the ceramic nanofiber comprises about 99.99%, about 99.95%, about 99.9%, about 99%, about 98%, about 97%, about 96%, about 95%, about 90%, about 80%, and the like of ceramic by mass. In some embodiments, the ceramic nanofiber comprises at least about 99.99%, at least about 99.95%, at least about 99.9%, at least about 99%, at least about 98%, at least about 97%, at least about 96%, at least about 95%, at least about 90%, at least about 80%, and the like of ceramic by mass (e.g., elemental mass). In other embodiments, ceramic nanofibers provided herein comprise at least 50%, at least 60%, at least 70%, or at least 75% ceramic by mass (e.g., elemental mass). In specific embodiments, ceramic nanofibers provided herein comprise at least 80% ceramic by mass. In more specific embodiments, ceramic nanofibers provided herein comprise at least 90% ceramic by mass. In still more specific embodiments, ceramic nanofibers provided herein comprise at least 95% ceramic by mass.

Provided in various embodiments herein are pure metal oxide (including, e.g., metal oxide ceramics) nanofibers, nanofibers comprising ceramic, or nanofibers substantially comprised of ceramic. In some embodiments, the metal oxide nanofiber comprises about 99.9%, about 99%, about 98%, about 97%, about 96%, about 95%, about 90%, about 80%, and the like of ceramic by mass. In some embodiments, the metal oxide nanofiber comprises at least about at least about 99%, at least about 98%, at least about 97%, at least about 96%, at least about 95%, at least about 90%, at least about 80%, and the like of metal oxide by mass (e.g., elemental mass). In other embodiments, metal oxide nanofibers provided herein comprise at least 50%, at least 60%, at least 70%, or at least 75% metal oxide by mass (e.g., elemental mass). In specific embodiments, metal oxide nanofibers provided herein comprise at least 80% metal oxide by mass. In more specific embodiments, metal oxide nanofibers provided herein comprise at least 90% metal oxide by mass. In still more specific embodiments, metal oxide nanofibers provided herein comprise at least 95% metal oxide by mass. In some embodiments, metal oxide nanofibers provided herein comprise at least 80% metal and oxygen by mass. In more specific embodiments, metal oxide nanofibers provided herein comprise at least 90% metal and oxygen by mass. In still more specific embodiments, metal oxide nanofibers provided herein comprise at least 95% metal and oxygen by mass. In yet more specific embodiments, metal oxide nanofibers provided herein comprise at least 98% metal and oxygen by mass.

In some embodiments, metal nanofibers provided herein comprises less than 10% carbon by mass (e.g., elemental mass). In certain embodiments, metal nanofibers provided herein comprise less than 7% carbon by mass. In specific embodiments, metal nanofibers provided herein comprise less than 5% carbon by mass. In more specific embodiments, metal nanofibers provided herein comprise less than 3% carbon by mass. In still more specific embodiments, metal nanofibers provided herein comprise less than 1% carbon by mass.

In specific embodiments, the ceramic of a nanofiber provided herein is a metal oxide. Exemplary ceramics or metal oxides include but are not limited to $Al_2O_3$, $ZrO_2$, $Fe_2O_3$, CuO, NiO, ZnO, CdO, $SiO_2$, $TiO_2$, $V_2O_5$, $VO_2$, $Fe_3O_4$, SnO, $SnO_2$, CoO, $CoO_2$, $Co_3O_4$, $HfO_2$, $BaTiO_3$, $SrTiO_3$, and $BaSrTiO_3$. Methods for producing ceramic (and/or metal oxide) nanofibers are disclosed herein and optionally include calcination under oxidizing conditions.

The metal of the metal oxide or ceramic is any metal, including: transition metal, alkali metal, alkaline earth metal, post-transition metal, lanthanide, or actinide. Suitable transition metals include: scandium (Sc), titanium (Ti), vanadium (V), chromium (Cr), manganese (Mn), iron (Fe), cobalt (Co), nickel (Ni), copper (Cu), zinc (Zn), yttrium (Y), zirconium (Zr), niobium (Nb), molybdenum (Mo), technetium (Tc), ruthenium (Ru), rhodium (Rh), palladium (Pd), silver (Ag), cadmium (Cd), hafnium (Hf), tantalum (Ta), tungsten (W), rhenium (Re), osmium (Os), iridium (Ir), platinum (Pt), gold (Au), mercury (Hg), rutherfordium (Rf), dubnium (db), seaborgium (Sg), bohrium (Bh), and hasium (Hs). Suitable alkali metals include: lithium (Li), sodium (Na), potassium (K), rubidium (Rb), cesium (Cs) and francium (Fr). Suitable alkaline earth metals include: beryllium (Be), magnesium (Mg), calcium (Ca), strontium (Sr), barium (Ba), and radium (Ra). Suitable post-transition metals include: aluminum (Al), gallium (Ga), indium (In), tin (Sn), thallium (Tl), lead (Pb), and bismuth (Bi). Suitable lanthanides include the elements with atomic number 57 to 71 on the periodic table. Suitable actinides include the elements with atomic number 89 to 103 on the periodic table. In some embodiments, the metal of the metal oxide is a metalloid, such as, germanium (Ge), antimony (Sb) and polonium (Po), or silicon (Si). By way of non-limiting example, certain methods for producing ceramic or metal oxide nanofibers are disclosed herein and optionally include calcination under oxidizing conditions.

In specific embodiments, nanofiber comprises an oxide of or ceramic comprising an alkali metal. In further or alternative embodiments, the nanofiber comprises an oxide of or ceramic comprising an alkaline earth metal. In certain embodiments, the nanofiber comprises a transition metal. In some embodiments, the nanofiber comprises an oxide of or ceramic comprising a period IV transition metal. In certain embodiments, the nanofiber comprises an oxide of or ceramic comprising a period V transition metal. In some embodiments, the nanofiber comprises an oxide of or ceramic comprising a group XIII metal. In certain embodiments, nanofiber comprises an oxide of or ceramic comprising is a group XIV metal. In certain embodiments, the nanofiber comprises an oxide of or ceramic comprising a metalloid. In specific embodiments, the nanofiber comprises an oxide of or ceramic comprising aluminum, silicon, calcium, titanium, vanadium, chromium, manganese, iron, cobalt, nickel, copper, zinc, gallium, germanium, zirconium, cadmium, tin, barium, hafnium, tungsten, lead, combinations thereof, or the like. In specific embodiments, the oxide is not an oxide of silicon, zirconium, or aluminum. In some embodiments, the oxide is an oxide of silicon, zirconium, or aluminum, and further comprises an additional material (e.g., a metal, metal alloy, or the like), such as in a composite material (e.g., a layered hybrid nanofiber, a composite with distinct segments, a composite with a first material that forms a continuous matrix and a second material that is present in isolated domains within the nanofiber—e.g., wherein the oxide is the matrix material, or the like).

In some embodiments, the ceramic and metal oxide nanofibers comprise a single metal type. In other embodiments, the ceramic and metal oxide nanofibers comprise a two or more metal types (e.g., BaTiO3, SrTiO3, BaSrTiO3 (e.g., Ba0.55Sr0.45TiO3), and the like). In some embodiments, provided herein are ceramic and metal oxide nanofibers comprising two or more metal types together form a multi-metal oxide or in an ordered alloy type crystalline lattice. In other embodiments, the two or more metal types form separate oxide materials in an amorphous mixture, in a composite (e.g., a layered hybrid nanofiber, a composite with distinct oxide segments, a composite with a first material that forms a continuous matrix and a second material that is present in isolated domains within the nanofiber, or the like), or the like.

Figure 4:
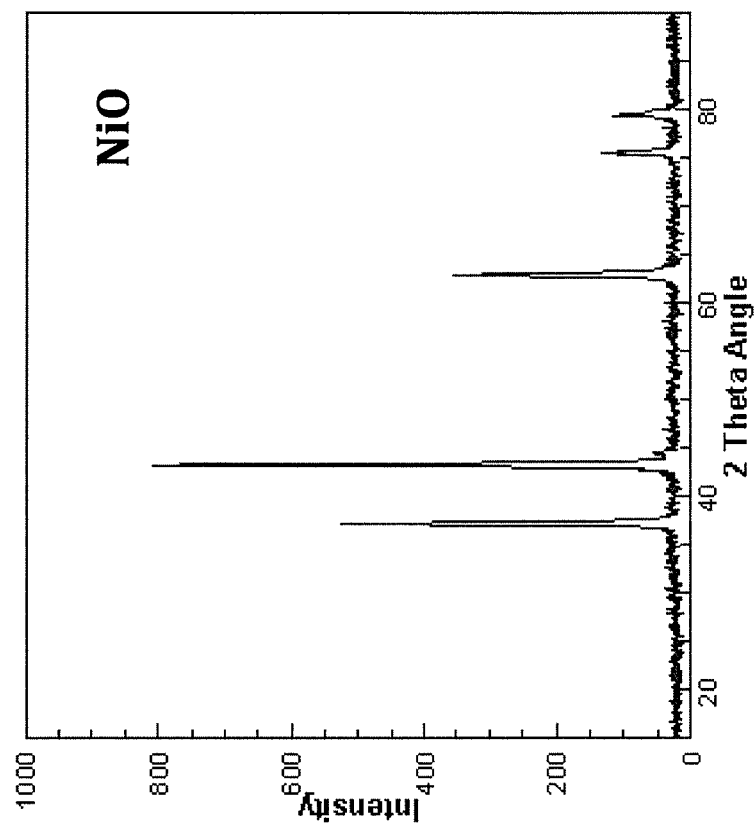
FIG. 4 illustrates micrographs and an x-ray diffraction plot of NiO nanofibers from electrospinning of Ni—Ac/PVA (2:1) feed.
Figure 4:
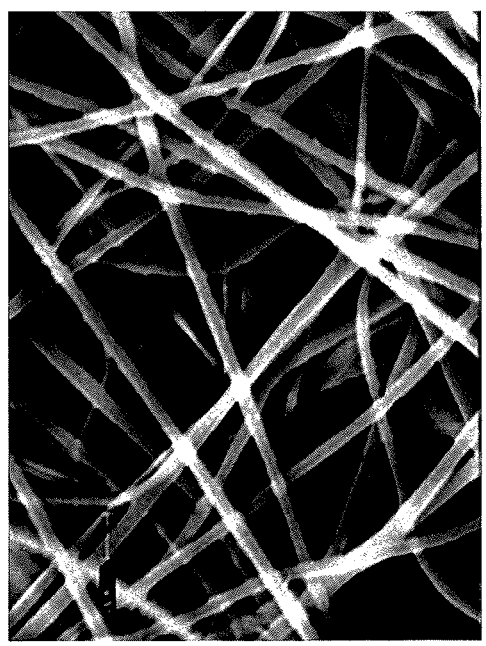
Figure 4:
Figure 6:
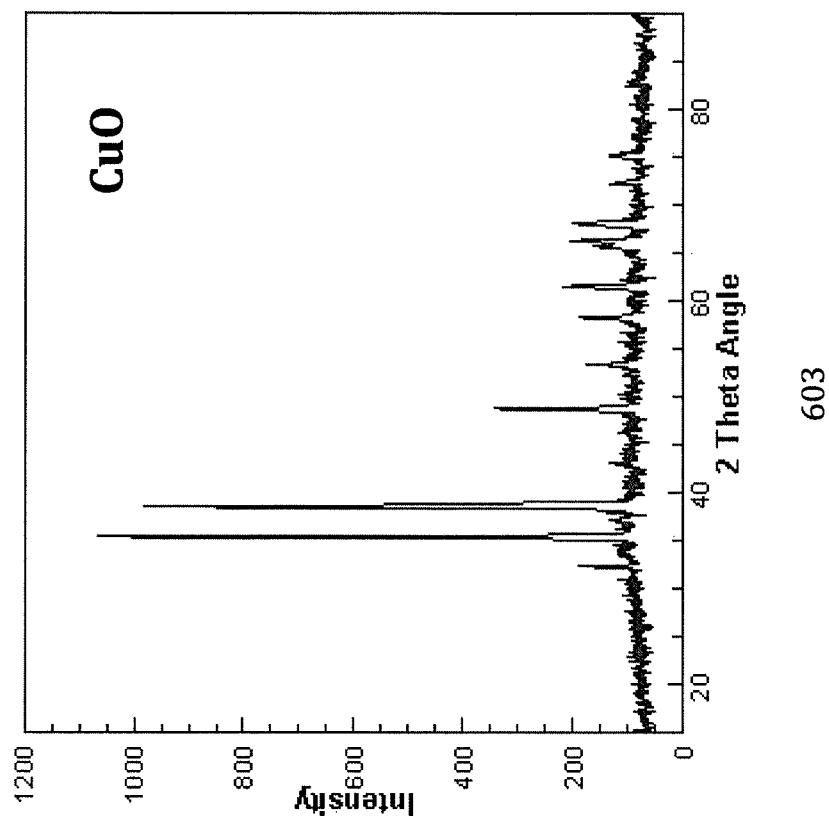
FIG. 6 illustrates micrographs and an x-ray diffraction plot of CuO nanofibers from electrospinning of Cu—Ac/PVA (2:1) solution.
Figure 6:
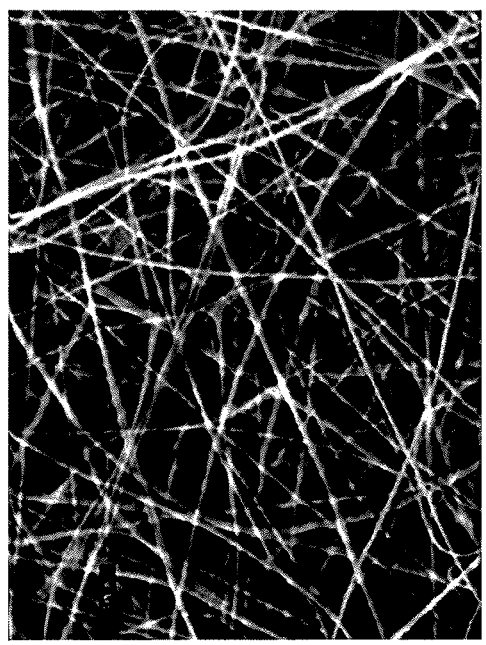
Figure 6:
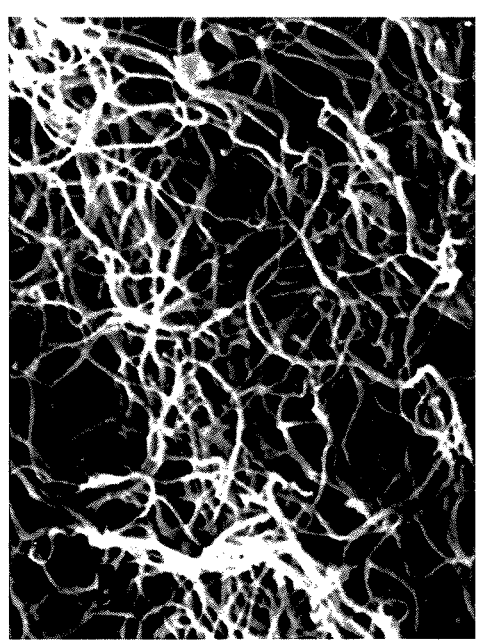
Figure 9:
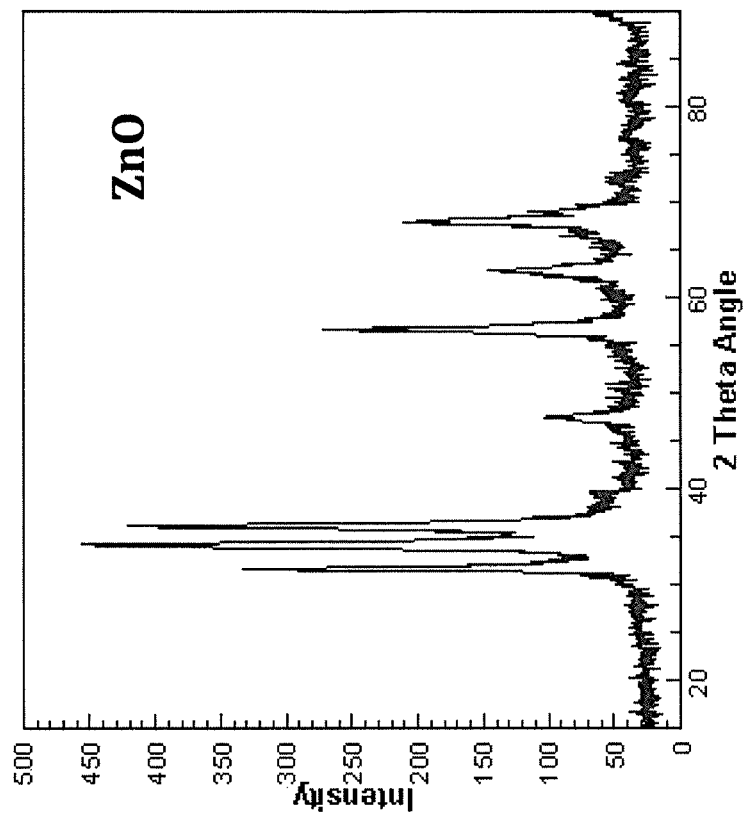
FIG. 9 illustrates micrographs and an x-ray diffraction plot of ZnO nanofibers from electrospinning of Zn—Ac/PVA (2:1) solution.
Figure 9:
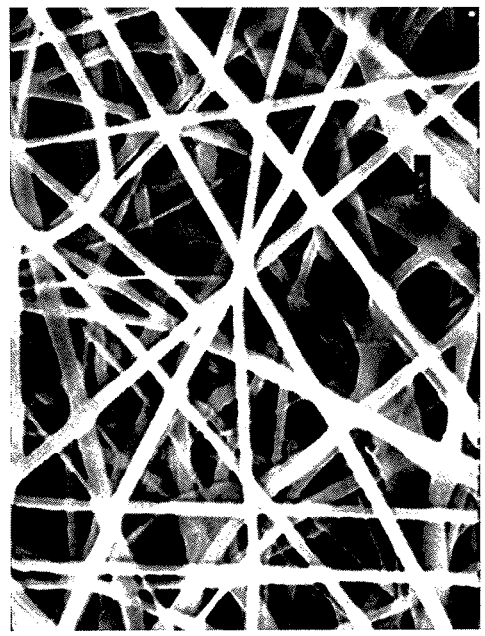
Figure 9:
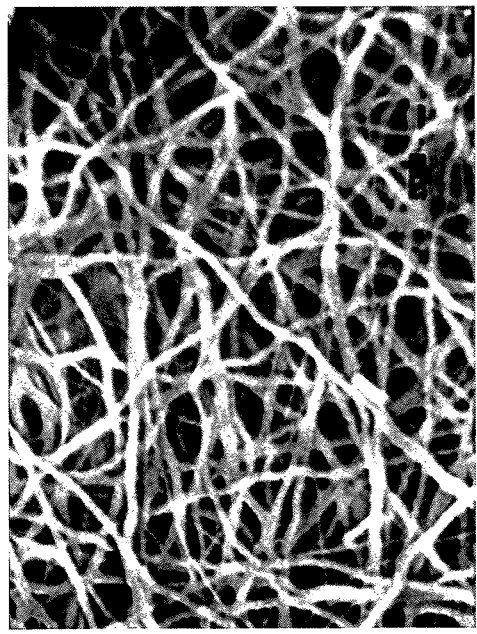
Figure 10:
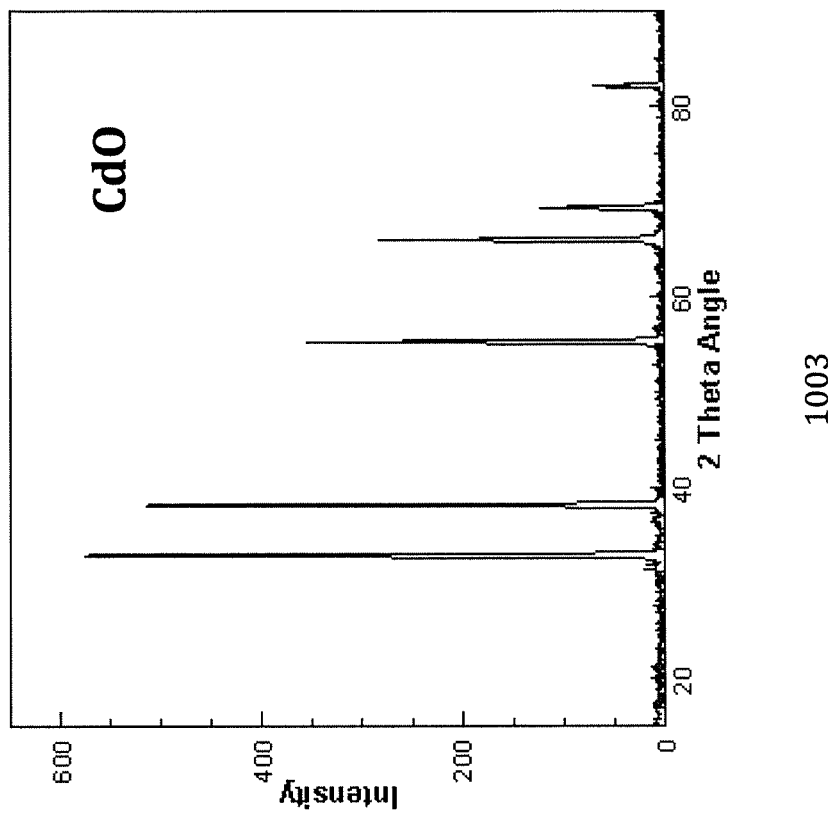
FIG. 10 illustrates micrographs and an x-ray diffraction plot of CdO nanofibers from electrospinning of Cd—Ac/PVA (2:1) solution.
Figure 10:
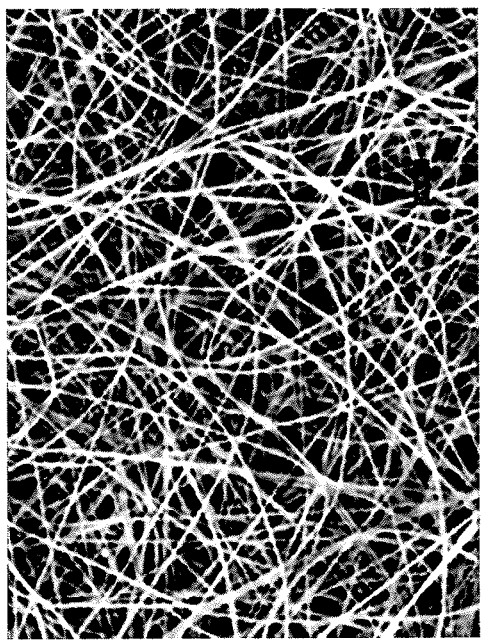
Figure 10:
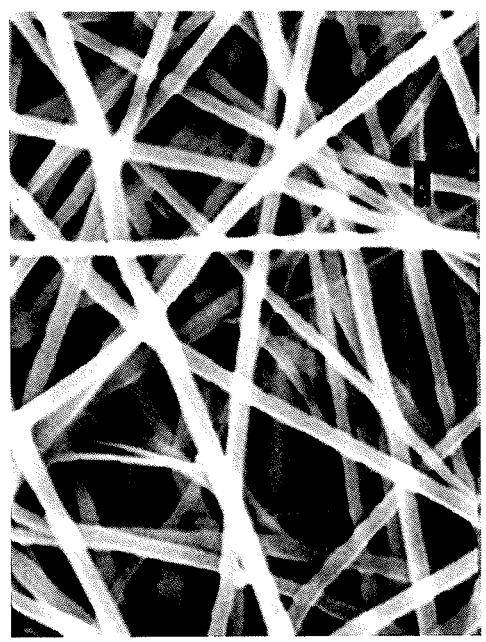
Figure 11:
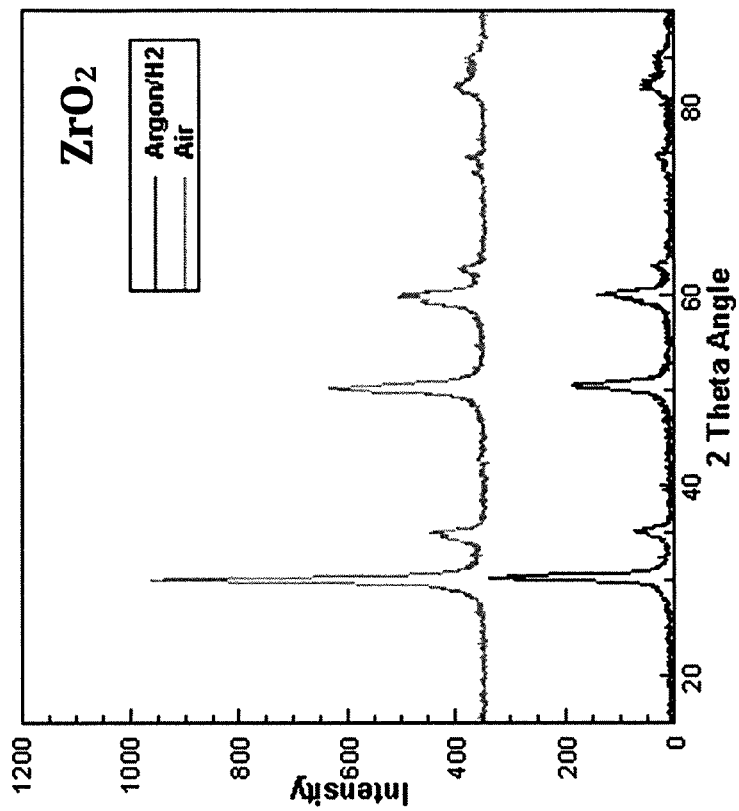
FIG. 11 illustrates micrographs and an x-ray diffraction plot of $ZrO_2$ nanofibers from electrospinning of Zr—Ac/PVA (2:1) solution.
Figure 11:
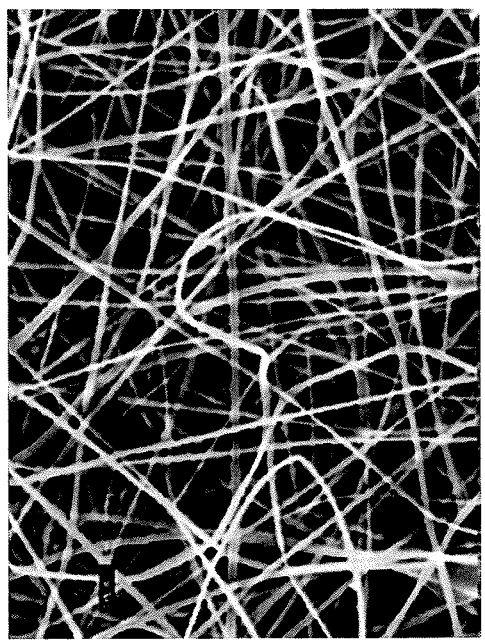
Figure 11:
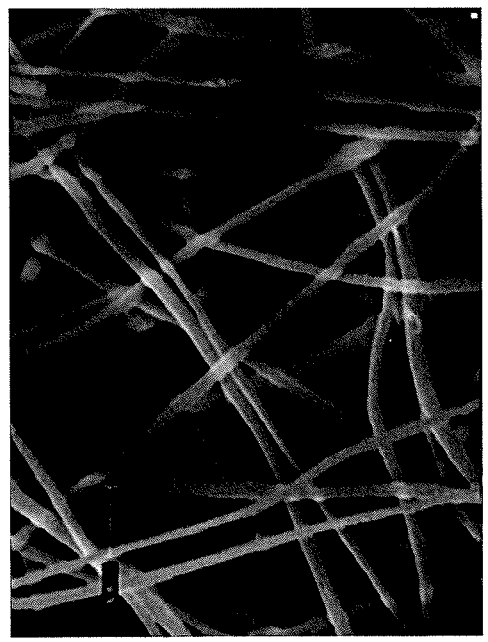

FIGS. 4, 6, 9, 10, and 11 illustrate metal precursor and metal oxide (e.g., metal oxide ceramic) nanofibers provided herein and/or as prepared according to the processes described herein. FIG. 4 illustrates nickel precursor nanofibers 401 having average diameters of 500-700 nm, and nickel oxide nanofibers 402, having average diameters of 300-500 nm, prepared from the nickel precursor nanofibers 401 after treatment at 600° C. for 2 hours in air. FIG. 4 also illustrates the crystal x-ray diffraction pattern 403 of the nickel oxide nanofibers 402. FIG. 6 illustrates copper precursor nanofibers 601 having average diameters of 600-800 nm, and copper oxide nanofibers 602, having average diameters of 200-600 nm, prepared from the copper precursor nanofibers 601 after treatment at 600° C. for 2 hours in air. FIG. 6 also illustrates the crystal x-ray diffraction pattern 603 of the copper oxide nanofibers 602. FIG. 9 illustrates zinc precursor nanofibers 901 having average diameters of 500-1000 nm, and zinc oxide nanofibers 902, having average diameters of 400-700 nm, prepared from the zinc precursor nanofibers 901 after treatment at 600° C. for 2 hours in air. FIG. 9 also illustrates the crystal x-ray diffraction pattern 903 of the zinc oxide nanofibers 902. FIG. 10 illustrates cadmium precursor nanofibers 1001 having average diameters of 800-1200 nm, and cadmium oxide nanofibers 1002, having average diameters of 600-900 nm, prepared from the cadmium precursor nanofibers 1001 after treatment at 800° C. for 2 hours in air. FIG. 10 also illustrates the crystal x-ray diffraction pattern 1003 of the cadmium oxide nanofibers 1002. FIG. 11 illustrates zirconium precursor nanofibers 1101 having average diameters of 800-1000 nm, and zirconia nanofibers 1102, having average diameters of 300-600 nm, prepared from the zirconium precursor nanofibers 1101 after treatment at 800° C. for 2 hours in air. FIG. 11 also illustrates the crystal x-ray diffraction pattern 1103 of the zirconia nanofibers 1102.

Alloy Nanofibers

Provided in various embodiments herein are pure metal alloy nanofibers, nanofibers comprising metal alloy, or nanofibers substantially comprised of metal alloy. The metal alloy is any suitable metal alloy including: transition metal, alkali metal, alkaline earth metal, post-transition metal, lanthanide, or actinide, additionally, germanium (Ge), antimony (Sb) and polonium (Po), and silicon (Si). In some embodiments, the alloy is a metal-metal alloy. In other embodiments, the alloy is a metal-non-metal alloy. In certain embodiments, metal-metal alloys are prepared by utilizing a first metal precursor, a second metal precursor, and optional further metal precursors in a fluid stock in a process described herein described herein (e.g., evenly dispersing the at least two metal precursors), wherein the first and second metal precursors comprise different metals. In some embodiments, metal-non-metal alloys are prepared by utilizing a metal precursor and a non-metal stock (e.g., powder of the non-metal material) in a fluid stock in a process described herein described herein (e.g., evenly dispersing the metal precursor and the non-metal stock in the fluid stock), wherein the first and second metal precursors comprise different metals.

In various embodiments, metal alloys optionally comprise any metal discussed above for metal nanofibers (as the metal alloy nanofibers discussed are considered within the scope of metal nanofibers for the purposes of this disclosure). In addition, for metal-non-metal alloys, any suitable non-metal material, such as boron, carbon, phosphorus, sulfur, selenium, or the like, may be utilized. For example, FIG. 25 illustrates a lead selenium metal-non-metal alloy prepared according to the disclosure provided herein.

Provided in various embodiments herein are metal alloy nanofibers, nanofibers comprising metal alloy, or nanofibers substantially comprised of metal alloy. In some embodiments, the metal alloy nanofiber comprises about 99%, about 98%, about 97%, about 96%, about 95%, about 90%, about 80%, and the like of metal alloy by mass. In some embodiments, the metal alloy nanofiber comprises at least about 99%, at least about 98%, at least about 97%, at least about 96%, at least about 95%, at least about 90%, at least about 80%, and the like of ceramic by mass (e.g., elemental mass). In other embodiments, metal alloy nanofibers provided herein comprise at least 50%, at least 60%, at least 70%, or at least 75% metal alloy by mass (e.g., elemental mass). In specific embodiments, metal alloy nanofibers provided herein comprise at least 80% metal alloy by mass. In more specific embodiments, metal alloy nanofibers provided herein comprise at least 90% metal alloy by mass. In still more specific embodiments, metal alloy nanofibers provided herein comprise at least 95% metal alloy by mass.

In some embodiments, the metal alloy nanofibers comprise low amounts of carbon and/or oxygen as discussed herein for metal nanofibers. In certain embodiments, wherein the metal-non metal alloy is a metal-carbon alloy, at least 50%, at least 60%, at least 70%, or at least 75% metal and carbon by mass (e.g., elemental mass). In specific embodiments, metal alloy nanofibers provided herein comprise at least 80% metal and carbon by mass. In more specific embodiments, metal alloy nanofibers provided herein comprise at least 90% metal and carbon by mass. In still more specific embodiments, metal alloy nanofibers provided herein comprise at least 95% metal and carbon by mass.

Exemplary metal alloys include, but are not limited to CdSe, CdTe, PbSe, PbTe, FeNi (perm alloy), Fe—Pt intermetallic compound, Pt—Pb, Pt—Pd, Pt—Bi, Pd—Cu, and Pd—Hf. Methods for producing metal alloy nanofibers are disclosed herein and optionally include electrospinning a fluid stock comprising a mixture of the metal precursors of the alloy and calcinating under reducing conditions. For example, a CdSe alloy nanofiber is produced by electrospinning a fluid stock comprising a mixture of cadmium acetates and selenium acetates, followed by calcinating under reducing conditions.

In one aspect, in addition to metal, ceramic, or alloy nanofibers, a nanofiber of virtually any material is produced using the methods described herein (e.g., as long as the material is convertible from suitable precursors distributed substantially evenly and in a high proportion of the fluid stock). In some embodiments, the nanofiber is a calcium phosphate (Ca—P) nanofiber. In some embodiments, the methods of the present disclosure produce high quality Ca—P nanofibers, optionally wherein the nanofiber is at least 50 μm long on average.

In some embodiments, the methods of the present disclosure are combined with other methods to produce yet more embodiments. For example, the nanofibers undergo further modifications following their synthesis. As disclosed in U.S. patent application Ser. No. 12/439,398 for example, biologically functional additives are added to calcium phosphate nanofibers for culturing bone and dental cells or as implants to treat bone, dental or periodontal diseases and defects.

In some embodiments, the nanofibers are surface-modified. For example, enzymes are immobilized on the nanofiber surface to create a biological catalyst. In another example, doping processes from the semiconductor industry are employed to introduce impurities into a pure semiconductor nanofiber (e.g., for the purpose of modulating its electrical properties).

In one aspect, described herein is a nanofiber comprising a segment comprising a continuous matrix of a metal, a metal oxide, a metal alloy, a ceramic, or a combination thereof. In some instances, a continuous matrix is conductive from one end of the segment to the other end of the segment. In some instances, a continuous matrix defines a single unified volume of the metal, metal oxide, metal alloy, ceramic, or a combination thereof. In some instances, the metal, metal oxide, metal alloy, ceramic, or a combination thereof is in contact with metal, metal oxide, metal alloy, ceramic, or a combination thereof all along the length of the continuous matrix. The segment or plurality of segments comprise any suitable proportion of the nanofiber, including about 5%, about 10%, about 20%, about 30%, about 40%, about 50%, about 60%, about 70%, about 80%, about 90%, about 95%, and the like of the length of the nanofiber. In some embodiments, the segment or segments comprise at most 5%, at most 10%, at most 20%, at most 30%, at most 40%, at most 50%, at most 60%, at most 70%, at most 80%, at most 90%, at most 95%, and the like of the length of the nanofiber. In some embodiments, the segment or segments comprise at least 5%, at least 10%, at least 20%, at least 30%, at least 40%, at least 50%, at least 60%, at least 70%, at least 80%, at least 90%, at least 95%, and the like of the length of the nanofiber. In specific embodiments, a continuous matrix described herein comprises less than half of the mass of the nanofiber, but forms the continuous matrix that runs along the length of the nanofiber. In some instances, the continuous matrix runs along at least 50% the length of the nanofiber (e.g., on average for populations of nanofibers). In specific instances, the continuous matrix runs along at least 70% the length (e.g., on average) of the nanofiber(s). In more specific instances, the continuous matrix runs along at least 80% the length (e.g., on average) of the nanofiber(s). In still more specific embodiments, the continuous matrix runs along at least 90% of the length (e.g., on average) of the nanofiber(s). In yet more specific embodiments, the continuous matrix runs along at least 95% of the length (e.g., on average) of the nanofiber(s).

Composite & Hybrid Nanofibers

Previous methods for producing nanofibers (e.g., the sol-gel method) do not generally produce nanofibers of a high enough quality to be any form other than a solid monolithic cylinder. In some instances, by employing the methods disclosed herein, the number and size of voids and defects in nanofibers are substantially reduced, allowing more complex geometries such as hollow nanofibers and composite or hybrid nanofibers made of more than one material. In some instances, the hybrid or hollow nanofibers are suitably long and continuous (i.e., high quality).

In some embodiments, provided herein is a composite nanofiber comprising a first material and a second material. In some embodiments, at least one or both of the first and second materials comprise a metal or metal oxide (e.g., metal oxide ceramic).

In certain embodiments, the first material forms a continuous matrix of the nanofiber. In specific embodiments, the first material is a metal, a ceramic, or carbon. In more specific embodiments, the first material is a metal or carbon and the second material is a metal, metal oxide (e.g., metal oxide ceramic), or ceramic. In some embodiments, the first material is a ceramic and the second material is a metal, metal oxide, or ceramic. In specific embodiments, the first material is a ceramic and the second material is a metal.

In some embodiments, the first material forms a continuous matrix and the second material forms isolated domains within the nanofiber. In other embodiments, both the first and second materials form continuous matrices within the nanofiber (e.g., a layered hybrid nanofiber, such as a layered hybrid nanofiber formed via coaxial electrospinning—a layered coaxial hybrid nanofiber). In other embodiments, the first and second materials form different (e.g., alternating) segments of the nanofiber (i.e., alternating segments along the length of the nanofiber).

Described herein are methods for producing hybrid nanofibers, methods for using hybrid nanofibers, devices comprising hybrid nanofibers, and the hybrid nanofibers themselves. As disclosed herein, hybrid nanofibers are useful in flexible solar cells for example. "Hybrid" is used interchangeably with "composite" and means that the nanofiber comprises at least two materials. The materials are found in distinct locations on or in the nanofiber. Such locations are arranged in any suitable geometric matter.

One exemplary geometry is a fiber with various annular rings or layers made of different materials. In some embodiments, each layer is coaxial. In some embodiments, coaxial hybrid nanofibers are produced by the methods described herein (e.g., comprising at least two layers—one of which may form a core of the nanofiber, the other a layer at least partially surrounding the core). In some embodiments, the spinneret is modified to comprise a first conduit containing a first fluid stock surrounded by a second conduit containing a second fluid stock (FIG. 35). In some instances, the fluid stocks are drawn or forced through the conduits. Such a configuration produces an annular fluid jet with the second fluid stock surrounding the first fluid stock. In some embodiments, as the jet dries and is then calcified, the first and second fluid stocks do not substantially mix, so are converted into different materials in the nanofiber.

In some embodiments of a hybrid nanofiber (e.g., including a coaxial nanofiber), various layers are any material suitable. In some embodiments, the coaxial layers are referred to in any manner unless the context clearly indicates otherwise. For example, for a nanofiber consisting of two coaxial layers, the first layer may surround the second layer or the second layer may surround the first layer. In some embodiments, the first coaxial layer comprises a ceramic. In some embodiments the second coaxial layer comprises a ceramic. In some embodiments, the first coaxial layer comprises a metal. In some embodiments the second coaxial layer comprises a metal. In various embodiments, the hybrid nanofiber is metal-on-metal, ceramic-on-metal, ceramic-on-ceramic, or metal-on-ceramic. In some embodiments, the hybrid nanofiber has at least 3 components, including any integer with all types of materials in all types of combinations.

In various embodiments, composite nanofibers comprise metal, metal oxide, and/or ceramic, as disclosed herein. The metals, metal oxides, and/or ceramics used in such composite nanofibers include any such metals, metal oxides, or ceramics described herein for metal (e.g., single metal or alloys), metal oxide (e.g., metal oxide ceramics), and ceramic nanofibers. In some embodiments, a metal like Ag, Cu, Ni, Fe, Co, Pb, Au, Sn, Al, is hybridized with a ceramic like $Al_2O_3$, $ZrO_2$, $Fe_2O_3$, CuO, NiO, ZnO, CdO, $SiO_2$, $TiO_2$, $V_2O_5$, $VO_2$, $Fe_3O_4$, SnO, $SnO_2$, CoO, $CoO_2$, $Co_3O_4$, $HfO_2$, $BaTiO_3$, $SrTiO_3$, $BaSrTiO_3$. In some embodiments, a first co-axial layer comprises Ni or Fe. In some embodiments, a second co-axial layer comprises $Al_2O_3$, $ZrO_2$, $SiO_2$ or $TiO_2$. In one embodiment, a first co-axial layer comprises Ni and a second co-axial layer comprises $ZrO_2$. In one embodiment, a first coaxial layer comprises $Al_2O_3$, and a second co-axial layer comprises ITO. In another embodiment, a first coaxial layer comprises $ZrO_2$ and a second co-axial layer comprises ZnO.

Complex geometries other than coaxial fibers are also described herein. For example in one arrangement, a first and a second material are disposed along different parts of the length of the nanofiber. In some embodiments, such a nanofiber is produced by alternating the fluid stock between a first fluid stock comprising a first material and a second fluid stock comprising a second material in the electrospinning process. In such an embodiment, upon calcination a nanofiber is produced that alternates along its length between a first material and a second material. The first and second materials are any suitable material, including ceramics and metals.

In various embodiments, a composite nanofiber comprises a metal-metal hybrid, a metal-ceramic hybrid, or the like. In some embodiments, the nanofiber is a hybrid of both metal and ceramic. In certain embodiments, the mass percentages of the total mass of the metal and ceramic components of the nanofiber are added (to the extent that either or both are present) and comprise about 99.99%, about 99.95%, about 99.9%, about 99%, about 98%, about 97%, about 96%, about 95%, about 90%, about 80%, and the like of the nanofiber. In other embodiments, the sum of the metal and ceramic components of the nanofiber are at least about 99.99%, at least about 99.95%, at least about 99.9%, at least about 99%, at least about 98%, at least about 97%, at least about 96%, at least about 95%, at least about 90%, at least about 80%, and the like of the nanofiber. In other embodiments, the total mass of the metal and ceramic components (to the extent that either or both are present) comprise at least 30%, at least 40%, at least 50%, at least 60%, at least 70%, or the like. In some instances, these lower metal/ ceramic content composite nanofibers are present nanofibers comprising a continuous matrix that is neither metal nor ceramic.

Figure 16:
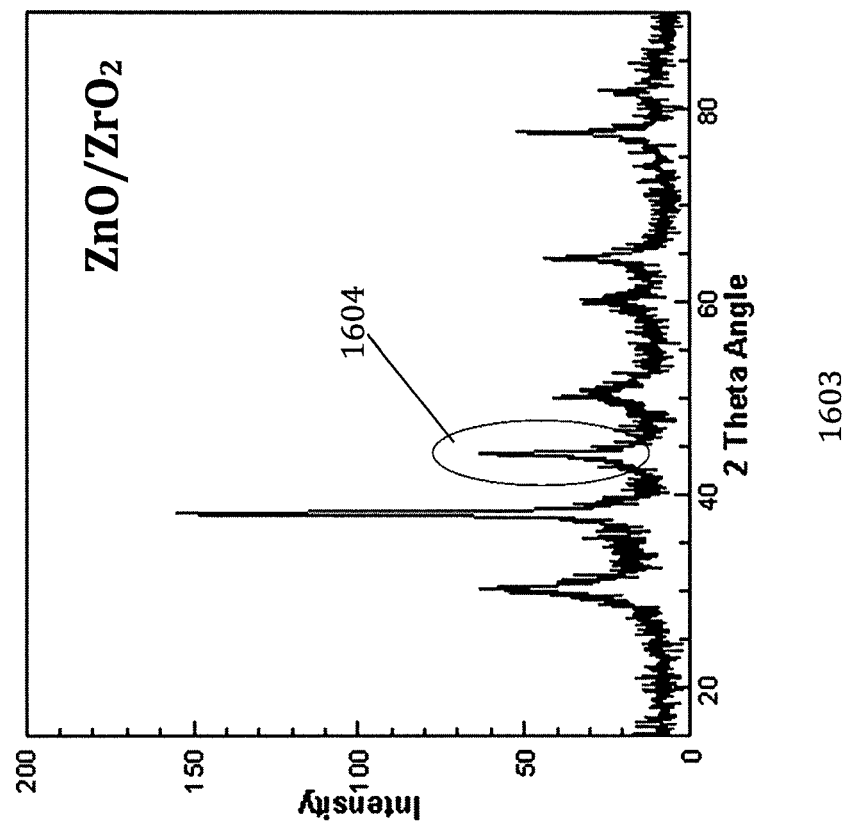
FIG. 16 illustrates micrographs and an x-ray diffraction plot of ZnO/$ZrO_2$ hybrid nanofibers.
Figure 16:
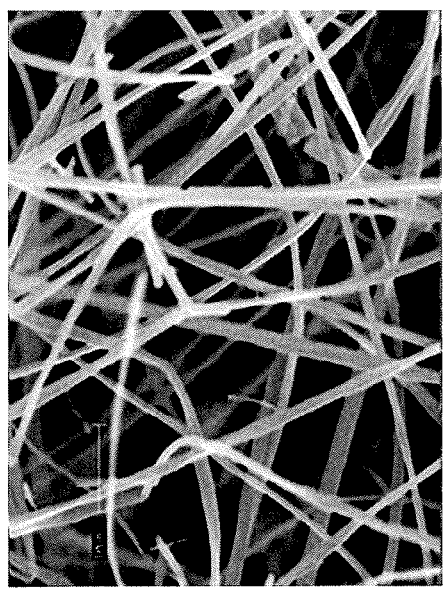
Figure 16:
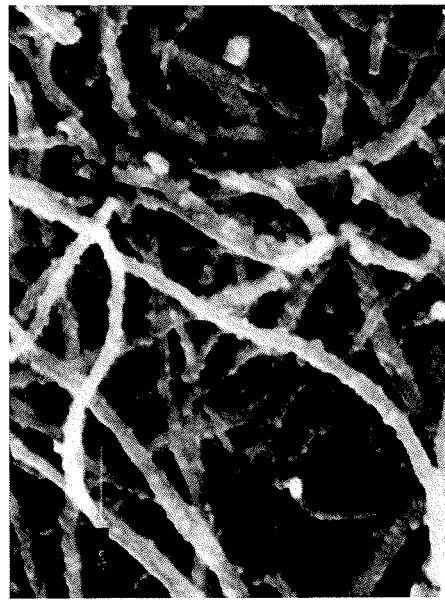
Figure 17:
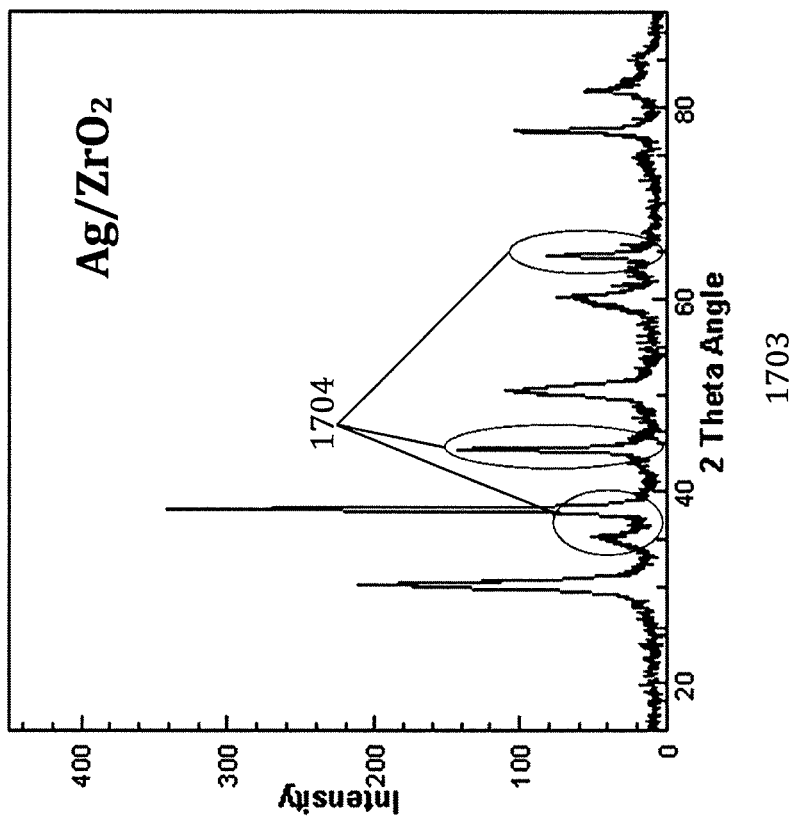
FIG. 17 illustrates micrographs and an x-ray diffraction plot of Ag/$ZrO_2$ hybrid nanofibers.
Figure 17:
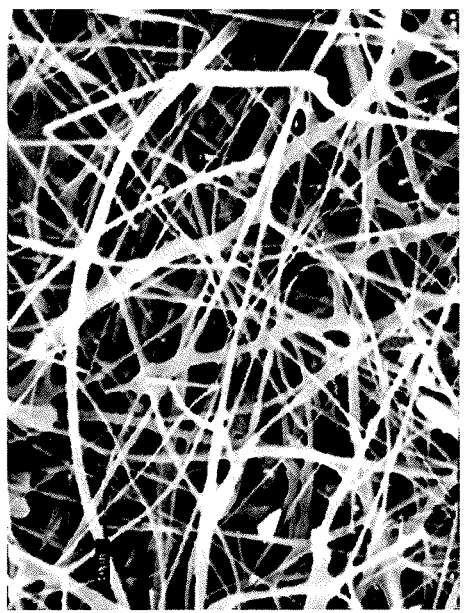
Figure 17:
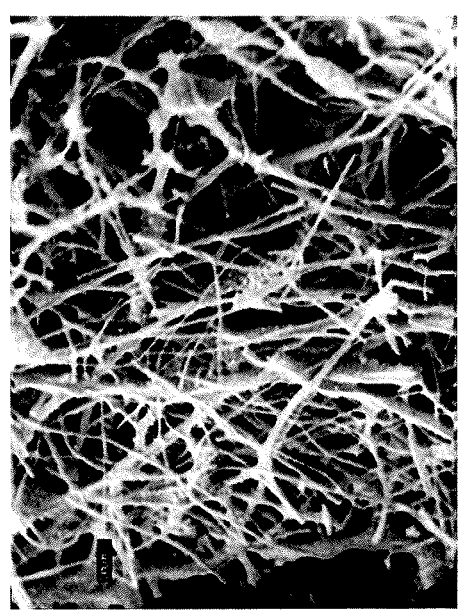
Figure 18:
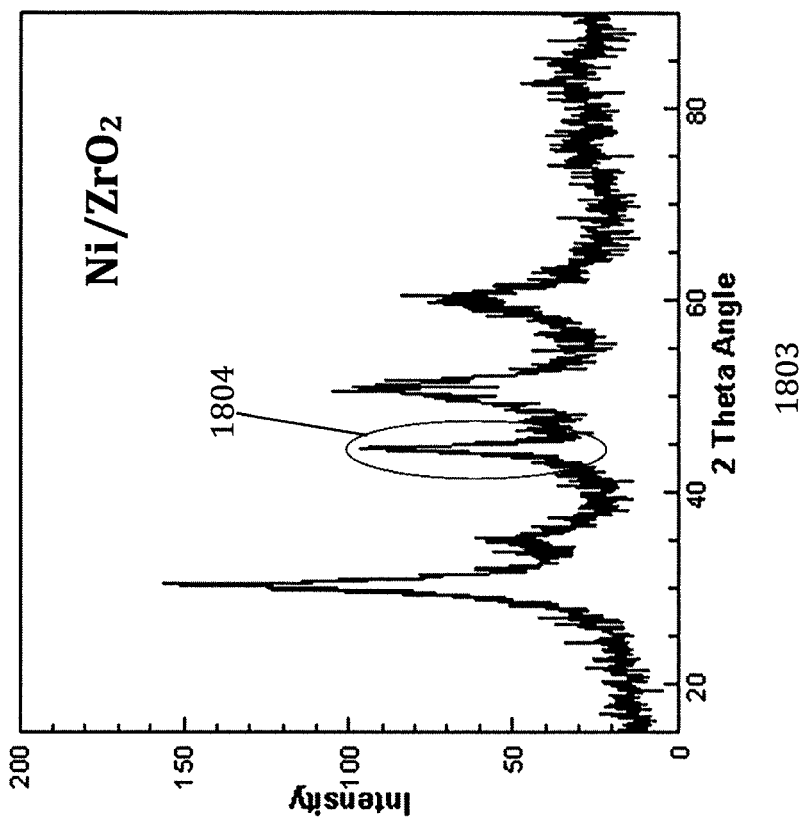
FIG. 18 illustrates micrographs and an x-ray diffraction plot of Ni/$ZrO_2$ hybrid nanofibers.
Figure 18:
Figure 18:
Figure 19:
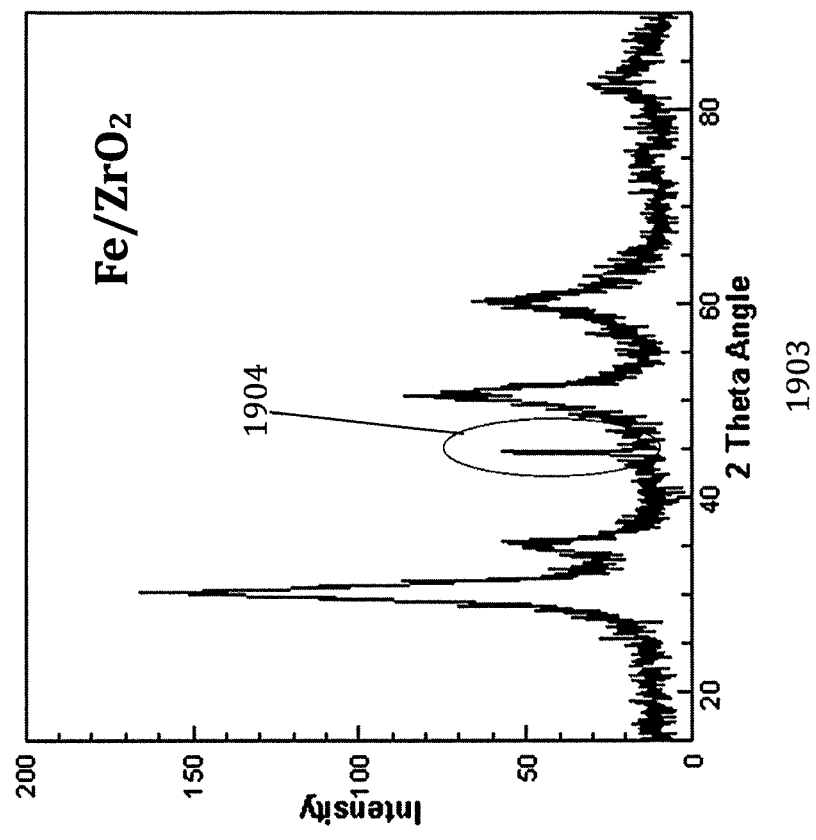
FIG. 19 illustrates micrographs and an x-ray diffraction plot of Fe/$ZrO_2$ hybrid nanofibers.
Figure 19:
Figure 19:
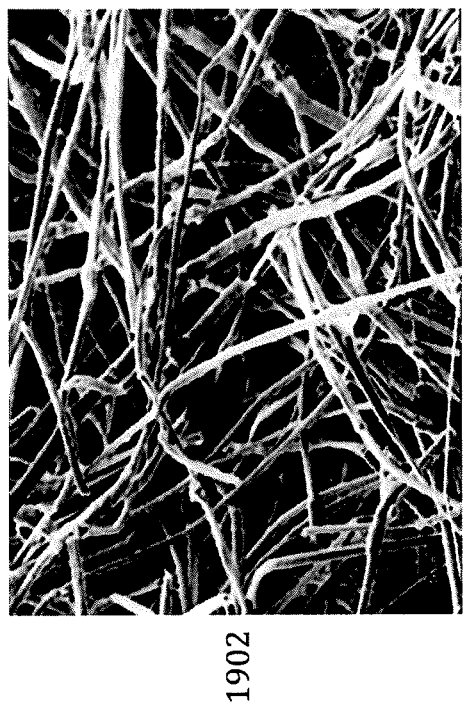
Figure 20:
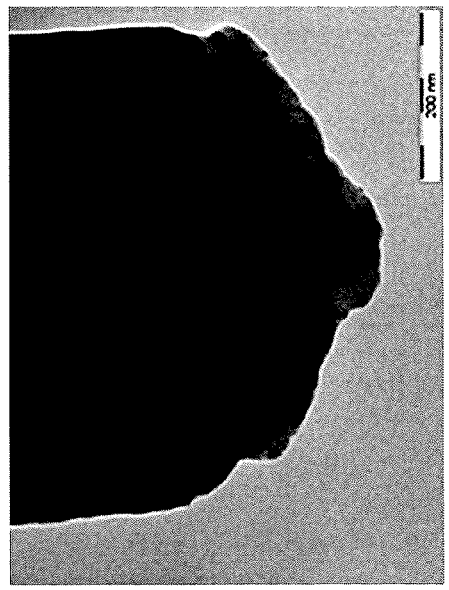
FIG. 20 illustrates TEM micrographs of $ZrO_2$ hybrid (nanocomposite) nanofibers containing various metal and metal oxides (ZnO, Ni, Ag, and Fe).
Figure 20:
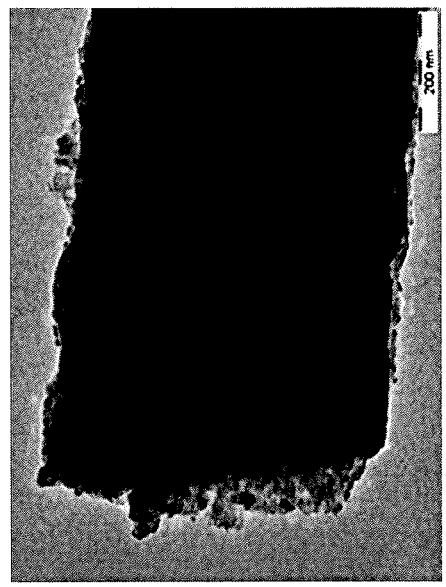
Figure 20:
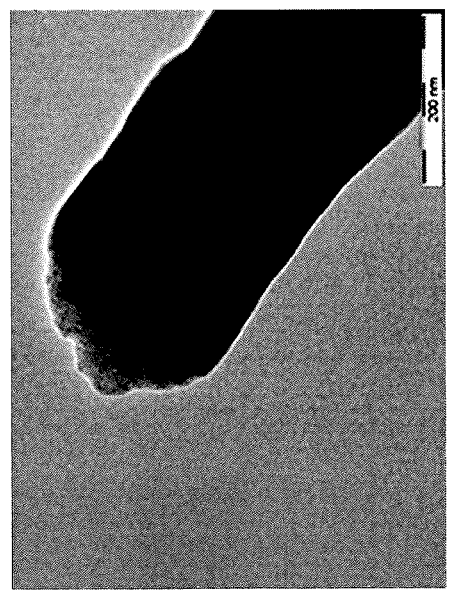
Figure 20:
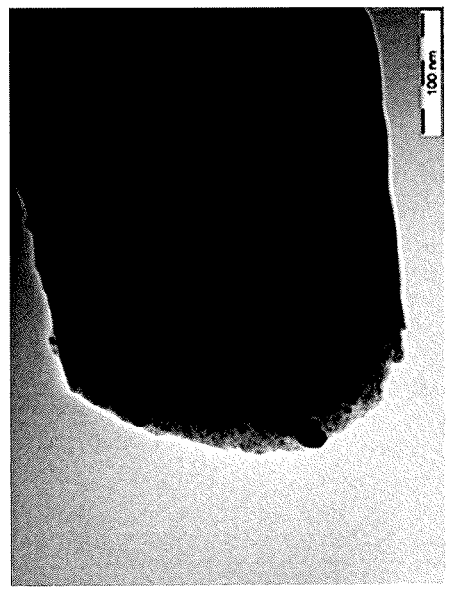
Figure 21:
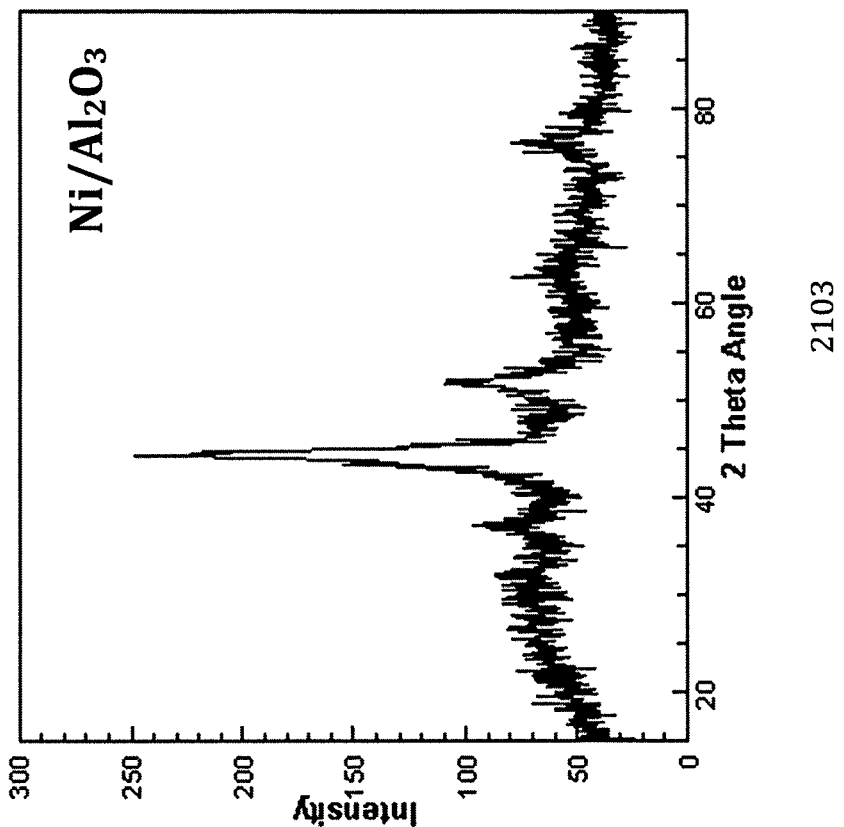
FIG. 21 illustrates micrographs and an x-ray diffraction plot of Ni/$Al_2O_3$ hybrid nanofibers.
Figure 21:
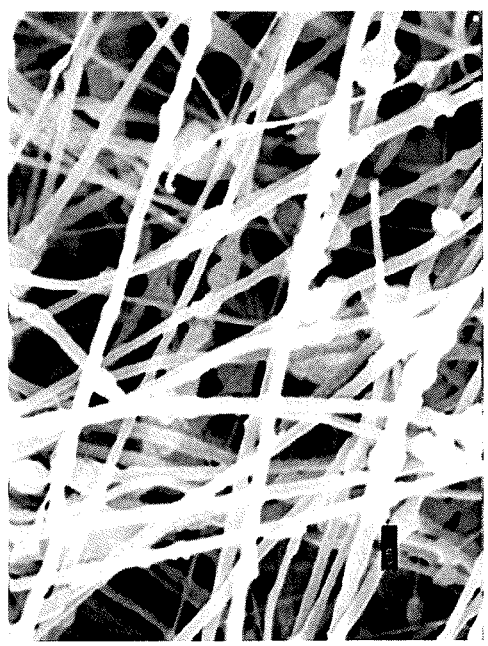
Figure 21:
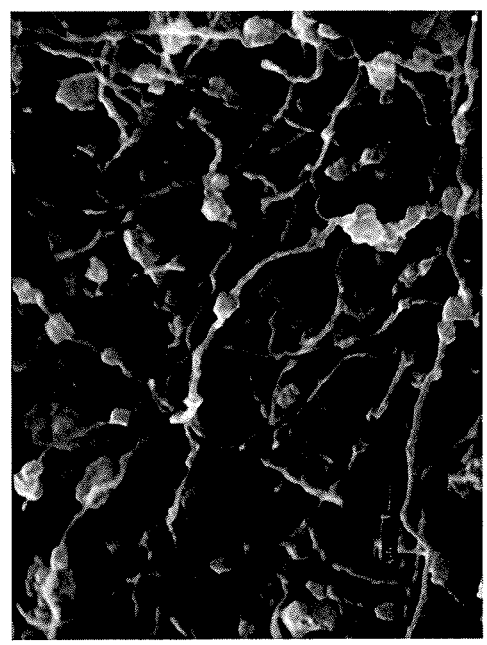
Figure 31:
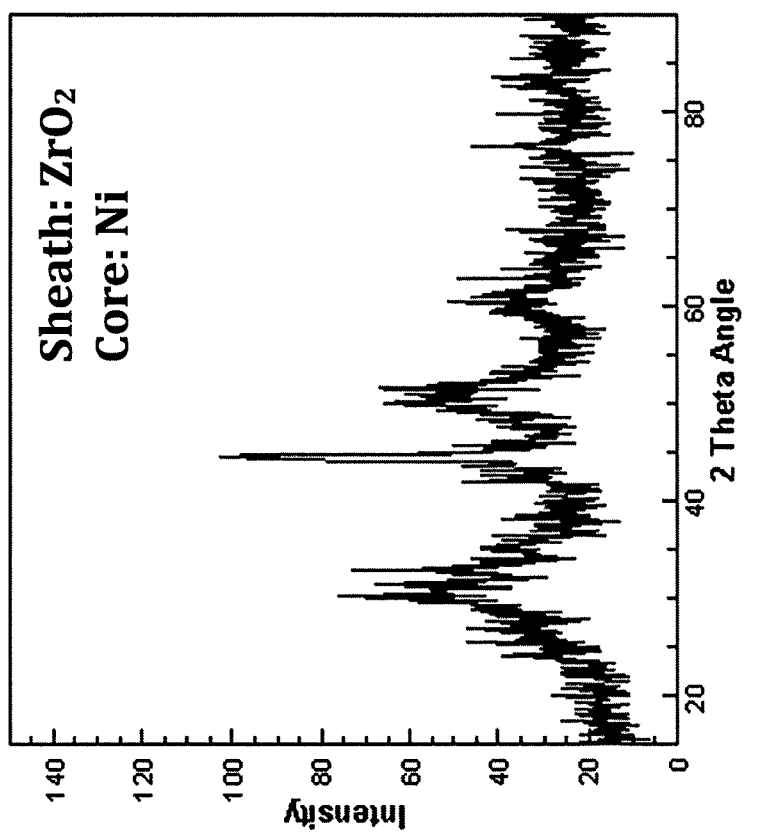
FIG. 31 illustrates micrographs and an x-ray diffraction plot of Ni/$ZrO_2$ hybrid nanofibers.
Figure 31:
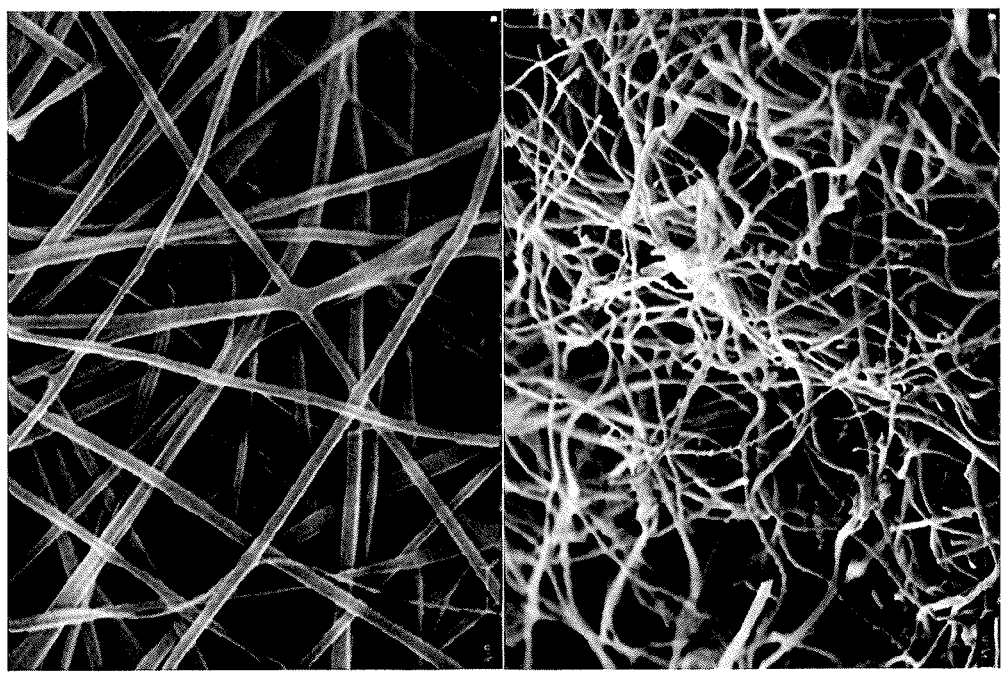
Figure 32:
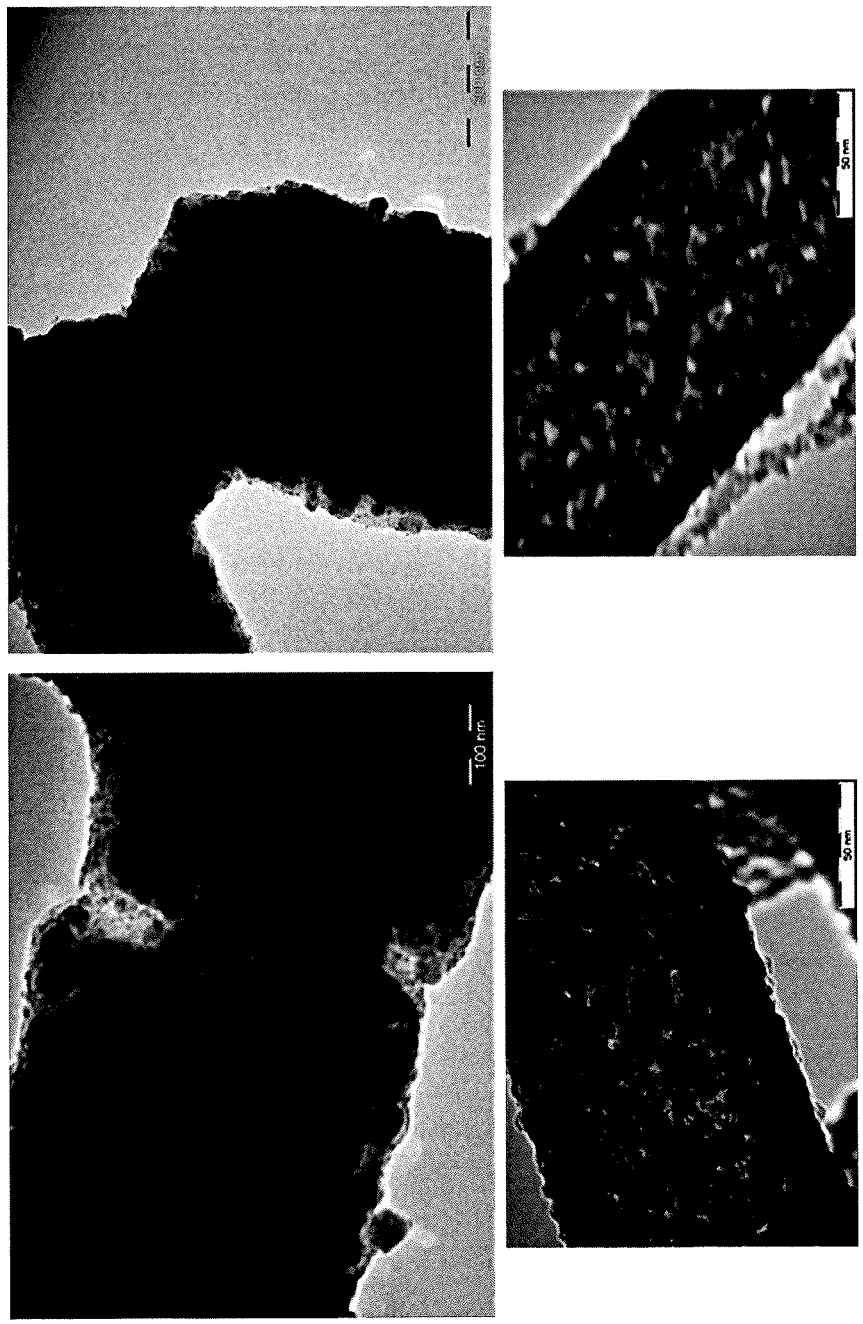
FIG. 32 illustrates TEM micrographs of Ni/$ZrO_2$ hybrid nanofibers.
Figure 33:
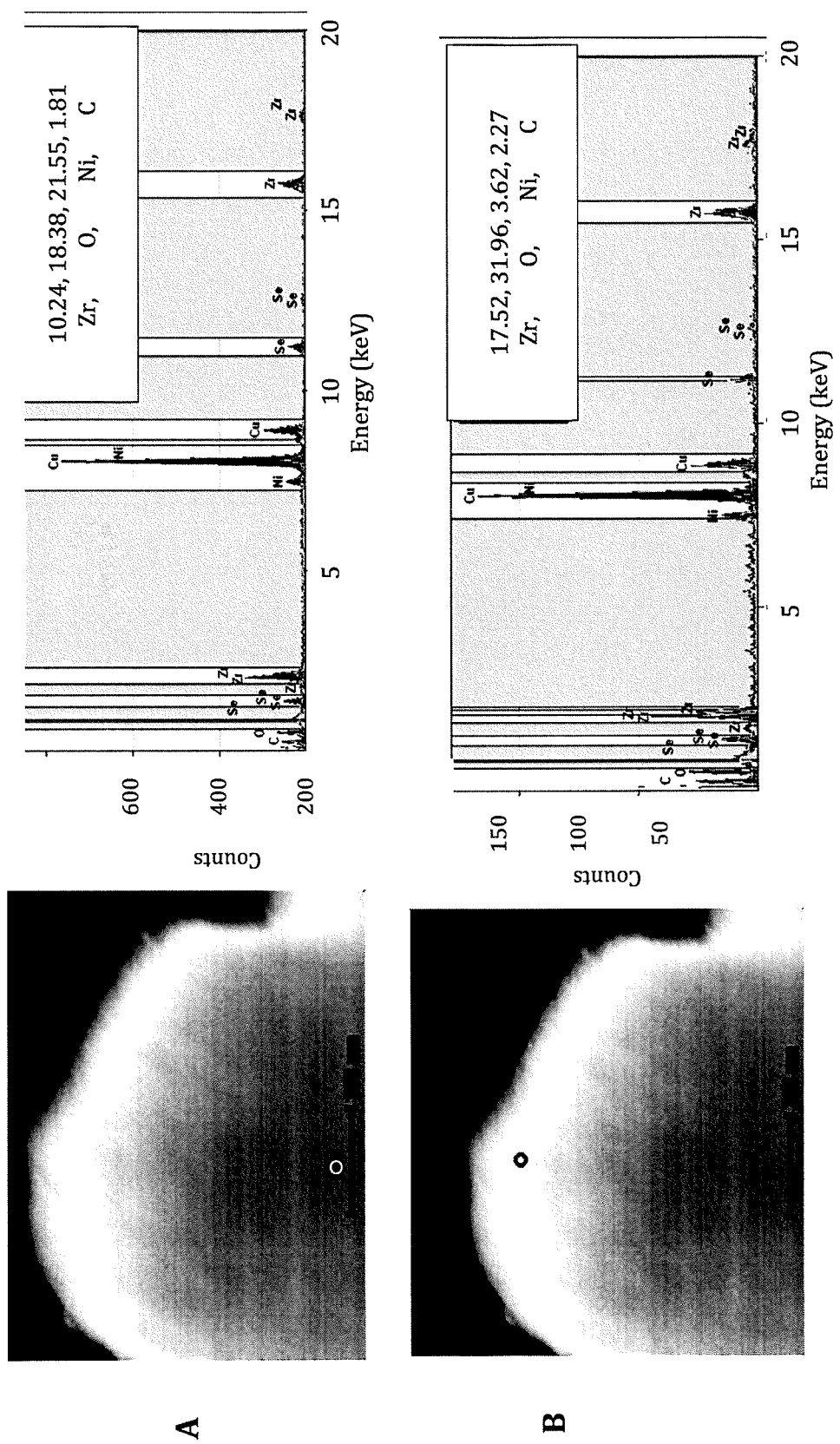
FIG. 33 illustrates elemental analysis of Ni/$ZrO_2$ hybrid nanofibers.

FIGS. 16-21 and 31-33 illustrate metal precursor and metal composite/hybrid nanofibers provided herein and/or as prepared according to the processes described herein. FIG. 16 illustrates zirconium-zinc precursor nanofibers 1601 (i.e., nanofibers comprising zirconium precursor, zinc precursor, and polymer) having average diameters of 600-1000 nm, and zirconia-zinc oxide composite nanofibers 1602, having average diameters of 300-600 nm, prepared from the precursor nanofibers 1601 after treatment at 600° C. for 2 hours in argon. FIG. 16 also illustrates the crystal x-ray diffraction peaks for zirconia 1603 and zinc oxide 1604 for the composite nanofibers 1602. FIG. 17 illustrates zirconium-silver precursor nanofibers 1701 having average diameters of 700-900 nm, and zirconia-silver composite nanofibers 1702, having average diameters of 400-700 nm, prepared from the precursor nanofibers 1701 after treatment at 800° C. for 2 hours in an argon/hydrogen mixture. FIG. 17 also illustrates the crystal x-ray diffraction peaks for zirconia 1703 and silver 1704 for the composite nanofibers 1702. FIG. 18 illustrates zirconium-nickel precursor nanofibers 1801 having average diameters of 800-1200 nm, and zirconia-nickel composite nanofibers 1802, having average diameters of 600-800 nm, prepared from the precursor nanofibers 1801 after treatment at 600° C. for 2 hours in argon. FIG. 18 also illustrates the crystal x-ray diffraction peaks for zirconia 1803 and nickel 1804 for the composite nanofibers 1802. FIG. 19 illustrates zirconium-iron precursor nanofibers 1901 having average diameters of 600-1000 nm, and zirconia-iron composite nanofibers 1902, having average diameters of 400-700 nm, prepared from the precursor nanofibers 1901 after treatment at 600° C. for 2 hours in argon. FIG. 19 also illustrates the crystal x-ray diffraction peaks for zirconia 1903 and iron 1904 for the composite nanofibers 1902. FIG. 20 further illustrates TEM images for such nanocomposites. FIG. 21 illustrates aluminum-nickel precursor nanofibers 2101 having average diameters of 400-1100 nm, and alumina-nickel composite nanofibers 2102, having average diameters of 150-700 nm, prepared from the precursor nanofibers 2101 after treatment at 600° C. for 2 hours in argon. FIG. 21 also illustrates the crystal x-ray diffraction peaks for nickel 2103 (and no peaks for the amorphous alumina) for the composite nanofibers 2102. FIG. 31 illustrates zirconium-nickel precursor nanofibers 3101 (nickel precursor+polymer core and zirconium precursor+polymer sheath) having average diameters of 450-700 nm, and zirconia-nickel layered composite nanofibers 3102, having average diameters of 300-550 nm, prepared from the precursor nanofibers 3101 after treatment at 600° C. for 2 hours in argon. FIG. 31 also illustrates the crystal x-ray diffraction peaks for zirconia and nickel 3103 for the layered (i.e., coaxial) composite nanofibers 3102 (nickel metal core and zirconia sheath). FIG. 32 illustrates TEM images for coaxial/layered layered nickel/zirconia nanofibers and FIG. 33 illustrates elemental analysis of coaxial/layered layered nickel/zirconia nanofibers. Panel A of FIG. 33 illustrates a hybrid nanofiber comprising a zirconium oxide layer outside of a nickel layer (core). Panel B of FIG. 33, illustrates the high content of zirconium and oxygen relative to nickel and carbon (in a ratio of about 18:32:4:2, respectively).

Hollow Nanofibers

The present disclosure encompasses methods for producing hollow nanofibers, methods for using hollow nanofibers, devices incorporating hollow nanofibers, and the hollow nanofibers themselves. As disclosed herein, hollow nanofibers are useful in lithium ion batteries in some instances.

In some embodiments, hollow nanofibers are produced using a spinneret that comprises a first conduit containing a first fluid surrounded by a second conduit containing a second fluid. In some instances, the first fluid is any fluid that does not become an integral part of the nanofiber (e.g., a gas). In some embodiments, the first fluid is inert.

In some embodiments, the first fluid is a gas, optionally air. In some instances, there are certain advantages to using a gas as the inner annular fluid as described in the gas-assisted electrospinning technique as disclosed in PCT Patent Application PCT/US2011/024894 ("Electrospinning apparatus and nanofibers produced therefrom"). In some embodiments, the gas jet accelerates and elongates the fluid stock stream emanating from the electrospinner, leading to thinner fibers. In some instances, the methods disclosed herein lead to thinner nanofibers (e.g., when using the gas-assisted method) and nanofibers that have few defects (e.g., so are therefore high quality).

In some embodiments, the first (inert) fluid is a liquid, optionally mineral oil for example. In embodiments where the outer fluid stock is aqueous, the mineral oil core does not mix with the electrospun fluid stock. In some embodiments, the mineral oil core is removed following calcination to leave a hollow nanofiber.

In some embodiments, hollow nanofibers are produced without an inert inner annular fluid. For example, a coaxial hybrid nanofiber is produced, then the inner annual material is removed, leaving a hollow nanofiber. The inner material is removed by any suitable technique including dissolving, subliming, evaporating, degrading, etching, or equivalents that result in a hollow nanofiber.

The hollow core of the nanofiber has any suitable diameter. In some embodiments, a given collection of nanofibers comprise nanofibers that have a distribution of fibers with various diameters of the hollow core. In some embodiments, a single nanofiber has a hollow core diameter that varies along its length. In some embodiments, certain fibers of a population or portions of a fiber exceed or fall short of the average inner diameter. In some embodiments, the diameter of the hollow core is on average about 1 nm, about 2 nm, about 3 nm, about 4 nm, about 5 nm, about 6 nm, about 7 nm, about 8 nm, about 9 nm, about 10 nm, about 15 nm, about 20 nm, about 40 nm, about 60 nm, about 80 nm, about 100 nm, about 200 nm, about 300 nm, about 400 nm, about 500 nm, and the like. In some embodiments, the diameter of the hollow core is on average at most about 1 nm, at most about 2 nm, at most about 3 nm, at most about 4 nm, at most about 5 nm, at most about 6 nm, at most about 7 nm, at most about 8 nm, at most about 9 nm, at most about 10 nm, at most about 15 nm, at most about 20 nm, at most about 40 nm, at most about 60 nm, at most about 80 nm, at most about 100 nm, at most about 200 nm, at most about 300 nm, at most about 400 nm, at most about 500 nm, and the like. In some embodiments, the diameter of the hollow core is on average at least about 1 nm, at least about 2 nm, at least about 3 nm, at least about 4 nm, at least about 5 nm, at least about 6 nm, at least about 7 nm, at least about 8 nm, at least about 9 nm, at least about 10 nm, at least about 15 nm, at most least 20 nm, at least about 40 nm, at least about 60 nm, at least about 80 nm, at least about 100 nm, at least about 200 nm, at least about 300 nm, at least about 400 nm, at least about 500 nm, and the like. In some embodiments, the diameter of the hollow core is on average between about 1 nm and 10 nm, between about 5 nm and 20 nm, between about 5 nm and 10 nm, between about 10 nm and 50 nm, between about 20 nm and 50 nm, between about 1 nm and 50 nm, between about 100 nm and 500 nm, and the like.

Nanofiber Properties

In one aspect, the nanofibers described herein are unique compositions of matter, having never before been described. In one aspect, described herein are nanofibers having certain novel properties. In various embodiments, these nanofibers have certain dimensions, aspect ratios, specific surface areas, porosities, conductivities, flexibilities, and the like that are beyond what was previously achievable. In some embodiments, the nanofibers described herein offer improvement upon devices that comprise the nanofibers. For example, the metal nanofibers described herein have an electrical conductivity that is at least 70% of the conductivity of the material when formed into a sheet in some instances. In some embodiments, high conductivity improves the function of solar cells based on the novel metal nanofibers.

In some embodiments, certain applications favor smaller diameter nanofibers (e.g., which are achieved without sacrificing quality by practicing the methods described herein). For example, gas-assisted electrospinning techniques are utilized to create thin nanofibers (i.e., by accelerating the jet stream of fluid stock leaving the electrospinner). In some embodiments, the diameter of the nanofiber changes upon calcination, optionally shrinking. In one example, copper nanofibers were 600 to 800 nm in diameter when electrospun and 300 to 500 nm after calcination. In some embodiments, the loading of precursor on the polymer affects the diameter of the nanofiber. In some embodiments, thicker nanofibers result from higher precursor loadings (e.g., because there is more precursor material converted into the nanofiber). Methods for measuring the diameter of a nanofiber include, but are not limited to microscopy, optionally transmission electron microscopy ("TEM") or scanning electron microscopy ("SEM").

In various embodiments, provided herein are nanofibers or processes for producing nanofibers having any suitable diameter. In some embodiments, a given collection of nanofibers comprise nanofibers that have a distribution of fibers of various diameters. In some embodiments, a single nanofiber has a diameter that varies along its length. In some embodiments, certain fibers of a population or portions of a fiber exceed or fall short of the average diameter. In some embodiments, the nanofiber has on average a diameter of about 20 nm, about 30 nm, about 40 nm, about 50 nm, about 60 nm, about 70 nm, about 80 nm, about 90 nm, about 100 nm, about 130 nm, about 150 nm, about 200 nm, about 250 nm, about 300 nm, about 400 nm, about 500 nm, about 600 nm, about 700 nm, about 800 nm, about 900 nm, about 1,000 nm, about 1,500 nm, about 2,000 nm and the like. In some embodiments, the nanofiber has on average a diameter of at most 20 nm, at most 30 nm, at most 40 nm, at most 50 nm, at most 60 nm, at most 70 nm, at most 80 nm, at most 90 nm, at most 100 nm, at most 130 nm, at most 150 nm, at most 200 nm, at most 250 nm, at most 300 nm, at most 400 nm, at most 500 nm, at most 600 nm, at most 700 nm, at most 800 nm, at most 900 nm, at most 1,000 nm, at most 1,500 nm, at most 2,000 nm and the like. In some embodiments, the nanofiber has on average a diameter of at least 20 nm, at least 30 nm, at least 40 nm, at least 50 nm, at least 60 nm, at least 70 nm, at least 80 nm, at least 90 nm, at least 100 nm, at least 130 nm, at least 150 nm, at least 200 nm, at least 250 nm, at least 300 nm, at least 400 nm, at least 500 nm, at least 600 nm, at least 700 nm, at least 800 nm, at least 900 nm, at least 1,000 nm, at least 1,500 nm, at least 2,000 nm and the like. In yet other embodiments, the nanofiber has on average a diameter between about 50 nm and about 300 nm, between about 50 nm and about 150 nm, between about 100 nm and about 400 nm, between about 100 nm and about 200 nm, between about 500 nm and about 800 nm, between about 60 nm and about 900 nm, and the like. In specific embodiments, nanofibers (e.g., metal, metal oxide, ceramic, and/or composite nanofibers described herein) have a (e.g., average) diameter of less than 1500 nm. In more specific embodiments, nanofibers (e.g., metal, metal oxide, ceramic, and/or composite nanofibers) described herein have a (e.g., average) diameter of 100 nm to 1000 nm. In some embodiments, nanofibers described herein (e.g., those comprising metal/metal oxide/ceramic) have a (e.g., average) diameter of 500 nm or less. In some embodiments, nanofibers described herein (e.g., those comprising metal/metal oxide/ ceramic) have a (e.g., average) diameter of 400 nm or less. In some embodiments, nanofibers described herein (e.g., those comprising metal/metal oxide/ceramic) have a (e.g., average) diameter of 200 nm to 500 nm. In other specific embodiments, precursor nanofibers described herein have a (e.g., average) diameter of less than 2000 nm. In more specific embodiments, precursor nanofibers described herein have a (e.g., average) diameter of 300 nm to 1500 nm.

In some embodiments, the nanofiber is long. In some instances, the methods of the present disclosure produce long nanofibers (e.g., because the high loading and uniform distribution of precursor creates nanofibers that are highly "continuous" or "coherent", meaning that they have few defects). In some embodiments, such high quality nanofibers are statistically more likely to be long because the probability is reduced that there is a defect along any particular length that is severe enough to define an end of the nanofiber. Methods for measuring the length of a nanofiber include, but are not limited to microscopy, optionally transmission electron microscopy ("TEM") or scanning electron microscopy ("SEM").

The nanofibers have any suitable length. In some instances, a given collection of nanofibers comprise nanofibers that have a distribution of fibers of various lengths. In some embodiments, certain fibers of a population exceed or fall short of the average length. In some embodiments, the nanofiber has an average length of about 20 µm, about 50 µm, about 100 µm, about 500 µm, about 1,000 µm, about 5,000 µm, about 10,000 µm, about 50,000 µm, about 100,000 µm, about 500,000 µm, and the like. In some embodiments, the nanofiber has an average length of at least about 20 µm, at least about 50 µm, at least about 100 µm, at least about 500 µm, at least about 1,000 µm, at least about 5,000 µm, at least about 10,000 µm, at least about 50,000 µm, at least about 100,000 µm, at least about 500,000 µm, and the like.

"Aspect ratio" is the length of a nanofiber divided by its diameter. In some instances, aspect ratio is a useful metric for quantifying the coherence of a nanofiber, with higher aspect ratios indicating that a nanofiber or population of nanofibers have few voids or defects. In some embodiments, aspect ratio refers to a single nanofiber. In some embodiments, aspect ratio refers to a plurality of nanofibers and is reported as a single average value (i.e., the aspect ratio being the average length of the nanofibers of a sample divided by their average diameter). In some instances, diameters and/or lengths are measured by microscopy. The nanofibers have any suitable aspect ratio. In some embodiments, the nanofiber has an aspect ratio of about 5, about 10, about $10^2$, about $10^3$, about $10^4$, about $10^5$, about $10^6$, about $10^7$, about $10^8$, about $10^9$, about $10^{10}$, about $10^{11}$, about $10^{12}$, and the like. In some embodiments the nanofiber has an aspect ratio of at least about 5, at least 10, at least $10^2$, at least $10^3$, at least $10^4$, at least $10^5$, at least $10^6$, at least $10^7$, at least $10^8$, at least $10^9$, at least $10^{10}$, at least $10^{11}$, at least $10^{12}$, and the like. In some embodiments, the nanofiber is of substantially infinite length and has an aspect ratio of substantially infinity. In specific embodiments, the aspect ratio (e.g., average aspect ratio) of nanofibers provided herein is at least 100. In more specific embodiments, the aspect ratio (e.g., average aspect ratio) of nanofibers provided herein is at least 1,000 (e.g., at least 5,000). In still more specific embodiments, the aspect ratio (e.g., average aspect ratio) of nanofibers provided herein is at least 10,000.

In some embodiments, the nanofibers have a high surface area. In some embodiments, the nanofiber is used as a catalyst where reactions take place on the surface of the nanofiber. In these catalyst embodiments, a high surface area reduces the size of the process equipment and/or reduces the amount of expensive material required in the catalyst.

The "specific surface area" is the surface area per mass or volume one of a fiber (or an average of a plurality of fibers). In various instances, the specific surface area is calculated based on a single nanofiber, or based on a collection of nanofibers and reported as a single average value. Techniques for measuring mass are known to those skilled in the art. In some instances, the surface area is calculated by measuring the diameter and length of nanofiber in the sample and applying the equation for the surface area of a cylinder (i.e., 2 times pi times half of the diameter of the nanofiber times the sum of the length of the nanofiber and half of the diameter of the nanofiber). In some instances, the surface area is measured by physical or chemical methods, for example by the Brunauer-Emmett, and Teller (BET) method where the difference between physisorption and desorption of inert gas is utilized. In some embodiments, the surface area is measured by titrating certain chemical groups on the nanofiber to estimate the number of groups on the surface, which is related to the surface area by a previously determined titration curve. Those skilled in the art of chemistry will be familiar with methods of titration.

The nanofiber has any suitable specific surface area. In some embodiments, the specific surface area is about 0.1 $m^2/g$, about 0.5 $m^2/g$, about 1.0 $m^2/g$, about 5 $m^2/g$, about 10 $m^2/g$, about 40 $m^2/g$, about 60 $m^2/g$, about 80 $m^2/g$, about 100 $m^2/g$, about 200 $m^2/g$, about 400 $m^2/g$, about 600 $m^2/g$, about 800 $m^2/g$, about 1,000 $m^2/g$, about 1,500 $m^2/g$, about 2,000 $m^2/g$, and the like. In some embodiments, the specific surface area is at least 0.1 $m^2/g$, at least 0.5 $m^2/g$, at least 1.0 $m^2/g$, at least 5 $m^2/g$, at least 10 $m^2/g$, at least 40 $m^2/g$, at least 60 $m^2/g$, at least 80 $m^2/g$, at least 100 $m^2/g$, at least 200 $m^2/g$, at least 400 $m^2/g$, at least 600 $m^2/g$, at least 800 $m^2/g$, at least 1,000 $m^2/g$, at least 1,500 $m^2/g$, at least 2,000 $m^2/g$, and the like. In some embodiments, the specific surface area is between about 0.1 $m^2/g$ and 1 $m^2/g$, between about 1 $m^2/g$ and 1,000 $m^2/g$, between about 10 $m^2/g$ and 100 $m^2/g$, between about 600 $m^2/g$ and 2,000 $m^2/g$, between about 10 $m^2/g$ and 1,000 $m^2/g$, between about 100 $m^2/g$ and 600 $m^2/g$, between about 300 $m^2/g$ and 500 $m^2/g$, and the like.

In some instances, methods disclosed herein (e.g., including using a high loading of uniformly distributed precursor) reduce the number and size of pores. Porosity is also called "void fraction" and is a measure of the void spaces in a material. In some embodiments, porosity is a fraction of the volume of voids over the total volume and is reported as a percentage between 0% and 100%. In various embodiments, the porosity depends on many factors including loading and distribution of precursor in the fluid stock, calcination conditions, and the like.

Methods for measuring or estimating porosity include microscopy. Methods also include first measuring the surface area of a sample of nanofibers by any direct or indirect method, then comparing the measured surface area with the surface area of an idealized cylinder having the average length and diameter of the nanofibers in the sample. In some embodiments, the difference between the measured and expected surface area is converted to a volume, then to a volume fraction by assuming that the pores are in the shape of spheres or cylinders having an average diameter. In some embodiments, the porosity is measured by immersing the nanofibers in a fluid that penetrates the pores. In such an embodiment, the porosity is estimated by comparing the total volume of nanofiber plus fluid with the volume that would be obtained from immersing a collection of idealized non-porous cylinders having the diameter and length of the nanofibers. The void volume is the difference between these volumes, which is converted to porosity by dividing the void volume by the volume of the idealized cylinders.

The nanofibers have any suitable porosity. In some embodiments, the porosity is about 1%, about 2%, about 4%, about 6%, about 8%, about 10%, about 15%, about 20%, about 25%, about 30%, about 40%, about 50%, about 60%, about 70% and the like. In some embodiments, the porosity is at most 1%, at most 2%, at most 4%, at most 6%, at most 8%, at most 10%, at most 15%, at most 20%, at most 25%, at most 30%, at most 40%, at most 50%, at most 60%, at most 70% and the like. In some embodiments, the porosity is at least 1%, at least 2%, at least 4%, at least 6%, at least 8%, at least 10%, at least 15%, at least 20%, at least 25%, at least 30%, at least 40%, at least 50%, at least 60%, at least 70% and the like. In some embodiments, the porosity is between about 1% and 10%, between about 10% and 50%, between about 20% and 30%, between about 30% and 70%, between about 1% and 50%, between about 5% and 20%, and the like.

In certain embodiments, nanofibers provided herein have improved performance over other nano-materials. In some instances, Young's modulus, fracture toughness, ultimate strength, electrical conductivity, thermal conductivity, flexibility, and/or other characteristics of the nanofibers described herein (and/or their composite materials) are improved over other nanostructures of the same material and/or over the bulk/sheet form of the same material. Table 1 illustrates the physical properties of certain nanofibers provided herein and the physical properties of bulk materials having similar structure. In some embodiments, provided herein are ceramic or metal oxide nanofibers (or nanofibers having a continuous matrix of ceramic and/or metal oxide) having an average Young's Modulus at least the level (or at least 90% the level) of a ceramic set forth in Table 1 (particularly rows 1 or 2 for amorphous ceramics, row 3 from crystalline ceramics, or row 4 or 5 for metal oxides). In some embodiments, provided herein are ceramic or metal oxide nanofibers (or nanofibers having a continuous matrix of ceramic and/or metal oxide) having an average Fracture Toughness at least the level (or at least 90% the level) as set forth in Table 1 (particularly rows 1 or 2 for amorphous ceramics, row 3 from crystalline ceramics, or row 4 or 5 for metal oxides). In certain embodiments, provided herein are ceramic or metal oxide nanofibers (or nanofibers having a continuous matrix of ceramic and/or metal oxide) having an average Ultimate Strength at least the level (or at least 90% the level) as set forth in Table 1 (particularly rows 1 or 2 for amorphous ceramics, row 3 from crystalline ceramics, or row 4 or 5 for metal oxides). In some embodiments, provided herein are metal nanofibers (or nanofibers having a continuous matrix of metal) having an average Young's Modulus at least the level (or at least 900 the level) of a ceramic set forth in Table 1 (particularly rows 6, 7, or 8). In some embodiments, provided herein are metal nanofibers (or nanofibers having a continuous matrix of metal) having an average Fracture Toughness at least the level (or at least 900% the level) as set forth in Table 1 (particularly rows 6, 7, or 8). In certain embodiments, provided herein are metal nanofibers (or nanofibers having a continuous matrix of metal) having an average Ultimate Strength at least the level (or at least 900% the level) as set forth in Table 1 (particularly rows 6, 7, or 8). In some embodiments, provided herein are metal nanofibers (or nanofibers having a continuous matrix of metal) having an average electrical conductivity of at least the level (or at least 900% the level) as set forth in Table 1 (particularly rows 6, 7, or 8).

TABLE 1

| Material | Youngs Modulus (GPa) | | Fracture Toughness (MPa · m$^{1/2}$) | Ultimate Strength (MPa) | | Electrical Conductivity (log(S/m)) | |
|---|---|---|---|---|---|---|---|
| | nanofiber | bulk | | nanofiber | bulk | nanofiber | bulk |
| SiO$_2$ (amorphous) | 79 | 80 | 0.71 | 41 | 33 | — | — |
| Al$_2$O$_3$ (amorphous) | 81 | | 0.99 | 77 | | — | |
| ZrO$_2$ (crystalline) | 818 | 210 | 2.15 | 2612 | 1900 | — | — |
| ZnO | 137 | | 1.4 | 109 | | 2.9 | |
| Fe$_2$O$_3$ | 118 | | 1.32 | 144 | | 3.3 | |
| Cu | 608 | 117 | 4.12 | 191 | 70 | 6.6 | 7.4 |
| Ni | 407 | | 2.81 | 123 | | 5.1 | |
| Fe | 299 | | 1.47 | 218 | | 4.6 | |
| ZrO$_2$/Ni nanocrystals (~5:1) | 718 | | 1.88 | 1011 | | — | |

In some embodiments, nanofibers described herein have improved Young's modulus over similar materials in other nanostructure or bulk forms. In some instances, provided herein are nanofibers having a mean or median nanofiber Young's modulus-to-diameter ratio of at least 0.1 GPa/nm. In certain instances, provided herein are nanofibers having a mean or median nanofiber Young's modulus-to-diameter ratio of at least 0.13 GPa/nm. In specific instances, provided herein are nanofibers having a mean or median nanofiber Young's modulus-to-diameter ratio of at least 0.15 GPa/nm. In more specific instances, provided herein are nanofibers having a mean or median nanofiber Young's modulus-to-diameter ratio of at least 0.18 GPa/nm. In still more specific instances, provided herein are nanofibers having a mean or median nanofiber Young's modulus-to-diameter ratio of at least 0.2 GPa/nm. In yet more specific instances, provided herein are nanofibers having a mean or median nanofiber Young's modulus-to-diameter ratio of at least 0.25 GPa/nm. In specific instances, provided herein are nanofibers having a mean or median nanofiber Young's modulus-to-diameter ratio of at least 0.3 GPa/nm. In some instances, provided herein are nanofibers having a mean or median nanofiber Young's modulus-to-diameter ratio of at least 0.05 GPa/nm or at least 0.5 GPa/nm.

In some embodiments, provided herein are amorphous ceramic nanofibers (e.g., pure amorphous ceramic nanofibers, as described herein, or nanofibers comprising an amorphous ceramic continuous matrix) comprising an average Young's modulus-to-diameter ratio of at least 0.15 GPa/nm. In specific embodiments, provided herein are amorphous ceramic nanofibers comprising an average Young's modulus-to-diameter ratio of at least 0.2 GPa/nm. In still more specific embodiments, provided herein are amorphous ceramic nanofibers comprising an average Young's modulus-to-diameter ratio of at least 0.3 GPa/nm. In yet more specific embodiments, provided herein are amorphous ceramic nanofibers comprising an average Young's modulus-to-diameter ratio of at least 0.35 GPa/nm. In some embodiments, provided herein are amorphous ceramic nanofibers comprising an average ultimate strength-to-diameter ratio of at least 0.05 MPa/nm. In specific embodiments, provided herein are amorphous ceramic nanofibers comprising an average ultimate strength-to-diameter ratio of at least 0.075 MPa/nm. In yet more specific embodiments, provided herein are amorphous ceramic nanofibers comprising an average ultimate strength-to-diameter ratio of at least 0.1 MPa/nm. In still more specific embodiments, provided herein are amorphous ceramic nanofibers comprising an average ultimate strength-to-diameter ratio of at least 0.15 MPa/nm. In yet more specific embodiments, provided herein are amorphous ceramic nanofibers comprising an average ultimate strength-to-diameter ratio of at least 0.2 MPa/nm. In some embodiments, provided herein are amorphous ceramic nanofibers comprising an average ultimate strength-to-diameter ratio of at least 0.075 MPa/nm and an average Young's modulus-to-diameter ratio of at least 0.15 GPa/nm. In more specific embodiments, provided herein are amorphous ceramic nanofibers comprising an average ultimate strength-to-diameter ratio of at least 0.15 MPa/nm and an average Young's modulus-to-diameter ratio of at least 0.3 GPa/nm. In some embodiments, provided herein are amorphous ceramic nanofibers having a fracture toughness of at least 0.5 MPa·m$^{1/2}$. In specific embodiments, provided herein are amorphous ceramic nanofibers having a fracture toughness of at least 0.6 MPa·m$^{1/2}$. In more specific embodiments, provided herein are amorphous ceramic nanofibers having a fracture toughness of at least 0.7 MPa·m$^{1/2}$.

In some embodiments, provided herein are crystalline ceramic nanofibers (e.g., pure crystalline ceramic nanofibers, as described herein, or nanofibers comprising a crystalline ceramic continuous matrix) comprising an average Young's modulus-to-diameter ratio of at least 1 GPa/nm. In specific embodiments, provided herein are crystalline ceramic nanofibers comprising an average Young's modulus-to-diameter ratio of at least 1.5 GPa/nm. In still more specific embodiments, provided herein are crystalline ceramic nanofibers comprising an average Young's modulus-to-diameter ratio of at least 2 GPa/nm. In yet more specific embodiments, provided herein are crystalline ceramic nanofibers comprising an average Young's modulus-to-diameter ratio of at least 3 GPa/nm. In more specific embodiments, provided herein are crystalline ceramic nanofibers comprising an average Young's modulus-to-diameter ratio of at least 4 GPa/nm. In some embodiments, provided herein are crystalline ceramic nanofibers comprising an average ultimate strength-to-diameter ratio of at least 3 MPa/nm. In specific embodiments, provided herein are crystalline ceramic nanofibers comprising an average ultimate strength-to-diameter ratio of at least 5 MPa/nm. In yet more specific embodiments, provided herein are crystalline ceramic nanofibers comprising an average ultimate strength-to-diameter ratio of at least 7.5 MPa/nm. In still more specific embodiments, provided herein are crystalline ceramic nanofibers comprising an average ultimate strength-to-diameter ratio of at least 10 MPa/nm. In yet more specific embodiments, provided herein are crystalline ceramic nanofibers comprising an average ultimate strength-to-diameter ratio of at least 12.5 MPa/nm. In some embodiments, provided herein are crystalline ceramic nanofibers comprising an average ultimate strength-to-diameter ratio of at least 5 MPa/nm and an average Young's modulus-to-diameter ratio of at least 1.5 GPa/nm. In more specific embodiments, provided herein are crystalline ceramic nanofibers comprising an average ultimate strength-to-diameter ratio of at least 12.5 MPa/nm and an average Young's modulus-to-diameter ratio of at least 4 GPa/nm. In some embodiments, provided herein are crystalline ceramic nanofibers having an average fracture toughness of at least 1.5 $MPa \cdot m^{1/2}$. In specific embodiments, provided herein are crystalline ceramic nanofibers having an average fracture toughness of at least 1.8 $MPa \cdot m^{1/2}$. In more specific embodiments, provided herein are crystalline ceramic nanofibers having an average fracture toughness of at least 2.1 $MPa \cdot m^{1/2}$.

In some embodiments, provided herein are metal nanofibers (e.g., pure metal nanofibers, as described herein, or nanofibers comprising a metal continuous matrix) comprising an average Young's modulus-to-diameter ratio of at least 0.8 GPa/nm. In specific embodiments, provided herein are metal nanofibers comprising an average Young's modulus-to-diameter ratio of at least 1.1 GPa/nm. In still more specific embodiments, provided herein are metal nanofibers comprising an average Young's modulus-to-diameter ratio of at least 1.5 GPa/nm. In yet more specific embodiments, provided herein are metal nanofibers comprising an average Young's modulus-to-diameter ratio of at least 2 GPa/nm. In more specific embodiments, provided herein are metal nanofibers comprising an average Young's modulus-to-diameter ratio of at least 2.9 GPa/nm. In some embodiments, provided herein are metal nanofibers comprising an average ultimate strength-to-diameter ratio of at least 0.2 MPa/nm. In specific embodiments, provided herein are metal nanofibers comprising an average ultimate strength-to-diameter ratio of at least 0.35 MPa/nm. In yet more specific embodiments, provided herein are metal nanofibers comprising an average ultimate strength-to-diameter ratio of at least 0.5 MPa/nm. In still more specific embodiments, provided herein are metal nanofibers comprising an average ultimate strength-to-diameter ratio of at least 0.7 MPa/nm. In yet more specific embodiments, provided herein are metal nanofibers comprising an average ultimate strength-to-diameter ratio of at least 0.9 MPa/nm. In some embodiments, provided herein are metal nanofibers comprising an average ultimate strength-to-diameter ratio of at least 0.35 MPa/nm and an average Young's modulus-to-diameter ratio of at least 1.1 GPa/nm. In more specific embodiments, provided herein are metal nanofibers comprising an average ultimate strength-to-diameter ratio of at least 0.9 MPa/nm and an average Young's modulus-to-diameter ratio of at least 2.9 GPa/nm. In some embodiments, provided herein are metal nanofibers having an average fracture toughness of at least 3 $MPa \cdot m^{1/2}$. In specific embodiments, provided herein are metal nanofibers having an average fracture toughness of at least 3.5 $MPa \cdot m^{1/2}$. In more specific embodiments, provided herein are metal nanofibers having a average fracture toughness of at least 4.1 $MPa \cdot m^{1/2}$. In some embodiments, the average electrical conductivity of a metal nanofiber provided herein has a log(S/m) to log(S/m) ratio with an identical bulk material of at least 0.75 (i.e., log of the electrical conductivity along the length of the metal nanofiber divided by log of the electrical conductivity of the same metal, in bulk). In specific embodiments, the average electrical conductivity of a metal nanofiber provided herein has a log(S/m) to log(S/m) ratio with an identical bulk material of at least 0.85. In more specific embodiments, the average electrical conductivity of a metal nanofiber provided herein has a log(S/m) to log(S/m) ratio with an identical bulk material of at least 0.9. In still more specific embodiments, the average electrical conductivity of a metal nanofiber provided herein has a log(S/m) to log(S/m) ratio with an identical bulk material of at least 0.95.

In some embodiments, applications of the nanofibers described herein benefit from nanofibers having a high conductivity. In some instances, a high electrical conductivity is desirable in energy generation applications that involve moving electrons through the nanofiber (e.g., as an electrode of a battery). In some embodiments, nanofibers that are long and continuous with a reduced number or size of defects have a higher conductivity.

In various embodiments, conductivity means either "thermally conductivity", "electrically conductivity", or both thermally and electrically conductivity unless context clearly dictates otherwise. Electrical conductivity is a measure of a material's ability to conduct electric current. Electrical conductivity is measured in units of Siemens per length (e.g., S/cm). The reciprocal of conductivity is resistivity. Electrical resistivity is a measure of how strongly a material opposes the flow of electric current and is reported in units of ohm meter ($\Omega$). In some instances, thermal conductivity is reported in units of watts per meter Kelvin (W/m/K). Thermal resistivity is the reciprocal thereof. Inspection of the units indicates whether the value is electrical or thermal conductivity.

In one aspect, the nanofiber has a conductivity (e.g., electrical or thermal) which is compared to a thin sheet of the material from which the nanofiber is made. For example, a copper nanofiber is compared with a thin sheet of copper. The nanofibers have any suitable conductivity as a percentage of the conductivity of the material is formed into a sheet. In some embodiments, the conductivity is variable over different portions of a collection of nanofibers, or along different directions. In various embodiments, conductivity is reported as either an average value, or a value specific to a certain condition or direction of measurement (i.e., for anisotropic materials).

In some embodiments, the nanofiber has a conductivity of about 5%, about 10%, about 20%, about 30%, about 40%, about 50%, about 60%, about 70%, about 80%, about 90%, about 95%, or about 100% when compared with the conductivity of the material when formed into a sheet. In some embodiments, the nanofiber has a conductivity of at least about 5%, at least about 10%, at least about 20%, at least about 30%, at least about 40%, at least about 50%, at least about 60%, at least about 70%, at least about 80%, at least about 90%, at least about 95%, or at least about 100% when compared with the conductivity of the material when formed into a sheet. In some embodiments, the nanofiber has a conductivity of at most about 5%, at most about 10%, at most about 20%, at most about 30%, at most about 40%, at most about 50%, at most about 60%, at most about 70%, at most about 80%, at most about 90%, at most about 95%, or at most about 100% when compared with the conductivity of the material when formed into a sheet. In some embodiments, the nanofiber has a conductivity of between about 5% and 10%, between about 10% and 20%, between about 20% and 30%, between about 30% and 40%, between about 40% and 50%, between about 50% and 60%, between about 60% and 70%, between about 70% and 80%, between about 80% and 90%, between about 90% and 95%, between about 95% and 100%, when compared with the conductivity of the material when formed into a sheet.

In some instances, conductivity is reported without reference to the conductivity of the material when formed into a sheet. For example in some embodiments, electrical conductivity is reported on an absolute, rather than relative basis. Electrical conductivity is measured by any suitable method known to those skilled in the art. For example in some embodiments, conductivity is measured by first measuring the resistance and calculating the reciprocal. In one instance, one hooks up a sample of nanofibers to be tested to a voltage source and measures the current going through the sample and the voltage across the sample. In some instances, the resistance is calculated from Ohm's law (i.e., R=E/I where R is resistance in ohms, E is voltage in volts and I is current in amperes). Once one has resistance, one can calculate resistivity. Resistivity is a factor, which when multiplied by the length of the sample and divided by its cross-sectional area, yields the resistance. Conductivity is the reciprocal of the resistivity.

The nanofibers have any suitable electrical conductivity. In various embodiments, electrical conductivity is measured as an average value, at a specific condition, or along a specific direction of the nanofiber sample. In some embodiments, the conductivity is about 1 S/cm, about 10 S/cm, about 100 S/cm, about $10^3$ S/cm, about $10^4$ S/cm, about $10^5$ S/cm, about $10^6$ S/cm, about $10^7$ S/cm, about $10^8$ S/cm, and the like. In some embodiments, the conductivity is at least 1 S/cm, at least 10 S/cm, at least 100 S/cm, at least $10^3$ S/cm, at least $10^4$ S/cm, at least $10^5$ S/cm, at least $10^6$ S/cm, at least $10^7$ S/cm, at least $10^8$ S/cm, and the like. In some embodiments, the conductivity is at most 1 S/cm, at most 10 S/cm, at most 100 S/cm, at most $10^3$ S/cm, at most $10^4$ S/cm, at most $10^5$ S/cm, at most $10^6$ S/cm, at most $10^7$ S/cm, at most $10^8$ S/cm, and the like. In some embodiments, the conductivity is between about 1 S/cm and 10 S/cm, between about 10 S/cm and 100 S/cm, between about 100 S/cm and 1,000 S/cm, between about 1,000 S/cm and $10^4$ S/cm, between about $10^4$ S/cm and $10^5$ S/cm, between about $10^5$ S/cm and $10^6$ S/cm, between about $10^6$ S/cm and $10^7$ S/cm, between about $10^7$ S/cm and $10^8$ S/cm, between about $10^5$ S/cm and $10^8$ S/cm, and the like.

In some embodiments, the nanofibers or collections of nanofibers of the present disclosure are flexible. In some instances, flexible nanofibers are advantageous in applications such as in the manufacture of flexible solar panels. In some instances, flexibility is quantified by the Young's modulus, which is the slope of the initial linear portion of a stress-strain curve. The Young's modulus has units of pressure, such as mega Pascals (MPa). In some embodiments, flexibility is different along different directions of the material, so may be reported with respect to a certain direction, or is reported as an average value.

In one aspect, the flexibility is at least partially determined by the calcination temperature. In one example, when the calcination temperature is about 200° C. the Young's modulus is at least 100 MPa. In some instances, lower calcination temperatures lead to a significantly higher fraction of amorphous metal or ceramic in the nanofiber, which results in higher flexibility.

The nanofibers have any suitable flexibility. In some embodiments, the nanofiber has a Young's modulus of about 10 MPa, about 20 MPa, about 40 MPa, about 60 MPa, about 80 MPa, about 100 MPa, about 150 MPa, about 200 MPa, about 250 MPa, about 300 MPa, about 400 MPa, about 1,000 MPa, and the like. In some embodiments, the nanofiber has a Young's modulus of at least about 10 MPa, at least about 20 MPa, at least about 40 MPa, at least about 60 MPa, at least about 80 MPa, at least about 100 MPa, at least about 150 MPa, at least about 200 MPa, at least about 250 MPa, at least about 300 MPa, at least about 400 MPa, at least about 1,000 MPa, and the like.

Nanofiber Mats

In some embodiments, the nanofibers described herein are collected or formed into any suitable structure (e.g., suitable for the desired application). Structures include, but are not limited to spheres, cones, cylinders, slabs, helixes, polygons, and the like. For simplicity of terminology, all possible shapes or assemblage of nanofibers are herein referred to as a "mat". In various embodiments, nanofiber mats comprise nanofibers of a single type, or nanofibers of at least two types.

In some embodiments, coherent nanofibers lead to a mat having desirable properties (e.g., a less brittle nanofiber mat). In some instances, these desirable properties emerge from the properties of the component nanofibers and/or depend on the method in which the nanofibers are formed into the mat. In some embodiments, the present disclosure includes the nanofiber mats. In one aspect, described herein are nanofiber mats formed by the nanofibers of the present disclosure. Also described herein are nanofiber mats prepared by any of the methods, or preparable by any of the methods in the present disclosure. In one aspect, described herein are methods for preparing nanofiber mats, optionally using an electrospinning process.

In some embodiments, nanofibers are collected in a given geometry as they are produced (e.g., by moving the collection plate relative to the spinnerets, i.e., 3-D printing). In various embodiments, nanofibers are formed into a given geometry after collection (optionally before calcination), or formed into a given geometry after calcination. In some instances, the nanofiber mat comprises nanofibers arranged in a controlled manner (e.g., on a mesh with a perpendicular lattice). In some embodiments, the nanofibers are arranged randomly. In various embodiments, the mats are patterned in any level of detail including different fibers of different types, laid in different directions, in contact with various other nanofibers or insulated from various other nanofibers, and the like. In some embodiments, the nanofibers are cross-linked and/or surface modified.

In some nanofiber mats, the nanofiber surface proves a high surface area for mass transfer of a chemical product. These nanofibers are particularly applicable as catalysts for example. In some embodiments, the nanofiber surface proves a high surface area for mass transfer of a protons or electrons in the nanofiber mat. These nanofibers are particularly applicable as electrodes for example.

Figure 39:
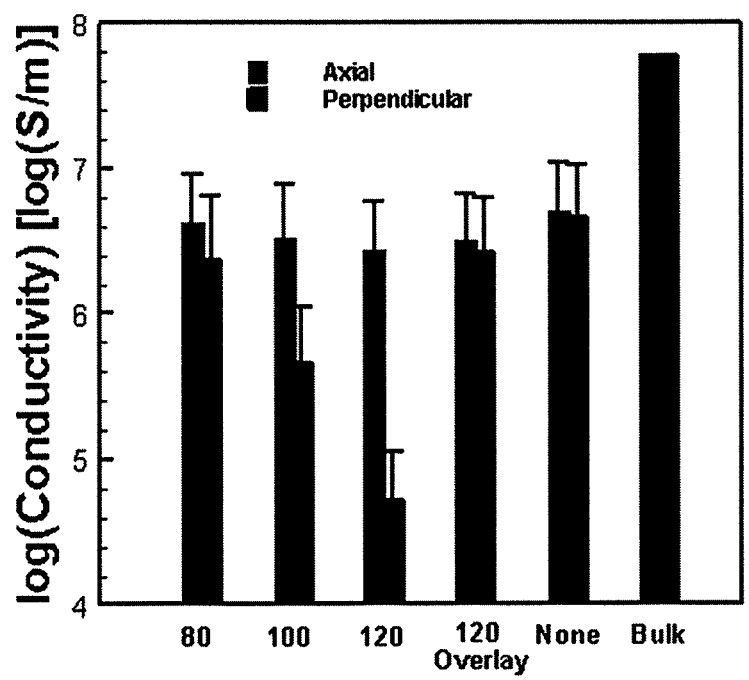
FIG. 39 illustrates a graphic comparing the effect of fiber alignment conditions on electrical conductivity in the axial and perpendicular direction of a Ni nanofiber mat.

In some instances, nanofibers provided herein are assembled into a nanofiber mat. In some instances, use of nanofiber mats provide for the improvement of certain nanofiber performance characteristics. For example, FIG. 39 shows a graphic comparing the effect of fiber alignment conditions on electrical conductivity in the axial and perpendicular direction of a Ni nanofiber mat.

Properties of Nanofiber Mats

In some instances, the nanofiber mat has substantially the same properties as the nanofibers from which it is comprised. For example, a similar porosity, similar specific surface area, similar specific conductivity, and the like. In some instances, the nanofiber mat has different properties from the nanofibers from which it is comprised. For example, a different porosity, different specific surface area, different conductivity, and the like. In various embodiments, the property of the mat is either greater than or less than the property of an individual nanofiber.

In some embodiments, the nanofiber mat is "isotropic" or has isotropic properties (e.g., meaning that the nanofiber mat has the same or substantially similar properties in all orientations and along all directions of the material). In some embodiments, the mat is "anisotropic" (e.g., meaning that it has different properties in various orientations or along different directions of the material). In some embodiments, anisotropic properties are created by controlling the orientation of the nanofibers in the mat. For example, in one embodiment where nanofiber direction was uniformly controlled, there was an approximately 100 fold difference in electric conductivity of copper nanofibers between the axial direction (direction of the nanofiber) and the perpendicular direction.

In embodiments where the mat is anisotropic, a given property differs in a second orientation or direction compared to a first orientation or direction by about 5%, about 10%, about 15%, about 20%, about 30%, about 40%, about 50%, about 60%, about 80%, about 100%, about 150%, about 200%, about 300%, about 400%, about 500%, and the like. In some embodiments, a given property is about 10 times, about 20 times, about 50 times, about 100 times, about 200 times, about 500 times, about 1,000 times, about 10,000 times, and the like higher in a second direction or orientation than in a first direction or orientation.

In some embodiments, a given property differs in a second orientation or direction compared to a first orientation or direction by at least about 5%, at least about 10%, at least about 15%, at least about 20%, at least about 30%, at least about 40%, at least about 50%, at least about 60%, at least about 80%, at least about 100%, at least about 150%, at least about 200%, at least about 300%, at least about 400%, at least about 500%, and the like. In some embodiments, a given property is at least about 10 times, at least about 20 times, at least about 50 times, at least about 100 times, at least about 200 times, at least about 500 times, at least about 1,000 times, at least about 10,000 times, and the like higher in a second direction or orientation than in a first direction or orientation.

In some embodiments, a given property differs in a second orientation or direction compared to a first orientation or direction by at most about 5%, at most about 10%, at most about 15%, at most about 20%, at most about 30%, at most about 40%, at most about 50%, at most about 60%, at most about 80%, at most about 100%, at most about 150%, at most about 200%, at most about 300%, at most about 400%, at most about 500%, and the like. In some embodiments, a given property is at most about 10 times, at most about 20 times, at most about 50 times, at most about 100 times, at most about 200 times, at most about 500 times, at most about 1,000 times, at most about 10,000 times, and the like higher in a second direction or orientation than in a first direction or orientation.

In some embodiments, the mat has a conductivity in a first direction and a conductivity in a second direction, wherein the conductivity in the first direction is at least one hundred times higher than in the second direction. In some embodiments, the mat has a conductivity of at least 1.0 S/cm in either the first or second direction.

In some instances, the porosity of the nanofiber mat is a consideration, for example in filtration applications. For example, in order to remove particles of a certain diameter, it is desirable to have a mat with pores smaller than the diameter of the smallest particle to be removed in some instances.

In some embodiments, the porosity of the nanofiber mat is greater than the porosity of the nanofibers that comprise the mat. In some embodiments, the porosity of the mat is the combination of the spaces between the nanofiber strands and the pores within the nanofibers themselves. In some instances, microscopy is used to estimate porosity. In some instances, the porosity of a nanofiber mat having a first volume defined by its external surface is measured by submersing the nanofiber mat in a fluid having a second volume. The volume of the fluid plus submersed nanofiber mat defines a third volume. A fourth volume is obtained by subtracting the second volume from the third volume. The porosity is one minus the ratio of the fourth volume to the first volume. In some embodiments, porosity is expressed as a percentage.

The nanofiber mat has any suitable porosity. In some embodiments, the porosity is about 1%, about 2%, about 4%, about 6%, about 8%, about 10%, about 15%, about 20%, about 25%, about 30%, about 40%, about 50%, about 60%, about 70% and the like. In some embodiments, the porosity is at most 1%, at most 2%, at most 4%, at most 6%, at most 8%, at most 10%, at most 15%, at most 20%, at most 25%, at most 30%, at most 40%, at most 50%, at most 60%, at most 70% and the like. In some embodiments, the porosity is at least 1%, at least 2%, at least 4%, at least 6%, at least 8%, at least 10%, at least 15%, at least 20%, at least 25%, at least 30%, at least 40%, at least 50%, at least 60%, at least 70% and the like. In some embodiments, the porosity is between about 1% and 10%, between about 10% and 50%, between about 20% and 30%, between about 30% and 70%, between about 1% and 50%, between about 5% and 20%, and the like.

In some instances, porosity has units of length. The porous length is the distance between a point on a nanofiber strand and the nearest point on another nanofiber strand. In some instances, objects having a dimension longer than this porous length will not generally be able to pass through the mat. In some instances, the porous length is measured by bombarding the nanofiber mat with particles of a plurality of diameters until the particles of a certain size pass through the nanofiber mat, indicating that the nanofiber mat has a porous length approximately equal to the diameter of said particles.

The pores of the nanofiber mat have any suitable size. In some embodiments, the pores are about 0.1 microns, about 0.2 microns, about 0.5 microns, about 0.7 microns, about 1 microns, about 2 microns, about 4 microns, about 6 microns, about 8 microns, about 10 microns, about 15 microns, about 20 microns, about 30 microns, about 40 microns, about 50 microns, about 70 microns, about 100 microns, about 200 microns, and the like on their longest dimension. In some embodiments, the pores are at most about 0.1 microns, at most about 0.2 microns, at most about 0.5 microns, at most about 0.7 microns, at most about 1 microns, at most about 2 microns, at most about 4 microns, at most about 6 microns, at most about 8 microns, at most about 10 microns, at most about 15 microns, at most about 20 microns, at most about 30 microns, at most about 40 microns, at most about 50 microns, at most about 70 microns, at most about 100 microns, at most about 200 microns, and the like on their longest dimension. In other embodiments, the pores are at least about 0.1 microns, at least about 0.2 microns, at least about 0.5 microns, at least about 0.7 microns, at least about 1 microns, at least about 2 microns, at least about 4 microns, at least about 6 microns, at least about 8 microns, at least about 10 microns, at least about 15 microns, at least about 20 microns, at least about 30 microns, at least about 40 microns, at least about 50 microns, at least about 70 microns, at least about 100 microns, at least about 200 microns, and the like on their longest dimension. In some embodiments, the pores are between about 0.5 microns and 50 microns, between about 1 microns and 10 microns, between about 10 microns and 50 microns, between about 0.1 microns and 5 microns, between about 2 microns and 10 microns, between about 40 microns and 100 microns, and the like on their longest dimension.

In some instances, the density of the nanofiber mat is another characteristic to consider in certain applications. In some instances, the concentration of the polymer in the fluid stock has an impact on the density of the mat (e.g., potentially with decreased amounts of polymer leading to a denser mat, e.g., because fewer voids are left when the polymer is removed in calcination). In one example, the density of the mat was at least about 1 g/m$^3$ where the polymer was less than about 30% in the fluid stock.

The nanofiber mat has any suitable density. In some embodiments, the mat has a density of about 0.01 g/cm$^3$, about 0.05 g/cm$^3$, about 0.1 g/cm$^3$, about 0.2 g/cm$^3$, about 0.4 g/cm$^3$, about 0.8 g/cm$^3$, about 1 g/cm$^3$, about 5 g/cm$^3$, about 10 g/cm$^3$, and the like. In some embodiments, the mat has a density of at least about 0.01 g/cm$^3$, at least about 0.05 g/cm$^3$, at least about 0.1 g/cm$^3$, at least about 0.2 g/cm$^3$, at least about 0.4 g/cm$^3$, at least about 0.8 g/cm$^3$, at least about 1 g/cm$^3$, at least about 5 g/cm$^3$, at least about 10 g/cm$^3$, and the like. In some embodiments, the mat has a density of at most about 0.01 g/cm$^3$, at most about 0.05 g/cm$^3$, at most about 0.1 g/cm$^3$, at most about 0.2 g/cm$^3$, at most about 0.4 g/cm$^3$, at most about 0.8 g/cm$^3$, at most about 1 g/cm$^3$, at most about 5 g/cm$^3$, at most about 10 g/cm$^3$, and the like. In some embodiments, the mat has a density of between about 0.01 g/cm$^3$ and 0.05 g/cm$^3$, between about 0.05 g/cm$^3$ and 0.3 g/cm$^3$, between about 0.1 g/cm$^3$ and 1 g/cm$^3$, between about 1 g/cm$^3$ and 5 g/cm$^3$, and the like.

The mat has any suitable number of strands per area or volume. In some instances, microscopy is used to determine the number of strands per area or volume. In some embodiments, the mat comprises about 5 strands, about 10 strands, about 50 strands, about 100 strands, about 150 strands, about 250 strands, about 500 strands, about 1,000 strands, about 5,000 strands, about 50,000 strands, and the like per square millimeter or per cubic millimeter. In some embodiments, the mat comprises at least about 5 strands, at least about 10 strands, at least about 50 strands, about 100 strands, at least about 150 strands, at least about 250 strands, at least about 500 strands, at least about 1,000 strands, at least about 5,000 strands, at least about 50,000 strands, and the like per square millimeter or per cubic millimeter. In some embodiments, the mat comprises between about 5 strands to 50 strands, between about 50 strands to 500 strands, between about 500 strands to 5,000 strands, between about 5,000 strands to 50,000 strands, and the like per square millimeter or per cubic millimeter.

Figure 38:
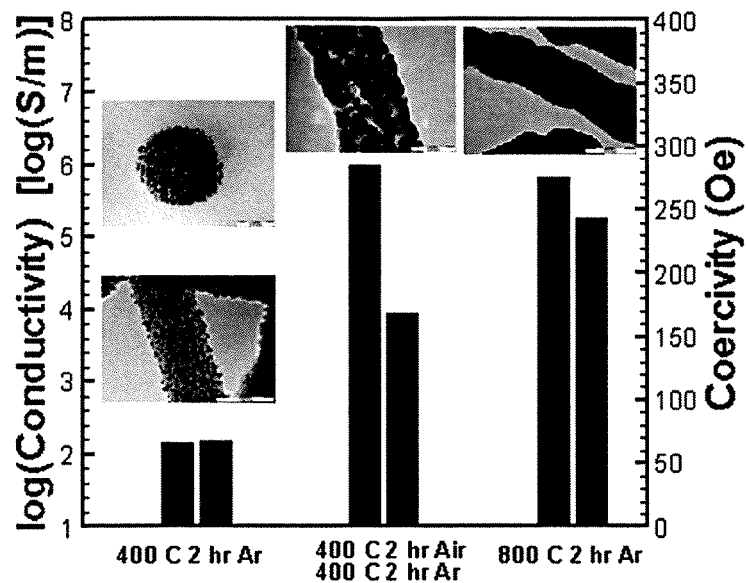
FIG. 38 illustrates a graphic comparing the effect of calcination conditions on electrical conductivity and magnetic coercivity of Ni nanofibers.

In some instances, the sizes of the crystal domains in the nanofiber have an effect on properties of the nanofiber or nanofiber mat (e.g., including magnetic strength and electrical conductivity). In some instances, calcination conditions have an effect on crystallization domains. In some embodiments, one may control the properties of the nanofiber or nanofiber mat by controlling the calcination conditions. In one example, FIG. 38 shows that by tuning calcination conditions with Ni nanofibers, a 5-fold difference in magnetic strength was obtained and a 10,000 fold difference in electric conductivity was obtained. Described herein are nanofibers or nanofiber mats having crystal domains of a certain size. The present disclosure also encompasses nanofibers or nanofiber mats with tunable properties and methods for tuning the properties of nanofiber or nanofiber mats (e.g., including magnetic or conductivity properties).

In some embodiments, there are a plurality of crystal domains in the nanofiber. In some embodiments, the domains are metal oxide domains. In various embodiments, these domains have various sizes, for example about 1 nm, about 5 nm, about 10 nm, about 15 nm, about 20 nm, about 25 nm, about 30 nm, about 40 nm, about 50 nm, about 70 nm, about 90 nm, and the like. In some embodiments, the domains are at least about 1 nm, at least about 5 nm, at least about 10 nm, at least about 15 nm, at least about 20 nm, at least about 25 nm, at least about 30 nm, at least about 40 nm, at least about 50 nm, at least about 70 nm, at least about 90 nm, and the like in size. In some embodiments, the domains are at most about 1 nm, at most about 5 nm, at most about 10 nm, at most about 15 nm, at most about 20 nm, at most about 25 nm, at most about 30 nm, at most about 40 nm, at most about 50 nm, at most about 70 nm, at most about 90 nm, and the like in size. In some embodiments, the domains have a size between about 1 nm and 100 nm, between about 20 nm and 30 nm, between about 1 nm and 20 nm, between about 30 nm and 90 nm, between about 40 nm and 70 nm, between about 15 nm and 40 nm, and the like.

In one aspect, the nanofiber and/or nanofiber mat is magnetic. The coercivity (also called the coercive field or coercive force) of a ferromagnetic material is the intensity of the applied magnetic field required to reduce the magnetization of that material to zero after the magnetization of the sample has been driven to saturation. Coercivity is usually measured in oersted (Oe) or ampere/meter units.

In some embodiments, the nanofiber mat has any suitable magnetic coercivity. In some embodiments, the nanofiber mat has a magnetic coercivity of about 10 Oe, about 20 Oe, about 40 Oe, about 60 Oe, about 80 Oe, about 100 Oe, about 125 Oe, about 150 Oe, about 175 Oe, about 200 Oe, about 250 Oe, about 300 Oe, about 350 Oe, about 400 Oe, about 500 Oe, about 1,000 Oe, and the like. In some embodiments, the nanofiber mat has a magnetic coercivity of at least about 10 Oe, at least about 20 Oe, at least about 40 Oe, at least about 60 Oe, at least about 80 Oe, at least about 100 Oe, at least about 125 Oe, at least about 150 Oe, at least about 175 Oe, at least about 200 Oe, at least about 250 Oe, at least about 300 Oe, at least about 350 Oe, at least about 400 Oe, at least about 500 Oe, at least about 1,000 Oe, and the like. In some embodiments, the nanofiber mat has a magnetic coercivity of at most about 10 Oe, at most about 20 Oe, at most about 40 Oe, at most about 60 Oe, at most about 80 Oe, at most about 100 Oe, at most about 125 Oe, at most about 150 Oe, at most about 175 Oe, at most about 200 Oe, at most about 250 Oe, at most about 300 Oe, at most about 350 Oe, at most about 400 Oe, at most about 500 Oe, at most about 1,000 Oe, and the like. In some embodiments, the nanofiber mat has a magnetic coercivity of between about 50 Oe and 200 Oe, between about 100 Oe and 300 Oe, between about 200 Oe and 500 Oe, between about 300 Oe and 1,000 Oe, between about 10 Oe and 100 Oe, between about 175 Oe and 300 Oe, between about 200 Oe and 250 Oe, and the like.

In one aspect, the nanofiber and/or nanofiber mat is paramagnetic or superparamagnetic. Paramagnetism is a form of magnetism that occurs in the presence of an externally applied magnetic field. Superparamagnetism is a form of magnetism which appears in small ferromagnetic or ferrimagnetic nanoparticles or nanofibers. In some instances (e.g., for sufficiently small nanoparticles or nanofibers), magnetization randomly flips direction under the influence of temperature. The time between two flips is called the Neel relaxation time. In the absence of external magnetic field, when the time used to measure the magnetization of the nanoparticles is much longer than the Neel relaxation time, their magnetization appears to be on average zero. That is, they are said to be in the superparamagnetic state. In this state, an external magnetic field is able to magnetize the nanoparticles or nanofibers, similarly to a paramagnet.

System

In some embodiments, a number of components of a system interact to produce nanofibers. Without limitation, these include an electrospinning apparatus and a module for collecting the electrospun fluid stock or nanofiber. These two components are related by a voltage difference such that the thin jet of fluid stock emanating from the electrospinner is attracted to and deposits on the collection module. In some embodiments, the electrospinning component of the system is a gas-assisted electrospinner. The gas used to accelerate the jet of fluid stock is optionally air.

In some embodiments, the system also includes a fluid stock. Among other things, the fluid stock interacts with the electrospinner to produce a nanofiber. In some embodiments, the fluid stock has an elongational viscosity that allows for a jet of fluid stock to erupt from a charged droplet. In some embodiments, the fluid stock is a system of polymer and precursor that interact with each other to at least in part determine the spinnability of the fluid stock and the properties of the nanofiber.

In some embodiments, the system also includes an apparatus for calcinating the nanofiber (e.g., a heater or a gas chamber). In some instances, the gas is part of the system, wherein the gas is optionally air, hydrogen, nitrogen, an inert gas, and the like.

Electrochemical Devices

Figure 40:
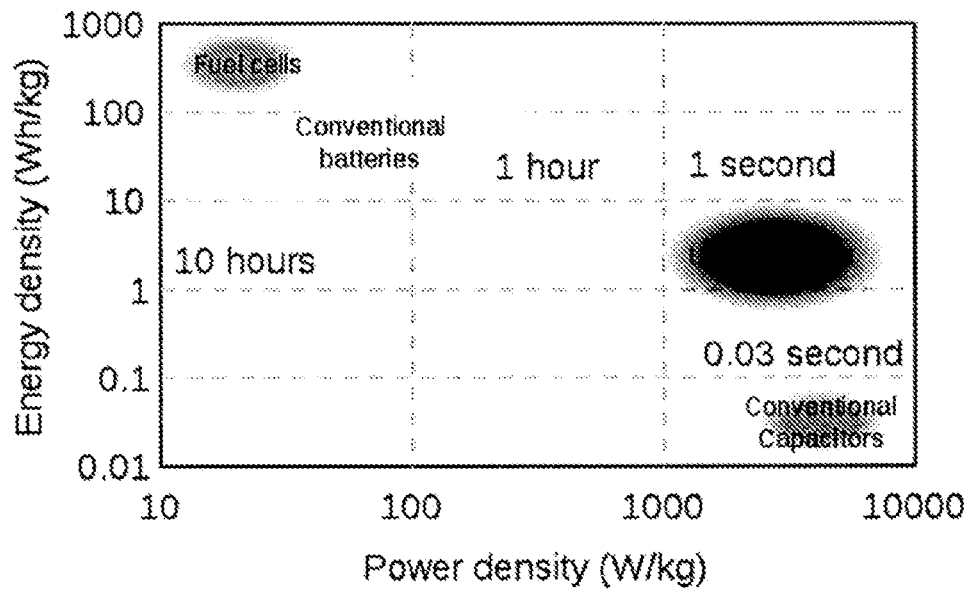
FIG. 40 illustrates a Ragone plot depicting energy densities and power densities typical of electrochemical devices.

Electrochemical devices include fuel cells, batteries, capacitors and ultra-capacitors, among others. In some instances, solar cells are electrochemical devices. In some instances, other electrochemical devices do not fit within the categories listed herein. In various embodiments, electrochemical devices have a wide range of energy densities and power densities that are summarized graphically on a Ragone chart (FIG. 40). Energy density is reported in units of watt-hours per kilogram (W·h/kg) or equivalents and is a measure of the amount of useful energy stored in a given size device (by mass or volume). Power density is reported in units of watts per kilogram (W/kg) or equivalents and is a measure of how quickly energy can be utilized. In some instances, fuel cells have a high energy density, but a low power density. In some instances, capacitors have a high power density but a low energy density. In some instances, batteries and ultracapacitors have energy densities and power densities between capacitors and fuel cells.

In one aspect, described herein are uses of nanofibers in electrochemical devices. For example, they are used as electrodes in fuel cells or batteries (e.g., where they may have beneficial properties such as a high conductivity and surface area). In some embodiments, they are utilized as the dielectric layer in an ultracapacitor. In various aspects, the present disclosure includes an electrochemical device that includes the nanofibers described herein, includes an electrochemical device that includes a nanofiber produced by the methods described herein, and includes an electrochemical device that includes a nanofiber produced by the system described herein. In some aspects, the disclosure also includes methods for making and methods for using electrochemical devices that comprise nanofibers.

In some embodiments, devices are built that comprise the nanofibers described herein. In some embodiments, such a device is created by substituting a component of the device with nanofibers (e.g., thus improving the function of the device), but substantially preserving the overall architecture and design of the device. In some embodiments, the architecture and overall design of the device comprising nanofibers is markedly different than a fuel cell, battery, ultracapacitor and the like.

In some instances, it is desirable to have or make an electrochemical device with both high energy density and high power density, for example to energize an electric vehicle that has both a long driving range (i.e., energy density) and can be charged and accelerate quickly (i.e., high power density). The electrochemical device has any suitable energy and power density. In some embodiments where the power density is at least about 100 W/kg, the energy density is at least about 10 W·h/kg, at least about 50 W·h/kg, at least about 100 W·h/kg, at least about 500 W·h/kg, at least about 1,000 W·h/kg, at least about 5,000 W·h/kg, and the like. In some embodiments where the power density is at least about 500 W/kg, the energy density is at least about 10 W·h/kg, at least about 50 W·h/kg, at least about 100 W·h/kg, at least about 500 W·h/kg, at least about 1,000 W·h/kg, at least about 5,000 W·h/kg, and the like. In some embodiments where the power density is at least about 1,000 W/kg, the energy density is at least about 10 W·h/kg, at least about 50 W·h/kg, at least about 100 W·h/kg, at least about 500 W·h/kg, at least about 1,000 W·h/kg, at least about 5,000 W·h/kg, and the like. In some embodiments where the power density is at least about 5,000 W/kg, the energy density is at least about 10 W·h/kg, at least about 50 W·h/kg, at least about 100 W·h/kg, at least about 500 W·h/kg, at least about 1,000 W·h/kg, at least about 5,000 W·h/kg, and the like. In some embodiments where the power density is at least about 10,000 W/kg, the energy density is at least about 10 W·h/kg, at least about 50 W·h/kg, at least about 100 W·h/kg, at least about 500 W·h/kg, at least about 1,000 W·h/kg, at least about 5,000 W·h/kg, and the like.

Fuel Cells

A fuel cell is an electrochemical cell that converts chemical energy into electrical energy. In some instances, electricity is generated from the reaction between a fuel supply and an oxidizing agent. In some embodiments, the reactants flow into the cell, and the reaction products flow out of it, while the electrolyte remains within it. In some embodiments, fuel cells are different from electrochemical cell batteries in that they consume a reactant from an external source (i.e., which is replenished).

In some embodiments, fuel cells are made up of three segments which are sandwiched together: the anode, the electrolyte, and the cathode. In some embodiments, two chemical reactions occur at the interfaces of the three different segments. In some embodiments, the net result of the two reactions is that fuel is consumed, water or carbon dioxide is created, and an electric current is created (e.g., which can be used to power electrical devices, normally referred to as the load). Many combinations of fuels and oxidants are possible. In some embodiments, a hydrogen fuel cell uses hydrogen as its fuel and oxygen (e.g., from air) as its oxidant. Other possible fuels include hydrocarbons and alcohols. Other possible oxidants include chlorine and chlorine dioxide.

In some embodiments, at the anode a catalyst oxidizes the fuel, (e.g., hydrogen), turning the fuel into a positively charged ion and a negatively charged electron. In some embodiments, the electrolyte is a substance specifically designed so ions can pass through it, but the electrons do not. In some instances, the freed electrons travel through a wire creating the electric current. In some instances, the ions travel through the electrolyte to the cathode. In some embodiments, once reaching the cathode, the ions are reunited with the electrons and the two react with a third chemical, (e.g., oxygen), to create water or carbon dioxide.

In some embodiments, a fuel cell has higher energy conversion efficiency than other power sources (e.g., since it converts chemical energy directly into electricity). In some embodiments, fuel cells produce no pollution (e.g., when hydrogen is used as the fuel) or less pollution (e.g., when hydrocarbon is used as the fuel) compared to combustion. In some embodiments, fuel cells operate quietly, reducing noise pollution. In some embodiments, a fuel cell operates continuously and generates electricity as long as the fuel is supplied. In some instances, fuel cells are used in applications including portable electronic devices, automobiles, and stationary power generation.

In some proton exchange membrane fuel cells, the catalyst for hydrogen oxidation at the anode is carbon supported platinum. Despite its popular use, the Pt/C anode system exhibits certain drawbacks in some instances. First, the use of carbon generally leads to the corrosion of the electrode in some embodiments. Secondly, the platinum is an expensive catalyst. In some instances, the fuel cells described herein comprise electrodes based on nanofibers (e.g., avoiding the corrosion by carbon and reduce the expensive Pt loading). In one embodiment, the nanofibers comprise intermetallic Fe—Pt.

In one aspect, described herein is the use of nanofibers in fuel cells. For example, they are used as electrodes, optionally anodes or cathodes. In various aspects, described herein is a fuel cell that comprises a nanofiber described herein, a fuel cell that comprises a nanofiber produced by the methods described herein, and includes a fuel cell that comprises a nanofiber produced by the system described herein. In one aspect, described herein are methods for making and methods for using fuel cells that comprise nanofibers.

In various embodiments, the nanofiber comprises any suitable material including, but not limited to iron (Fe), platinum (Pt), or any mixture thereof. In some embodiments, the nanofiber is a pure metal nanofiber or a metal alloy nanofiber, including any hybrid or hollow geometry. In some embodiments, the atoms have a certain arrangement (e.g., including a face-centered tetragonal structure). In various embodiments, the ratio of Fe to Pt atoms in the nanofiber of the fuel cell is about 1 Fe to 5 Pt, or about 4 Fe to 5 Pt for example. In some embodiments, the Fe and Pt atoms are substantially evenly distributed amongst each other (i.e., the nanofiber does not comprise aggregates of Pt or Fe). In some embodiments, the creation of the face-centered tetragonal structure of Fe—Pt is pursued to enhance oxygen reduction and durability under the minimized Pt loading. In some instances, the optional face-centered tetragonal structure also provides connectivity of the Pt.

In some instances, a Pt/C fuel cell mixes Pt particles with C and forms an electrode by vapor deposition of the mixture. In certain embodiments, the nanofibers and electrodes described herein significantly reduce the cost of the fuel cell (e.g., by using less platinum). In some embodiments, a gas-assisted electrospinning procedure is a cheaper and faster process than vapor deposition.

In some embodiments, the fuel cell comprises an anode and the anode comprises nanofibers. In some embodiments, a reduced amount of platinum is preferred (e.g., because of cost). The anode has any suitable amount of platinum (including no platinum). In some embodiments, the anode has by mass percentage about 5% Pt, about 10% Pt, about 15% Pt, about 20% Pt, about 25% Pt, about 30% Pt, about 40% Pt, about 50% Pt, about 70% Pt, and the like. In some embodiments, the anode has by mass percentage at most about 5% Pt, at most about 10% Pt, at most about 15% Pt, at most about 20% Pt, at most about 25% Pt, at most about 30% Pt, at most about 40% Pt, at most about 50% Pt, at most about 70% Pt, and the like. In some embodiments, the fuel cell has at least 10 fold less or at least 30 fold less Pt than a traditional Pt/C fuel cell. In some embodiments, the amount of corrosion of the cathode is reduced compared with a traditional Pt/C fuel cell. In certain embodiments, the nanofibers described herein reduce or substantially eliminate corrosion in the fuel cell. In some embodiments, reduced corrosion (e.g., upon start-up or shut-down), improves the performance of the fuel cell. In one aspect, the fuel cells described herein consist of substantially no carbon. In one aspect, the fuel cells described herein consist of substantially no carbon in the anode.

In some embodiments, the fuel cells described herein have a high current density. The current density is any suitable value. In some embodiments, the current density is about $-0.01$ mA/cm$^2$, about $-0.02$ mA/cm$^2$, about $-0.04$ mA/cm$^2$, about $-0.06$ mA/cm$^2$, about $-0.08$ mA/cm$^2$, about $-0.1$ mA/cm$^2$, about $-0.3$ mA/cm$^2$, and the like. In some embodiments, the current density is at least about $-0.01$ mA/cm$^2$, at least about $-0.02$ mA/cm$^2$, at least about $-0.04$ mA/cm$^2$, at least about $-0.06$ mA/cm$^2$, at least about $-0.08$ mA/cm$^2$, at least about $-0.1$ mA/cm$^2$, at least about $-0.3$ mA/cm$^2$, and the like. In some embodiments, the current density is about 4 times higher than a traditional Pt/C fuel cell.

In some embodiments, the fuel cell has increased reaction stability. In some instances, reaction stability is reported as the number of CV cycles. Cyclic voltammetry or CV is a type of potentiodynmic electrochemical measurement. In some cyclic voltammetry experiments, the working electrode potential is ramped linearly versus time (e.g., like linear sweep voltammetry). In some instances, cyclic voltammetry takes the experiment a step further than linear sweep voltammetry (which ends when it reaches a set potential). When cyclic voltammetry reaches a set potential, the working electrode's potential ramp is inverted. In some embodiments, this inversion happens multiple times during a single experiment. In some embodiments, the current at the working electrode is plotted versus the applied voltage to give the cyclic voltammogram trace. In some instances, cyclic voltammetry is used to study the electrochemical properties of an analyte in solution. In some embodiments, the fuel cells described herein have about 1.5× more, about 2× more, about 3× more, about 4× more, about 5× more, about 10× more, and the like CV cycles than a traditional Pt/C fuel cell.

In one aspect, the fuel cell is significantly thinner than a traditional Pt/C fuel cell. In some instances, reduced thickness allows packing of more fuel cells into a given volume, increasing overall performance and/or reducing cost. The fuel cells have any suitable thickness. In some embodiments, the fuel cell has a thickness of about 0.2 mm, about 0.5 mm, about 0.7 mm, about 1 mm, about 1.5 mm, about 2 mm, about 5 mm, and the like when measured along its shortest dimension. In some embodiments, the fuel cell has a thickness of at most about 0.2 mm, at most about 0.5 mm, at most about 0.7 mm, at most about 1 mm, at most about 1.5 mm, at most about 2 mm, at most about 5 mm, and the like when measured along its shortest dimension.

Batteries

In some instances, a battery is composed of electrochemical cells that are connected in series and/or in parallel to provide the required voltage and capacity. In some instances, each cell consists of a positive and a negative electrode (both sources of chemical reactions) separated by an electrolyte solution, which enables ion transfer between the two electrodes. Once these electrodes are connected externally, chemical reactions proceed in tandem at both electrodes (i.e., thereby liberating electrons and enabling the current to be used). In some instances, the amount of electrical energy (typically expressed per unit of weight, e.g., W·h/kg or mW h/g) that a battery is able to deliver is a function of the cell potential (V) and capacity (A·h/kg), which is linked directly to the chemistry of the system.

In one aspect, described herein are batteries comprising nanofibers. For example, the nanofibers are used in electrodes, optionally anodes or cathodes. In one aspect, described herein is a battery that includes a nanofiber as described herein, includes a battery that includes a nanofiber produced by the methods described herein, and includes a battery that includes a nanofiber produced by the system described herein. In some aspects, the described herein are methods for making and methods for using batteries that include nanofibers.

The present disclosure encompasses all types of batteries. In some embodiments, the battery is a rechargeable lithium battery. In various embodiments, the nanofiber, the anode, and the cathode are any suitable material. In embodiments of rechargeable lithium batteries for example, silicon or germanium are used as anode material (e.g., because these materials have a low discharge potential and high theoretical charge capacity (about 4,200 mA·h/g, and 1,600 mA·h/g respectively) compared to that of graphitic carbon (373 mA·h/g)). In one embodiment, the nanofiber is a Si or Ge nanofiber. In some embodiments, the anode includes Si or Ge nanofibers.

In some instances, silicon anodes have limited applications because silicon's volume changes upon insertion and extraction of lithium, which results in pulverization and capacity fading. In some instances, hollow nanofibers can accommodate volume changes without pulverization. In some embodiments, the nanofibers described herein are hollow. In some embodiments, the batteries described herein comprise a hollow Si or Ge (or combination Si/Ge) nanofiber.

In some embodiments, hollow Si and/or Ge nanofibers are produced via water-based, multi-axial electrospinning. In various embodiments, the nanofibers comprise pure $SiO_2$, and their hybrids with $V_2O_5$, $ZrO_2$, $TiO_2$, Fe, Ni, and carbon with $Fe_3O_4$. In some embodiments, pure ceramic nanofibers such as $SiO_2$, $Al_2O_3$ and $ZrO_2$, etc. are produced via electrospinning of aqueous polymer solution containing their precursors, followed by thermal treatment.

Hollow Si or Ge nanofibers (e.g., for lithium-ion battery anodes) are produced in any suitable manner. In one embodiment, mineral oil and aqueous polymer solution with Si or Ge precursor are coaxially electrospun as core and sheath layer, respectively, followed by the removal of mineral core to create a hollow structure. In one embodiment, gas-assisted coaxial electrospinning is employed (e.g., where an air stream is used as core) to create a hollow structure during the spinning (e.g., and to stretch the sheath layer jet of precursor solution for higher throughput).

Any suitable method of reduction is employed (e.g., following electrospinning of hollow Si or Ge precursor nanofibers). In some embodiments, thermal treatment and/or chemical reduction are applied to obtain pure hollow Si or Ge nanofibers. In some instances, the degree of volume expansion upon insertion and extraction of lithium in Li-ion battery applications is evaluated.

The nanofibers described herein have any suitable amount of volume expansion. In some embodiments, the volume expansion is about 100%, about 200%, about 300%, about 400%, about 600%, about 800%, and the like. In some embodiments, the volume expansion is at most about 100%, at most about 200%, at most about 300%, at most about 400%, at most about 600%, at most about 800%, and the like.

The batteries described herein have any suitable recharging efficiency. In some embodiments, the recharging efficiency is about 500 mAh/g, about 800 mAh/g, about 1,200 mAh/g, about 1,600 mAh/g, about 2,000 mAh/g, about 3,000 mAh/g, about 5,000 mAh/g, about 10,000 mAh/g, and the like. In some embodiments, the recharging efficiency is at least about 500 mAh/g, at least about 800 mAh/g, at least about 1,200 mAh/g, at least about 1,600 mAh/g, at least about 2,000 mAh/g, at least about 3,000 mAh/g, at least about 5,000 mAh/g, at least about 10,000 mAh/g, and the like.

Ultracapacitors

In a conventional capacitor, energy is generally stored by the removal of charge carriers, typically electrons, from one metal plate and depositing them on another. In some instances, this charge separation creates a potential between the two plates, which is harnessed in an external circuit. In some instances, the total energy stored increases with both the amount of charge stored and the potential between the plates. In some instances, the amount of charge stored per unit voltage is a function of the size, the distance, and the material properties of the plates and the material in between the plates (the dielectric), while the potential between the plates is limited by breakdown of the dielectric. In some instances, the dielectric controls the capacitor's voltage. In some instances, changing the dielectric material leads to higher energy density for a given size of capacitor. In one aspect, described herein is the use of nanofibers in capacitors. In various aspects, the present disclosure includes a capacitor that comprises the nanofibers described herein, includes a capacitor that includes a nanofiber produced by the methods described herein, and includes a capacitor that includes a nanofiber produced by the system described herein. In some aspects, the disclosure also includes methods for making and methods for using capacitors that include nanofibers.

An ultracapacitor, also known as an electric double-layer capacitor (EDLC), a supercapacitor, supercondenser, pseudocapacitor, or electrochemical double layer capacitor, is an electrochemical capacitor with relatively high energy density. In some instances, the energy density is on the order of hundreds of times greater compared to conventional electrolytic capacitors. In some instances, ultra-capacitors have a higher power density in comparison with batteries or fuel cells.

In some instances, ultra-capacitors do not have a conventional dielectric. In some instances, ultra-capacitors use "plates" that are two layers of a substrate (optionally the same substrate), rather than two separate plates separated by an intervening substance. In some instances, this "electrical double layer" results in the separation of charge despite the thin physical separation of the layers (e.g., on the order of nanometers). In some instances, the lack of a bulky layer of dielectric in an ultra-capacitor permits the packing of plates with much larger surface area into a given size, resulting in high capacitances compared with a capacitor.

In various embodiments, any of the components of an ultracapacitor comprise nanofibers (for example, porous carbon/BaTiO$_3$/separator). In some embodiments, the nanofibers are produced from a water-based, gas-assisted electrospinning process. In some embodiments, dielectric double layer comprises nanofibers. In one aspect, described herein are ultracapacitors comprising nanofibers. In various aspects, the present disclosure includes an ultracapacitor that includes the nanofibers described herein, includes an ultracapacitor that includes a nanofiber produced by the methods described herein, and includes an ultracapacitor that includes a nanofiber produced by the system described herein. In some embodiments, described herein are methods for making and methods for using ultracapacitors that comprise nanofibers.

In some embodiments, the ultracapacitor comprises porous carbon electrodes with a dielectric layer. In some embodiments, the porous carbon electrodes are formed of nanofibers. In some embodiments, nanofibers are disposed on the carbon electrodes. In various embodiments, the nanofibers comprise any material with a suitable dielectric constant. Non-limiting examples are StTiO$_3$, BaTiO$_3$, SrBaTiO$_3$, mixtures thereof, and combinations thereof. In various embodiments, the nanofibers are of any suitable geometry including hybrid or hollow nanofibers.

In some embodiments, described herein are processes for producing nanofibers suitable for use in an ultracapacitor. In one aspect, the process includes electrospinning a fluid stock, wherein the fluid stock comprises precursor molecules bound to a polymer. In some embodiments, the precursor molecules comprise Ba, St, Ti, or mixtures thereof. In some embodiments, the process includes thermally treating the spun nanofibers.

In some embodiments, the ultracapacitor comprises a thin layer of dielectric nanofibers at the interface between the electrolyte and the electrode (e.g., activated carbon electrode). In some instances, this nanofiber layer results in an increased capacitance. Capacitance density is reported in units of farads per cubic centimeter (F/cm$^3$) or equivalents. In some embodiments, the ultra-capacitors described herein have a capacitance density of about 10 F/cm$^3$, about 20 F/cm$^3$, about 50 F/cm$^3$, about 100 F/cm$^3$, about 200 F/cm$^3$, about 500 F/cm$^3$, about 1,000 F/cm$^3$, and the like. In some embodiments, the ultracapacitor have a capacitance density of at least about 10 F/cm$^3$, at least about 20 F/cm$^3$, at least about 50 F/cm$^3$, at least about 100 F/cm$^3$, at least about 200 F/cm$^3$, at least about 500 F/cm$^3$, at least about 1,000 F/cm$^3$, and the like.

FIG. 45 shows a cross-sectional view of an electrolytic double layer ultracapacitor comprising an electrolyte 4501, a separator 4502, and an activated carbon electrode 4503.

FIG. 46 shows a cross-sectional view of barium titanate nanofibers B laid on the activated carbon A of an ultracapacitor (with electrolyte C).

Solar Cells

In some instances, a solar cell (also called photovoltaic cell or photoelectric cell) is a solid state electrical device that converts the energy of light directly into electricity by the photovoltaic effect. In some instances, assemblies of cells are used to make modules (e.g., solar panels), which are used to capture energy from sunlight.

Photovoltaics is a field of technology related to the use of photovoltaic cells to producing electricity from light (though it is often used specifically to refer to the generation of electricity from sunlight). In some instances, photovoltaic devices are based on the concept of charge separation at an interface of two materials of different conduction mechanism. In some instances, photovoltaic devices are solid-state junction devices, usually made of silicon, (e.g., and profiting from the experience and material availability resulting from the semiconductor industry), however other designs and materials can be utilized.

In various embodiments, any of the components of a solar cell (e.g., thin film solar cell) comprise nanofibers. Exemplary components include an anode, an n-layer, an active layer, a p-layer and a cathode. In some embodiments, the nanofibers are produced by the water-based, gas-assisted electrospinning process described herein. In some embodiments, the n-layer, active layer and p-layer comprise nanofibers. In one aspect, the present disclosure includes uses of nanofibers in solar cells. The present disclosure includes solar cells that include a nanofiber of the invention, includes solar cells that include a nanofiber produced by the methods of the invention, and includes thin film solar cells that include a nanofiber produced by the system of the invention. The disclosure also includes methods for making and methods for using solar cells that include nanofibers.

In one embodiment, the cathode comprises nanofibers (e.g., aluminum). In various embodiments, any suitable material is used as the cathode including pure metal nanofibers such as gold (Au), silver (Ag), nickel (Ni), copper (Co), and/or calcium (Ca).

In some instances, the n-layer provides for transfer of electrons. In some embodiments, the n-layer comprises ZnO nanofibers. Any suitable bandgap material is used as the n-layer including nanofibers of any suitable pure metal oxides such as TiO$_2$.

In one embodiment, the photoactive layer comprises PbSe nanofibers (e.g., where the PbSe crystals are nanoscale in size). Any suitable bandgap material is used as the photoactive layer including nanofibers of any suitable hybrid materials such as CdTe, CdS, PbS, and/or PbTe.

In some instances, the p-layer provides the transfer of holes. In some embodiments, the p-layer comprises NiO nanofibers. Any suitable bandgap material is used as the p-layer including nanofibers of any suitable pure metal oxides such as CuInGaSe$_2$.

In some instances, Indium Tin Oxide ("ITO") is one of the most widely used transparent conducting oxides (e.g., as a solar cell substrate). In some instances, ITO has a superior electrical conductivity and optical transparency. In some instances, ITO is easy to be deposit as a thin film. In one embodiment, the anode comprises ITO nanofibers. In some instances, any suitable conducting, transparent material is used as the anode including nanofibers of any suitable pure inorganic materials such as carbon.

In some embodiments, the cathode comprises Al, the n-layer comprises ZnO, the photoactive layer comprises PbSe, the p-layer comprises NiO, and the anode comprises ITO. In some embodiments, any one or more of the components comprise nanofibers. In some instances, the solar cells based on the nanofibers have good connectivity among nanocrystals in each layer with minimal recombination losses. In some instances, the solar cells based on the nanofibers remove the complications associated with incompatibility among processes for each component.

Figure 37:
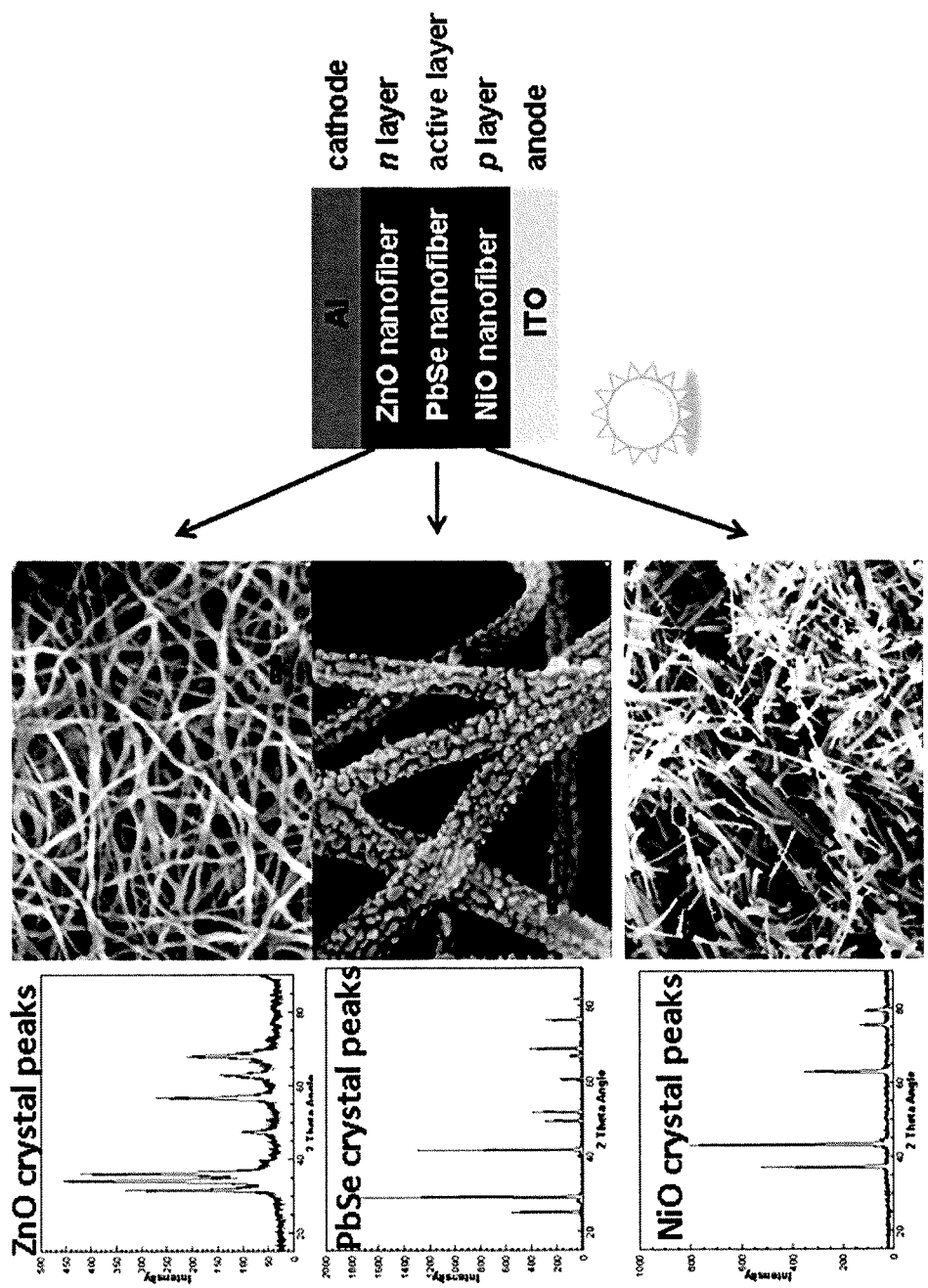
FIG. 37 illustrates micrographs, x-ray diffraction plots and a schematic for a solar cell with a plurality of components made from inorganic nanofibers.

FIG. 37 illustrates an schematic of an embodiment of a solar cell device using nanofibers provided herein.

Flexible Solar Cells

Figure 41:
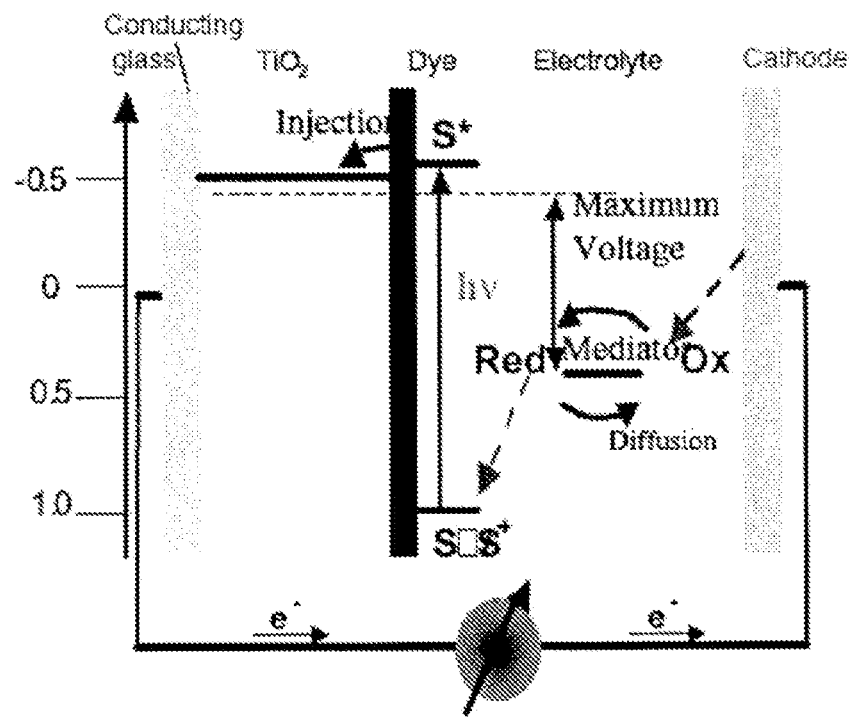
FIG. 41 illustrates an exemplary principle of operation and energy level scheme of a dye-sensitize nanocrystalline solar cell.

In some instances, inorganic solid-state junction devices are being replaced by cells based on nanocrystalline and conducting films (i.e., thin films). In some instances, thin-film structures reduce the cost of photovoltaic devices (e.g., by eliminating the use of the expensive silicon wafers). In some instances, it is now possible to depart completely from solid-state junction devices, by replacing the contacting phase to the semiconductor by an electrolyte, liquid, gel or solid, thereby forming a photo-electrochemical cell. In some instances, the prototype of this family of devices is the dye-sensitized solar cell (see FIG. 41). In some instances, the dye-sensitized solar cell performs the optical absorption and the charge separation processes by the association of a sensitizer as light-absorbing material with a wide band gap semiconductor of nanocrystalline morphology.

In one aspect, described herein are thin film solar cells and photo-electrochemical cells comprising nanofibers. In various aspects, the present disclosure includes thin film solar cells and photo-electrochemical cells that include the nanofibers described herein, includes thin film solar cells and photo-electrochemical cells that include a nanofiber produced by the methods described herein, and includes thin film solar cells and photo-electrochemical cells that include a nanofiber produced by the system described herein. In various aspects, described herein are methods for making and methods for using thin film solar cells and photo-electrochemical cells that include nanofibers.

In some instances, the thin film solar cells and photo-electrochemical cells are flexible. In some instances, ITO (Indium Tin Oxide) is not flexible. In some instances, various flexible substrates based on transparent polymers have been developed, but they do not provide enough thermal stability for thermal treatment of electrode materials (>450° C.) or good adhesion between the substrate and electrodes. In some embodiments, described herein are coaxial nanofibers of alumina (core) and ITO (sheath) (e.g., for use as substrates for flexible solar cell applications). In some embodiments, the alumina/ITO nanofibers have good thermal stability and good adhesion between the substrate and the electrodes.

In some instances, inorganic materials such as alumina, alumina-magnesia and zirconia have been fabricated as flexible substrates for catalytic applications. In some embodiments, insertion of these flexible inorganic materials in the ITO sheath of coaxial nanofibers results in improved flexibility without losing transparency and conductivity. In some instances, such coaxial nanofibers of alumina and ITO are synthesized via water-based spinning (e.g., as substrates for flexible solar cells). In some embodiments, the development of alumina/ITO nanofibers cathodes is carried out in two steps. In some embodiments, aqueous polymer solutions containing high loading of Al precursor and ITO precursor are coaxially electrospun as core and sheath layer, respectively, followed by the thermal treatment to create alumina/ITO coaxial nanofibers.

Figure 43:
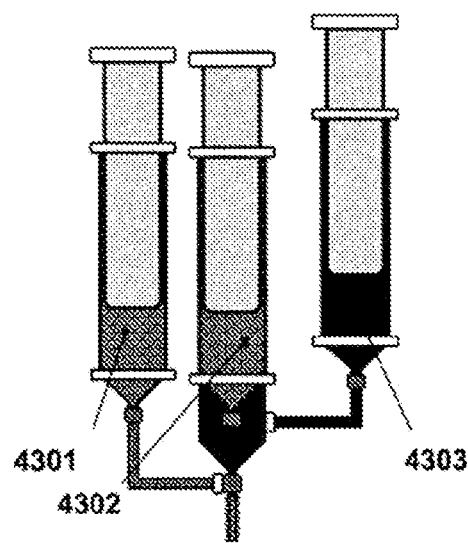
FIG. 43 illustrates a schematic of tri-axial electrospinning.

In some embodiments, a high speed air stream is incorporated into the coaxial procedure as an additional skin layer (i.e., tri-axial jets of alumina precursor (core)/ITO (middle)/air (sheath)). In some embodiments, the gas flow produces nanofibers at a faster rate. In some embodiments, (e.g., as shown in FIG. 43), tri-axial electrospinning is utilized in the confined assembly of block copolymers sandwiched by silica layers.

In various aspects, the present disclosure includes flexible solar cells that include the nanofibers described herein, includes flexible solar cells that include a nanofiber produced by the methods described herein, and includes flexible solar cells that include a nanofiber produced by the system described herein. In some aspects, described herein are methods for making and methods for using flexible solar cells that comprise nanofibers. In one aspect, the disclosure includes solar cells comprising a substrate comprising nanofibers comprising alumina, ITO, or a mixture of alumina and ITO.

Figure 42:
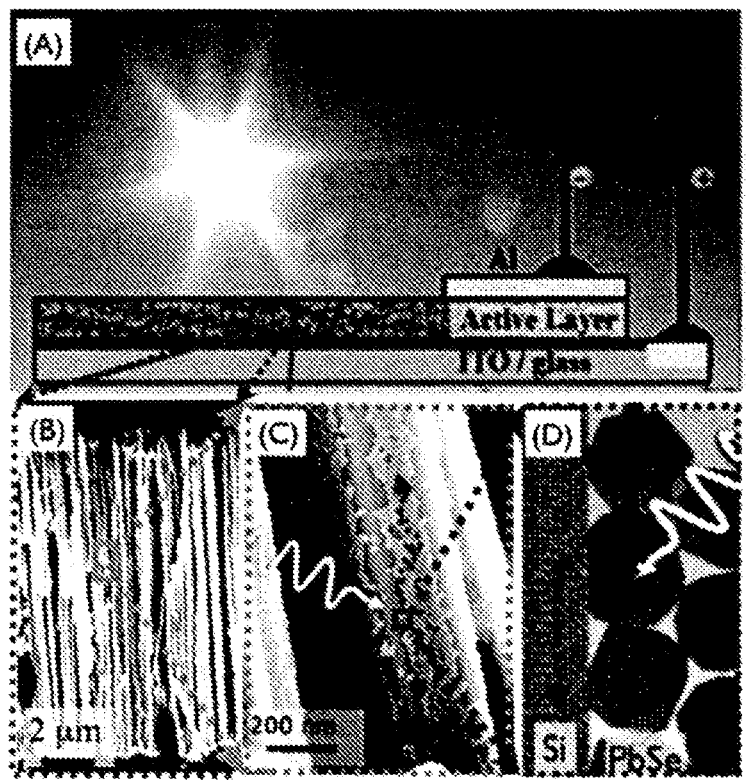
FIG. 42 illustrates an exemplary principle of operation of a thin film nanocrystal/nanowire hybrid solar cell.

FIG. 42 shows the principle of operation of a thin film nanocrystal/nanowire hybrid solar cell.

FIG. 44 shows a TEM image of tri-axial nanofibers of $SiO_2$ (core)/PI-b-PS with $Fe_3O_4$ (middle)/$SiO_2$ (sheath).

Other Uses

In some instances, there are uses for the pure metal and/or ceramic nanofibers other than in electrochemical devices (e.g., filters, sensors, catalysts, membranes, electrodes, tissue regeneration matrixes, and the like).

Catalysis is the change in rate of a chemical reaction due to the participation of a substance called a catalyst. In some instances, unlike reagents that participate in the chemical reaction, a catalyst is not consumed by the reaction itself. In some instances, a catalyst participates in multiple chemical transformations. In some instances, catalysts that speed the reaction are called positive catalysts. In some instances, substances that interact with catalysts to slow the reaction are called inhibitors (or negative catalysts). In some instances, substances that increase the activity of catalysts are called promoters, and substances that deactivate catalysts are called catalytic poisons.

In some instances, solid-state catalysts (sometimes known as a heterogeneous catalyst) catalyze reactions on their surface. Exemplary solid-state catalysts are metals and metal alloys. In some instances, metals and metal alloys are expensive (e.g., precious metals) and reactions are surface-catalyzed. In some instances, it is advantageous to use a catalyst with a high surface to mass ratio (e.g., to maximize performance per cost). In some instances, long, thin nanofibers have a high surface area to mass ratio, so are a desirable material from which to make catalysts.

In one aspect, described herein are catalysts. In various aspects, the present disclosure includes a catalyst that comprises the nanofibers described herein, includes a catalyst that comprises a nanofiber produced by the methods described herein, and includes a catalyst that comprises a nanofiber produced by the system described herein. In some aspects, described herein are methods for making and methods for using catalysts that comprise nanofibers.

In some instances, hydrogen is an energy carrier suitable for use in fuel cells. In one embodiment, the catalyst comprises composite nanofibers comprising a first layer (e.g., comprising Fe or Ni) and a second layer (e.g., comprising $SiO_2$, $ZrO_2$ or $Al_2O_3$). In some embodiments, the catalyst is capable of producing $H_2$ from glucose or cellulose. In some embodiments, the catalyst has a maximum temperature for $H_2$ production of about 60° C. (e.g., increased from about 40° C.).

In some instances, hydrogen sulfide is a poisonous gas that is a pollutant in some industrial processes. In some instances, hydrogen sulfide is removed by a catalyst. In some embodiments, the catalyst comprises composite nanofibers (e.g., comprising ZnO on $ZrO_2$). In some embodiments, the catalyst is capable of removing $H_2S$ from flue gas. In some embodiments, the catalyst is capable of removing $H_2S$ to a concentration of 10 ppm.

In some instances, filters are used to purify particles from a fluid stream. In one aspect, the present disclosure includes filters. In various aspects, the present disclosure includes a filter that comprises the nanofibers described herein, includes a filter that includes a nanofiber produced by the methods described herein, and includes a filter that includes a nanofiber produced by the system described herein. In various aspects, described herein are methods for making and methods for using filters that comprise nanofibers.

In some embodiments, the filter is a water filter. In some embodiments, the filter is an air filter. In some embodiments, the filter is designed to remove particles of a certain size.

In some embodiments, the nanofibers described herein are used in sensors. In one embodiment, the sensor comprises nanofibers comprising metal oxides. In some embodiments, the metal oxides are dispersed in a conducting metal. In some embodiments, a molecule is sensed by a change in current. In one embodiment, the nanofiber comprises $V_2O_5$ and the molecule is ammonia.

In one aspect, the present disclosure includes sensors. In various aspects, the present disclosure includes a sensor that comprises the nanofibers described herein, includes a sensor that includes a nanofiber produced by the methods described herein, and includes a sensor that includes a nanofiber produced by the system described herein. In some embodiments, described herein are methods for making and methods for using sensors that comprise nanofibers.

In some instances, a membrane is a general or selective barrier, which is often thin. In some instances, the nanofibers described herein are formed into membranes. In one embodiment, the membrane comprises nanofibers (e.g., $SiO_2$ comprising metal oxides). In some embodiments, the membrane is capable of removing metal ions from wastewater. In some embodiments, the membrane comprises nanofibers comprising $TiO_2$. In some embodiments, the membrane is capable of degrading organic pollutants. In various embodiments, the pollutant is a pesticide or volatile organic compound. In some instances, the degradation of the pollutant is photocatalytic (i.e., catalyzed by light).

In one aspect, the present disclosure includes membranes. In various aspects, the present disclosure includes a membrane that comprises the nanofibers described herein, includes a membrane that comprises a nanofiber produced by the methods described herein, and includes a membrane that comprises a nanofiber produced by the system described herein. In some aspects, described herein are methods for making and methods for using membranes that comprise nanofibers.

In some instances, an electrode is an electrical conductor used to make contact with a nonmetallic part of a circuit (e.g., a semiconductor, an electrolyte or a vacuum). In some instances, electrodes are utilized in electrochemical devices (e.g., fuel cells, batteries, ultra-capacitors and solar cells). In one aspect, the present disclosure includes electrodes. In various aspects, the present disclosure includes an electrode that comprises the nanofibers described herein, includes an electrode that comprises a nanofiber produced by the methods described herein, and includes an electrode that comprises a nanofiber produced by the system described herein. In some aspects, described herein are methods for making and methods for using electrodes that comprise nanofibers.

In some instances, the nanofibers are used in medicine, including in tissue culture. In some embodiments, described herein are tissue regeneration matrixes. For example, the nanofibers are used for constructing a porous scaffold onto which cells are seeded that grow to fill the scaffold (e.g., thereby producing a material suitable for tissue supplementation or replacement).

In various aspects, the present disclosure includes an electrode that comprises the nanofibers described herein, includes an electrode that comprises a nanofiber produced by the methods described herein, and includes an electrode that comprises a nanofiber produced by the system described herein. In some aspects, described herein are methods for making and methods for using electrodes that comprise nanofibers.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

EXAMPLES

Example 1—Preparing a Fluid Stock of Nickel Acetate and PVA

Two (2) grams of nickel acetate, the metal precursor, was dissolved in 20 ml of 1 molar acetic acid solution. The solution was stirred for 2 hours to create a solution of nickel acetate. The solution was homogenous.

In a second solution, 1 gram of 99.7% hydrolyzed polyvinyl alcohol (PVA) with an average molecular weight of 79 kDa and polydispersity index of 1.5 was dissolved in 10 ml of de-ionized water. The polymer solution was heated to a temperature of 95° C. and stirred for 2 hours to create a homogenous solution.

The nickel acetate solution was then combined with the PVA solution to create a fluid stock. In order to distribute the precursor substantially evenly in the fluid stock, the precursor solution was added gradually to the polymer solution while being continuously vigorously stirred for 2 hours. The mass ratio of precursor to polymer for the fluid feed (based on initial nickel acetate mass) was 2:1.

Example 2—Characterization of a Fluid Stock of Nickel Acetate and PVA

The chemical interaction between the ligand of the metal precursor and the functional group in the polymer backbone resulted in extremely high loading of metal precursors without losing the spinnability. The interaction was demonstrated in the FT-IR study for nanofibers with various ratios of PVA to Ni precursor. As demonstrated in FIG. 2, the drastic reduction of —OH bond and substantial increase in —CO bond were observed at high loading of Ni precursor (Ni:PVA=4:1).

Example 3—Electrospinning a Fluid Stock of Nickel Acetate and PVA

The fluid stock of Example 1 was electrospun by a gas-assisted technique. The overall process and apparatus is depicted in FIG. 1. The fluid stock was loaded into a syringe pump connected to a spinneret with an inner nozzle diameter (fluid stock) of $4.13\times10^{-4}$ m and an outer (air) diameter of $1.194\times10^{-3}$ m. The distance between the nozzle and the collection plate was kept at about 15 cm and the fluid stock was spun at a rate of 0.1 ml/min. A charge of +15 kV was maintained at the collector. The air velocity at the nozzle was 100 m/s. The temperature of the air and fluid stock at the nozzle was 300 K.

Example 4—Calcinating a Fluid Feed of Nickel Acetate and PVA to Create a Pure Nickel Nanofiber The electrospun fluid stock of Example 3 was heated for 2 hours at 600° C. in an atmosphere of 100% Ar gas. In order to visualize the nanofiber before and after calcination an SEM image was taken before and after calcination as depicted in FIG. 3. The diameter of the nanofiber was approximately 500-700 nm as spun and 400-500 nm after calcination. In order to characterize the nanofiber after calcination, an x-ray diffraction measurement was conducted a Scintag Theta-Theta X-ray Diffractometer, indicating that the nanofiber was substantially pure nickel as depicted in FIG. 3.

Example 5—Calcinating a Fluid Feed of Nickel Acetate and PVA to Create a Nickel Oxide Nanofiber The electrospun fluid stock of Example 3 was heated for 2 hours at 600° C. in an atmosphere of air. In order to visualize the nanofiber before and after calcination an SEM image was taken before and after calcination as depicted in FIG. 4. The diameter of the nanofiber was approximately 500-700 nm as spun and 300-500 nm after calcination. An x-ray diffraction measurement indicates that that the nanofiber was substantially pure nickel oxide as depicted in FIG. 4.

Example 6—Calcinating a Fluid Feed of Copper Acetate and PVA to Create a Copper Nanofiber Following the procedure of Example 1, a fluid stock of copper acetate and PVA were prepared with the ratio of precursor:polymer of 2:1. These fluid stocks were electrospun by the procedure of Example 3. The electrospun fluid stock was heated for 2 hours at 800° C. in an atmosphere of 94% Ar and 6% $H_2$ gas. In order to visualize the nanofiber before and after calcination an SEM image was taken before and after calcination as depicted in FIG. 5. The diameter of the nanofiber was approximately 600-800 nm as spun and 300-500 nm after calcination. An x-ray diffraction measurement indicates that that the nanofiber was substantially pure copper as depicted in FIG. 5.

Example 7—Calcinating a Fluid Feed of Copper Acetate and PVA to Create a Copper Oxide Nanofiber The electrospun fluid stock of Example 6 was heated for 2 hours at 600° C. in an atmosphere of air. In order to visualize the nanofiber before and after calcination an SEM image was taken before and after calcination as depicted in FIG. 6. The diameter of the nanofiber was approximately 600-800 nm as spun and 200-600 nm after calcination. An x-ray diffraction measurement indicates that that the nanofiber was substantially pure copper oxide as depicted in FIG. 6.

Example 8—Calcinating a Fluid Feed of Silver Acetate and PVA to Create a Silver Nanofiber Following the procedure of Example 1, a fluid stock of silver acetate and PVA were prepared with ratio of precursor:polymer of 2:1. These fluid stocks were electrospun by the procedure of Example 3. The electrospun fluid stock was heated for 2 hours at 600° C. in an atmosphere of air. In order to visualize the nanofiber before and after calcination an SEM image was taken before and after calcination as depicted in FIG. 7. The diameter of the nanofiber was approximately 900-1200 nm as spun and 600-800 nm after calcination. An x-ray diffraction measurement indicates that that the nanofiber was substantially pure silver as depicted in FIG. 7.

Example 9—Calcinating a Fluid Feed of Iron Acetate and PVA to Create an Iron Nanofiber Following the procedure of Example 1, a fluid stock of iron acetate and PVA were prepared with the ratio of precursor:polymer of 2:1. These fluid stocks were electrospun by the procedure of Example 3. The electrospun fluid stock was heated for 2 hours at 600° C. in an atmosphere of air. In order to visualize the nanofiber before and after calcination an SEM image was taken before and after calcination as depicted in FIG. 8. The diameter of the nanofiber was approximately 300-500 nm as spun and 200-400 nm after calcination. An x-ray diffraction measurement indicates that that the nanofiber was substantially pure iron as depicted in FIG. 8.

Example 10—Calcinating a Fluid Feed of Zinc Acetate and PVA to Create a Zinc Oxide Nanofiber Following the procedure of Example 1, a fluid stock of zinc acetate and PVA were prepared with the ratio of precursor:polymer of 2:1. These fluid stocks were electrospun by the procedure of Example 3. The electrospun fluid stock was heated for 2 hours at 600° C. in an atmosphere of air. In order to visualize the nanofiber before and after calcination an SEM image was taken before and after calcination as depicted in FIG. 9. The diameter of the nanofiber was approximately 500-1000 nm as spun and 400-700 nm after calcination. An x-ray diffraction measurement indicates that that the nanofiber was substantially pure zinc oxide as depicted in FIG. 9.

Example 11—Calcinating a Fluid Feed of Cadmium Acetate and PVA to Create a Cadmium Nanofiber Following the procedure of Example 1, a fluid stock of cadmium acetate and PVA were prepared with the ratio of precursor:polymer of 2:1. These fluid stocks were electrospun by the procedure of Example 3. The electrospun fluid stock was heated for 2 hours at 800° C. in an atmosphere of air. In order to visualize the nanofiber before and after calcination an SEM image was taken before and after calcination as depicted in FIG. 10. The diameter of the nanofiber was approximately 800-1200 nm as spun and 600-900 nm after calcination. An x-ray diffraction measurement indicates that that the nanofiber was substantially pure cadmium as depicted in FIG. 10.

Example 12—Calcinating a Fluid Feed of Zirconium Acetate and PVA to Create a Zirconia Nanofiber Following the procedure of Example 1, a fluid stock of zirconium acetate and PVA were prepared with the ratio of precursor:polymer of 2:1. These fluid stocks were electrospun by the procedure of Example 3. The electrospun fluid stock was heated for 2 hours at 800° C. in an atmosphere of air or 94% Ar and 6% $H_2$ gas. In order to visualize the nanofiber before and after calcination an SEM image was taken before and after calcination as depicted in FIG. 10. The diameter of the nanofiber was approximately 800-1000 nm as spun and 300-600 nm after calcination. An x-ray diffraction measurement indicates that that the nanofiber was substantially pure zirconia as depicted in FIG. 11.

Example 13—Calcinating a Fluid Feed of Lead Acetate and PVA to Create a Lead Nanofiber Following the procedure of Example 1, a fluid stock of lead acetate and PVA were prepared with the ratio of precursor:polymer of 2:1. These fluid stocks were electrospun by the procedure of Example 3. The electrospun fluid stock was heated for 2 hours at 600° C. in an atmosphere of 94% Ar and 6% $H_2$ gas. In order to visualize the nanofiber before and after calcination an SEM image was taken before and after calcination as depicted in FIG. 10. The diameter of the nanofiber was approximately 500-1200 nm as spun and 250-700 nm after calcination. An x-ray diffraction measurement indicates that that the nanofiber was substantially pure lead as depicted in FIG. 12.

Example 14—Fluid Feeds and Nanofibers

Following the procedure of Example 1, fluid stocks are prepared according to Table 2 in the identified precursor-to-polymer load ratio (based on initial precursor mass combined with the polymer). Nanofibers are prepared by calcination under appropriate conditions.

TABLE 2

| precursor | polymer | load ratio | nanofiber |
| --- | --- | --- | --- |
| iron nitrate | PVA | 1:1 | iron |
| iron chloride (+carbon powder) | PVA | 2:1 | steel |
| iron acetate chromium acetate | PVE | 1:1 (89/11) | stainless steel |
| zirconium chloride | PVA | 2:1 | zirconia |
| nickel bromide | PEO | 1:1 | nickel oxide |
| chromium methoxide | PVE | 1.5:1 | chromium |
| tungsten ethoxide | PVA | 3:1 | tungsten |
| CdClOH | polyvinyl pyridine | 1:1 | cadmium oxide |
| silver acetate | PEO | 1:1 | silver |
| nickel nitrate | polyacrylic acid | 2:1 | nickel |
| copper ethoxide | PVA | 1:1 | copper |
| nickel chloride | PVE | 3:1 | nickel oxide |
| zirconium nitrate | polyvinyl pyridine | 1:1 | zirconia |

TABLE 2-continued

| precursor | polymer | load ratio | nanofiber |
| --- | --- | --- | --- |
| copper nitrate | PVE | 3.5:1 | copper oxide |
| nickel t-butoxide | PVO | 1:1 | nickel |
| copper chloride | polyacrylic acid | 1.5:1 | copper |
| aluminum nitrate zirconium acetate | PVE | 2:1 (70/30) | aluminum-zirconia composite |

Example 15—Exploring the Loading of Nickel Acetates on PVA

Following the procedure of Example 1, various fluid stocks of nickel acetate and PVA were prepared with ratios of precursor:polymer of 1:2, 1:1, 2:1, and 4:1. These fluid stocks were electrospun by the procedure of Example 3. At that point, 4 SEM micrographs were taken of the electrospun fluid stock. The electrospun fluid stock was then calcinated by the procedure of Example 4 to create pure Ni nanofibers. At that point, 4 micrographs were taken of the calcinated nanofibers. FIG. 13 shows that the diameter of the nanofibers increased with higher loading of precursor. It also shows that continuous, high-quality nanofibers were formed, particularly at high loading of precursor. TEM micrographs were also taken of the calcinated nanofibers. FIG. 14 shows that there are no voids in the nanofibers, confirming that they are dense and coherent.

Example 16—Investigation of the Atomic Composition of a Pure Nickel Nanofiber

Energy-dispersive x-ray spectroscopy (EDX) was used to measure the elemental composition of a pure nickel nanofiber. FIG. 15 shows that for both dark (left) and bright (right) regions of the TEM images, the majority of the nanofiber is Ni with a small oxygen content. Negligible amounts of carbon are detected.

Example 17—Preparing a PbSe Alloy Nanofiber

A mixture of 50% Pb and 50% Se were formed from lead acetate and Se powder according to the procedures of Example 1. The precursors were further made into a fluid stock with PVA according to the procedure of Example 1 and electrospun according to the procedure of Example 3. The electrospun fluid stock was calcinated by heating for 2 hours at 600° C. in an atmosphere of 100% Ar. Micrographs (FIG. 23) show continuous metal alloy nanofibers and TEM micrographs (FIG. 24) show that they are dense and coherent.

Example 18—Investigation of the Atomic Composition of a PbSe Alloy Nanofiber

Energy-dispersive x-ray spectroscopy (EDX) was used to measure the elemental composition of the PbSe alloy nanofiber produced in Example 17. FIG. 25 shows that for both dark (left) and bright (right) regions of the TEM images, the composition of Pb to Se is maintained as relatively equal. Negligible amounts of carbon are detected.

Figure 30:
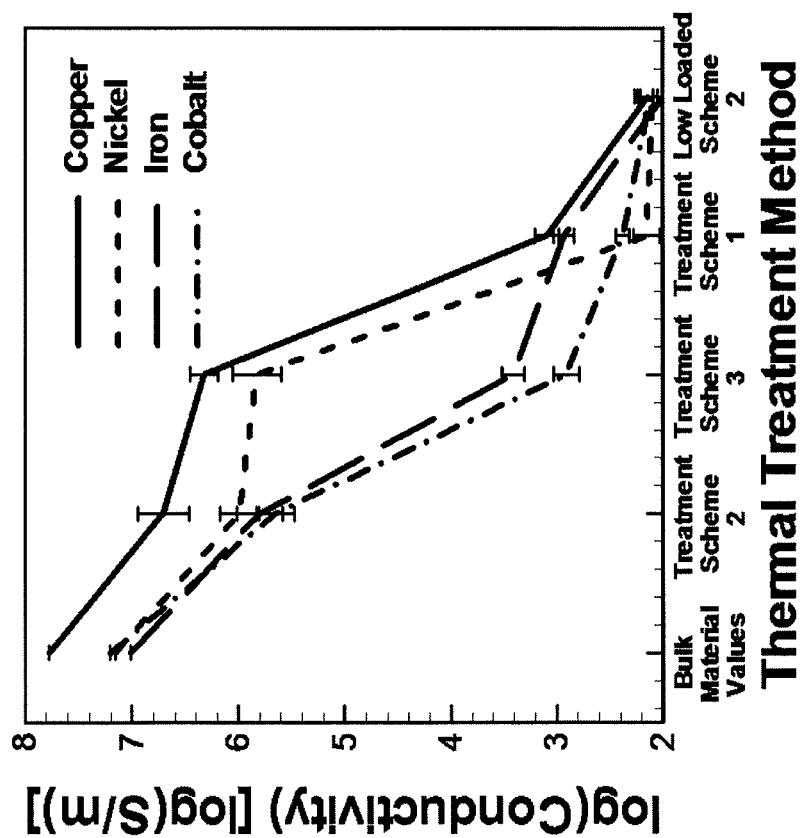
FIG. 30 illustrates a graphic comparing the electrical conductivity of metal nanofibers from various thermal treatment conditions to the conductivity of a metallic film.

Example 19—Investigation of the Electrical Conductivities of Pure Metal Nanofibers A two point probe was used to measure the electric conductivity of various pure metal nanofiber mats obtained via three different thermal treatment conditions (low temperature (400° C.) treatment under inert atmosphere (Treatment Scheme 1), low temperature treatment under air and then under inert atmosphere (Treatment Scheme 2), and high temperature (800° C.) treatment under inert atmosphere (Treatment Scheme 3). FIG. 30 shows that calcinated pure metal nanofibers prepared by the methods of the disclosure (Treatment Scheme 2 and 3) exhibit very high conductivity (greater than $10^6$ S/m) and are nearly as conductive as the known conductivity of the metal when formed into a sheet. On the contrary, metal fibers with Treatment Scheme 1 and from low precursor loading exhibit much lower conductivity (lower than $10^3$ S/m).

Example 20—Preparing a $ZrO_2$/Ni Hybrid Nanofiber

Fluid feeds of Zr acetate and Ni acetate were prepared according to the procedure of Example 1. The two fluid stocks were then electrospun in a co-axial manner using a spinneret similar to the one depicted in FIG. 35. The center conduit contained Ni acetate fluid stock (not air as depicted in FIG. 35) and the outer conduit contained $ZrO_2$ fluid stock. The electrospinning procedure was gas-assisted. The electrospun hybrid fluid stock was calcinated by heating for 2 hours at 600° C. in an atmosphere of air, followed by 2 hours at 600 C in an atmosphere of 94% Ar and 6% $H_2$ gas. Micrographs (FIG. 31) show continuous metal alloy nanofibers and TEM micrographs (FIG. 32) show that they are dense and coherent.

Example 21—Investigation of the Atomic Composition of a $ZrO_2$/Ni Hybrid Nanofiber Energy-dispersive x-ray spectroscopy (EDX) was used to measure the elemental composition of the $ZrO_2$/Ni hybrid nanofiber produced in Example 20. FIG. 33 shows that the dark (left) and bright (right) regions of the TEM images have different compositions. There is much more nickel in the center (left, dark) than on the exterior (right, light). Furthermore, the EDAX shows that the ratio of Zr to O was 1:2 for both cases, indicated the formation of $ZrO_2$.

Example 22—Fuel Cells Electrodes

Disclosed herein are fuel cell electrodes that include Fe—Pt nanofibers. These nanofibers may be prepared according to the procedures and system depicted in FIG. 34. Water-soluble Fe and Pt acetates are mixed with a water-soluble polymer such as PVA to create a fluid stock as in Example 1. The ratio of precursor to polymer is 4:1 in this example. In addition, gas assisted electrospinning will be adapted to increase the throughput. We have demonstrated that the nanofiber production rate can be increased by more than ten times by incorporate air flow into the sheath jet layer in a coaxial scheme. As depicted in FIG. 34, the spinning dope can be prepared by adding an adequate ratio of Fe to Pt precursors to aqueous polymer solution and is used as the core jet in coaxial electrospinning, while a high-speed air stream is used as the sheath layer jet to stretch the core jet of precursor solution. The creation of the face-centered tetragonal structure of Fe—Pt is pursued to enhance oxygen reduction and durability under the minimized Pt loading.

Example 23—Hollow Si or Ge Nanofibers Suitable for Lithium Ion Battery Anodes

FIG. 35 shows an apparatus suitable for producing hollow Si or Ge nanofibers suitable for use as anodes in lithium ion batteries. The high speed air and Si or Ge precursor solution form the core and sheath jets in gas-assisted coaxial electrospinning.

Example 24—$Al_2O_3$/ITO Hybrid Nanofibers Suitable for Use in Flexible Solar Cells FIG. 36 shows a schematic of the process and system for producing $Al_2O_3$/ITO hybrid nanofibers suitable for use in flexible solar cells. Triaxial configuration of $Al_2O_3$/ITO/air in gas-assisted electrospinning is utilized to produce a coaxial $Al_2O_3$/ITO nanofiber. FIG. 37 shows micrographs, x-ray diffraction plots and a schematic for a solar cell with a plurality of components made from nanofibers.

Example 25—Further Examples of Nanofibers

In one aspect, described herein are various nanofibers comprising metal, ceramic, metal alloy, and combinations thereof. In one aspect, described herein are methods for producing various nanofibers comprising metal, ceramic, metal alloy, and combinations thereof. For example: FIG. 16 shows micrographs and an x-ray diffraction plot of ZnO/$ZrO_2$ hybrid nanofibers; FIG. 17 shows micrographs and an x-ray diffraction plot of Ag/$ZrO_2$ hybrid nanofibers; FIG. 18 shows micrographs and an x-ray diffraction plot of Ni/$ZrO_2$ hybrid nanofibers; FIG. 19 shows micrographs and an x-ray diffraction plot of Fe/$ZrO_2$ hybrid nanofibers; FIG. 21 shows micrographs and an x-ray diffraction plot of Ni/$Al_2O_3$ hybrid nanofibers; FIG. 22 shows micrographs and an x-ray diffraction plot of CdSe alloy nanofibers; FIG. 26 shows micrographs and an x-ray diffraction plot of CdTe alloy nanofibers; FIG. 27 shows micrographs and an x-ray diffraction plot of PbTe alloy nanofibers; FIG. 28 shows micrographs and an x-ray diffraction plot of $Fe_3O_4$/FeNi alloy nanofibers; and FIG. 29 shows TEM micrographs of $Fe_3O_4$/FeNi alloy nanofibers. In other aspects, processes describe in the examples herein were utilized to make the nanofibers of Table 1.

FIG. 20 shows TEM micrographs of various hybrid nanofibers.

What is claimed is:
1. A nanofiber comprising:
 a metal containing material comprising one or more metal containing precursors, wherein the one or more metal containing precursors comprise one or more electrophilic moieties or one or more nucleophilic moieties;
 a non-metal material comprising a polymer comprising a plurality of nucleophilic moieties or a plurality of electrophilic moieties;
 wherein the polymer is configured to react with the one or more metal containing precursors through a non-sol-gel reaction between the nucleophilic moieties and the electrophilic moieties; and
 a precursor-polymer bond or a precursor-polymer association between the polymer and the one or more metal containing precursors
 wherein the nanofiber is a precursor nanofiber.
2. The nanofiber of claim 1, wherein the polymer comprises partially or completely ionized forms.
3. The nanofiber of claim 1, wherein a weight to weight ratio of the one or more metal containing precursors to the polymer is at least 3:1.
4. The nanofiber of claim 1, wherein the metal containing material further comprises a metal, metal alloy, metal oxide, metal-non-metal alloy, ceramic, or any combination thereof.

5. The nanofiber of claim 1, wherein the non-metal material further comprises a carbonaceous material.

6. The nanofiber of claim 1, wherein the precursor-polymer bond or the precursor-polymer association comprises a covalent bond, a metal-ligand complex, an ionic bond, or a Lewis base/Lewis acid interaction formed by the one or more metal containing precursors associating with, or binding to the polymer.

7. A process for producing the nanofiber of claim 1, comprising:
   providing a fluid stock comprising:
   1) the one or more metal containing precursors comprising one or more of the electrophilic moieties; and the non-metal material comprising the polymer comprising a plurality of the nucleophilic moieties; or
   2) the one or more metal containing precursors comprising one or more of the nucleophilic moieties; and the non-metal material comprising the polymer comprising a plurality of the electrophilic moieties;
      mixing the one or more metal containing precursors with the polymer such that the metal containing precursors react with or more of the non-sol-gel reaction between the nucleophilic moieties and the electrophilic moieties;
      electrospinning the fluid stock to form the nanofiber.

8. The process of claim 7, further comprising one of more processes for treating the nanofiber, wherein the processes are selected from heating, calcination, solubilizing the polymer, chemically degrading the polymer or any combination thereof.

* * * * *